(12) United States Patent
Stamford et al.

(10) Patent No.: US 9,145,426 B2
(45) Date of Patent: Sep. 29, 2015

(54) PYRROLIDINE-FUSED THIADIAZINE DIOXIDE COMPOUNDS AS BACE INHIBITORS, COMPOSITIONS, AND THEIR USE

(75) Inventors: Andrew W. Stamford, Chatham, NJ (US); Eric J. Gilbert, Scotch Plains, NJ (US); Jared N. Cumming, Garwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/009,654

(22) PCT Filed: Apr. 2, 2012

(86) PCT No.: PCT/US2012/031783
§ 371 (c)(1),
(2), (4) Date: Oct. 3, 2013

(87) PCT Pub. No.: WO2012/138590
PCT Pub. Date: Oct. 11, 2012

(65) Prior Publication Data
US 2014/0023667 A1 Jan. 23, 2014

Related U.S. Application Data

(60) Provisional application No. 61/473,066, filed on Apr. 7, 2011.

(51) Int. Cl.
*C07D 513/04* (2006.01)
*A61K 31/549* (2006.01)
*A61K 45/06* (2006.01)

(52) U.S. Cl.
CPC ............ *C07D 513/04* (2013.01); *A61K 31/549* (2013.01); *A61K 45/06* (2013.01)

(58) Field of Classification Search
CPC ............................ C07D 513/04; A61K 31/549
USPC ......................................... 544/10; 514/222.8
See application file for complete search history.

(56) References Cited

U.S. PATENT DOCUMENTS

| | | |
|---|---|---|
| 5,534,520 A | 7/1996 | Fisher et al. |
| 6,683,091 B2 | 1/2004 | Asberom et al. |
| 7,648,983 B2 | 1/2010 | Audia et al. |
| 7,994,167 B2 | 8/2011 | Frank et al. |
| 8,338,413 B1 | 12/2012 | Rueeger |
| 8,557,826 B2 | 10/2013 | Stamford et al. |
| 8,563,543 B2 | 10/2013 | Scott et al. |
| 8,569,310 B2 | 10/2013 | Iserloh et al. |
| 8,729,071 B2 | 5/2014 | Scott et al. |
| 8,940,748 B2 | 1/2015 | Scott et al. |
| 9,029,362 B2 | 5/2015 | Scott et al. |
| 2006/0034848 A1 | 2/2006 | Kinoshita et al. |
| 2006/0281730 A1 | 12/2006 | Zhu et al. |
| 2007/0060575 A1 | 3/2007 | Zhu |
| 2007/0072925 A1 | 3/2007 | Malamas et al. |
| 2007/0287692 A1 | 12/2007 | Wu et al. |
| 2007/0299087 A1 | 12/2007 | Berg et al. |

(Continued)

FOREIGN PATENT DOCUMENTS

| | | |
|---|---|---|
| EP | 1942105 | 7/2008 |
| JP | 2012250933 | 12/2012 |

(Continued)

OTHER PUBLICATIONS

PCT Search Report for PCT/US12/31783 dated Jul. 20, 2012; 3 pages.
PCT Written Opinion for PCT/US12/31783 dated Jul. 20, 2012; 5 pages.
Abramov, et al., Amyloid—as a positive endogenous regulator of release probability at hippocampal synapses, Nature Neuroscience 12, 1567-1576 (2009) Published online: Nov. 22, 2009 | doi:10.1038/nn.2433.
Barton, et al., On the Structure of Some Substituted 4, 6-Pyrimidinones, Department of Organic Chemistry, College of Medicine, Jagiellonian University, Ingardena 3, 30-060-Krakow, Poland, Polish J. Chem., 69, 235-245 (1995), revised manuscript Oct. 25, 1994.

(Continued)

*Primary Examiner* — Kahsay Habte
(74) *Attorney, Agent, or Firm* — Keith D. MacMillan; John C. Todaro

(57) ABSTRACT

In its many embodiments, the present invention provides certain iminothiadiazine dioxide compounds, including compounds Formula (I):

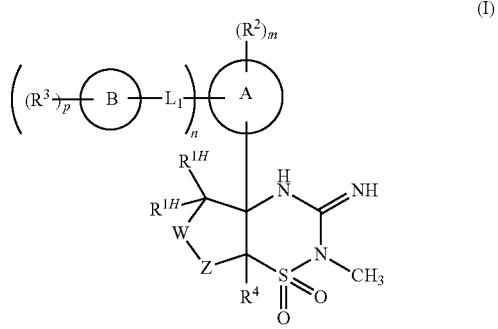

and tautomers and stereoisomers thereof, and pharmaceutically acceptable salts of said compounds, said tautomeros and said stereoisomers, wherein each of W, Z, $R^{1H}$, $R^2$, $R^3$, $R^4$, ring A, ring B, m, n, p, and $-L_1-$ is as defined herein. The novel compounds of the invention have surprisingly been found to exhibit properties which are expected to render them advantageous as BACE inhibitors and/or for the treatment and prevention of various pathologies related thereto. Pharmaceutical compositions comprising one or more such compounds (alone and in combination with one or more other active agents), and methods for their preparation and use, including Alzheimer's disease, are also disclosed.

15 Claims, No Drawings

(56) References Cited

U.S. PATENT DOCUMENTS

| | | |
|---|---|---|
| 2008/0200445 A1 | 8/2008 | Zhu et al. |
| 2009/0023762 A1 | 1/2009 | Berg et al. |
| 2009/0062282 A1 | 3/2009 | Albert et al. |
| 2009/0209755 A1 | 8/2009 | Suzuki et al. |
| 2009/0253640 A1 | 10/2009 | Lamango |
| 2010/0075957 A1 | 3/2010 | Tamura et al. |
| 2010/0317850 A1 | 12/2010 | Suzuki et al. |
| 2011/0009395 A1 | 1/2011 | Audia et al. |
| 2011/0046122 A1 | 2/2011 | Andreini et al. |
| 2011/0152253 A1 | 6/2011 | Motoki et al. |
| 2012/0035195 A1 | 2/2012 | Banner et al. |
| 2012/0184540 A1 | 7/2012 | Andreini et al. |
| 2012/0189642 A1 | 7/2012 | Scott et al. |
| 2012/0195881 A1 | 8/2012 | Iserloh et al. |
| 2012/0196863 A1 | 8/2012 | Andreini et al. |
| 2012/0202803 A1 | 8/2012 | Hilpert et al. |
| 2012/0258961 A1 | 10/2012 | Suzuki et al. |
| 2012/0258962 A1 | 10/2012 | Hilpert et al. |
| 2012/0302549 A1 | 11/2012 | Narquizian et al. |
| 2014/0023668 A1 | 1/2014 | Cumming et al. |
| 2014/0128382 A1 | 5/2014 | Wu et al. |
| 2014/0200213 A1 | 7/2014 | Wu et al. |

FOREIGN PATENT DOCUMENTS

| | | |
|---|---|---|
| WO | WO9004917 | 5/1990 |
| WO | WO9304047 | 3/1993 |
| WO | WO9614844 | 5/1996 |
| WO | WO0051992 | 9/2000 |
| WO | WO2005058311 | 6/2005 |
| WO | WO2006009653 | 1/2006 |
| WO | WO2006009655 | 1/2006 |
| WO | WO2006041404 | 4/2006 |
| WO | WO2006041405 | 4/2006 |
| WO | WO2006044497 | 4/2006 |
| WO | WO2006060109 | 6/2006 |
| WO | WO2006065277 | 6/2006 |
| WO | WO2006076284 | 7/2006 |
| WO | WO2006138192 | 12/2006 |
| WO | WO2006138195 | 12/2006 |
| WO | WO2006138217 | 12/2006 |
| WO | WO2006138264 | 12/2006 |
| WO | WO2006138265 | 12/2006 |
| WO | WO2006138266 | 12/2006 |
| WO | WO2007005366 | 1/2007 |
| WO | WO2007005404 | 1/2007 |
| WO | WO2007011810 | 1/2007 |
| WO | WO2007016012 | 2/2007 |
| WO | WO2007038271 | 4/2007 |
| WO | WO2007078813 | 4/2007 |
| WO | WO2007049532 | 5/2007 |
| WO | WO2007050721 | 5/2007 |
| WO | WO2007053506 | 5/2007 |
| WO | WO2007058580 | 5/2007 |
| WO | WO2007058581 | 5/2007 |
| WO | WO2007058583 | 5/2007 |
| WO | WO2007058601 | 5/2007 |
| WO | WO2007058602 | 5/2007 |
| WO | WO2007073284 | 6/2007 |
| WO | WO2007100536 | 9/2007 |
| WO | WO2007114771 | 10/2007 |
| WO | WO2007145568 | 12/2007 |
| WO | WO2007145569 | 12/2007 |
| WO | WO2007145570 | 12/2007 |
| WO | WO2007145571 | 12/2007 |
| WO | WO2007146225 | 12/2007 |
| WO | WO2008022024 | 2/2008 |
| WO | WO2008063114 | 5/2008 |
| WO | WO2008073365 | 6/2008 |
| WO | WO2008073370 | 6/2008 |
| WO | WO2008076043 | 6/2008 |
| WO | WO2008076044 | 6/2008 |
| WO | WO2008076045 | 6/2008 |
| WO | WO2008076046 | 6/2008 |
| WO | WO2008133273 | 6/2008 |
| WO | WO2008133274 | 6/2008 |
| WO | WO2008103351 | 8/2008 |
| WO | WO2008115552 | 9/2008 |
| WO | WO2008118379 | 10/2008 |
| WO | WO2011009897 | 1/2009 |
| WO | WO2009020580 | 2/2009 |
| WO | WO2009091016 | 7/2009 |
| WO | WO2009108550 | 9/2009 |
| WO | 2009131975 A1 | 10/2009 |
| WO | WO2009131974 | 10/2009 |
| WO | WO2009131975 | 10/2009 |
| WO | WO2009134617 | 11/2009 |
| WO | WO2009136350 | 11/2009 |
| WO | WO2009151098 | 12/2009 |
| WO | WO2010013302 | 2/2010 |
| WO | WO2010013794 | 2/2010 |
| WO | WO2010021680 | 2/2010 |
| WO | WO2010030954 | 3/2010 |
| WO | WO2010038686 | 4/2010 |
| WO | WO2010047372 | 4/2010 |
| WO | WO2010128058 | 11/2010 |
| WO | WO2011005738 | 1/2011 |
| WO | WO2011009898 | 1/2011 |
| WO | WO2011009943 | 1/2011 |
| WO | WO2011020806 | 2/2011 |
| WO | WO2011029803 | 3/2011 |
| WO | WO2011044181 | 4/2011 |
| WO | WO2011044184 | 4/2011 |
| WO | WO2011044185 | 4/2011 |
| WO | WO2011044187 | 4/2011 |
| WO | WO2011058763 | 5/2011 |
| WO | WO2011069934 | 6/2011 |
| WO | WO2011070029 | 6/2011 |
| WO | WO2011070781 | 6/2011 |
| WO | WO2011071057 | 6/2011 |
| WO | WO2011071109 | 6/2011 |
| WO | WO2011071135 | 6/2011 |
| WO | WO2011072064 | 6/2011 |
| WO | WO2011077726 | 6/2011 |
| WO | WO2011080176 | 7/2011 |
| WO | WO2011106414 | 9/2011 |
| WO | WO2011115928 | 9/2011 |
| WO | WO2011115938 | 9/2011 |
| WO | WO2011123674 | 10/2011 |
| WO | WO2011130347 | 10/2011 |
| WO | WO2011130741 | 10/2011 |
| WO | WO2011138293 | 11/2011 |
| WO | WO2011154374 | 12/2011 |
| WO | WO2011154431 | 12/2011 |
| WO | WO2012006953 | 1/2012 |
| WO | WO2012040641 | 3/2012 |
| WO | WO2012057247 | 5/2012 |
| WO | WO2012057248 | 5/2012 |
| WO | WO2012071279 | 5/2012 |
| WO | WO2012071458 | 5/2012 |

OTHER PUBLICATIONS

Bayden, et al., Web application for studying the free energy of binding and protonation states of protein-ligand complexes based on HINT, J Comput Aided Mol Des (2009) 23:621-632.

Chiriano, et al., Sequential Virtual Screening Approach to the Identification of Small Organic Molecules as Potential BACE-1 Inhibitors, Chem Biol Drug Des 2011; 77: 268-271.

Cho, et al, S-Nitrosylation of Drp1 Mediates β-Amyloid-Related Mitochondrial Fission and Neuronal Injury, Science Apr. 3, 2009: vol. 324 No. 5923 pp. 102-105.

Cole, et al., Review: The Alzheimer's disease B-secretase enzyme, BACEI, Molecular Neurodegeneration 2007, 2:22, Published Nov. 15, 2007.

Cumming JN, et al. Piperazine sulfonamide BACE1 inhibitors: Design, synthesis, and in vivo characterization. Bioorg Med Chem Lett. 2010;20:2837-42.

Cumming JN, et al. Rational design of novel, potent piperazinone and imidazolidinone BACE1 inhibitors. Bioorg Med Chem Lett. 2008;18:3236-41.

Cumming JN, et al. Structure based design of iminohydantoin BACE1 inhibitors: identification of an orally available, centrally

(56) References Cited

OTHER PUBLICATIONS active BACE1 inhibitor. Bioorg Med Chem Lett. Apr. 1, 2012;22(7):2444-9. doi: 10.1016/j.bmcl.2012.02.013.
Cumming, et al., Design and development of cyclic amine BACE1 inhibitors, Current Opinion in Drug Discovery and Development, 2004, 7(4), 536-556.
Edwards, et al., Application of Fragment-Based Lead Generation to the Discovery of Novel, Cyclic Amidine p-Secretase Inhibitors with Nanomolar Potency, Cellular Activity, and High Ligand Efficiency, 1. Med. Chenl. 2007,50, 5912-5925.
Evin, et al., BACE Inhibitors as Potential Drugs for the Treatment of Alzheimer's Disease: Focus on Bioactivity, Recent Patents on CNS Drug Discovery, 2011, 6, 91-106.
Farah, et al., Reduced BACE1 Activity Enhances Clearance of Myelin Debris and Regeneration of Axons in the Injured Peripheral Nervous System, The Journal of Neuroscience, Apr. 13, 2011 • 31(15):5744-5754.
Getchell, et al., 3-Nitrotyrosine immunoreactivity in olfactory receptor neurons of patients with Alzheimer's disease: implications for impaired odor sensitivity, Neurobiology of Aging 24 (2003) 663-673. accepted Oct. 8, 2002, pp. 663-673.
Ginman, et al., "Core refinement toward permeable B-Secretase (BACE-1) Inhibitors with low hERG Activity", Journal of Medicinal Chemistry, Rec'd Aug. 12, 2012.
Gravenfors, et al., "New Aminimidazoles as B-Secretase (BACE-1) inhibitors Showing amylod-B (AB) lowering in the brain", Journal of Medicinal Chemistry, 2012, 9297-9311.
Guo, et al., Targeting Amyloid-B in Glaucoma Treatment, pp. 13444-13449, PNAS, Aug. 14, 2007, vol. 104, No. 33.
Hilpert, et al., "B-Secretase (BACE1) Inhibitors with high in vivo efficacy suitable for clinical evaluation of Alzheimer's disease", Journal of Medicinal Chemistry, 2013, 3980-3995.
Huang, et al., "Structure- and Property-Based Design of Aminooxazoline Xanthines as selective, orally efficacious, and CNS Penetrable Bace inhibitors for the treatment of Alzheimer's disease", Journal of Medicinal Chemistry, Special Issue: Alzheimer's Disease, 2012, 55, 9156-9169.
Huang, et al., Pharmacophore Model Construction of, 8-Secretase Inhibitors, Acta Chimica Sinica, vol. 66, No. 16, 2008, pp. 1889-1897. (English Abstract).
Hunt, et al., "Spirocyclic B-Site Amyloid Precursor Protein Cleaving Enzyme 1 (BACE1) Inhibitors: From hit to Lowering of Cerebralspinal fluid (CSF) Amyloid-B in a higher species", Journal of Medicinal Chemistry 2013, 56, 3379-3403.
Iserloh U, et al. Discovery of an orally efficacious 4-phenoxypyrrolidine-based Bace-1 inhibitor. Bioorg Med Chem Lett. 2008;18:418-22.
Iserloh U, et al. Potent pyrrolidine- and piperidine-based Bace-1 inhibitors. Bioorg Med Chem Lett. 2008; 18:414-7.
Jin, et al., Evidence for dimeric BACE-mediated APP processing, Biochemical and Biophysical Research Communications 393 (2010) 21-27.
Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.
Luo, et al., mice deficient in BACE1, the Alzheimer's B-secretase, have normal phenotype and abolished B-amyloid, Nature Neuroscience, vol. 4, No. 3, Mar. 2001.
Malamas, et al., Aminoimidazoles as potent and selective human B-secretase (BACE1) inhibitors, J. Med. Chem., 2009, 52, 6314-6323.
Malamas, et al., Design and Synthesis of 5,50-Disubstituted Aminohydantoins as Potent and Selective Human β-Secretase (BACE1) Inhibitors, J. Med. Chem. 2010, 53, 1146-1158 (Published on Web Dec. 7, 2009).
Malamas, et al., Design and synthesis of aminohydantoins as potent and selective human b-secretase (BACE1) inhibitors with enhanced brain permeability, Bioorganic & Medicinal Chemistry Letters 20 (2010) 6597-6605.
Malamas, et al., Di-substituted pyridinyl aminohydantoins as potent and highly selective human b-secretase (BACE1) inhibitors, Bioorganic & Medicinal Chemistry 18 (2010) 630-639.
Malamas, et al., New pyrazolyl and thienyl aminohydantoins as potent BACE1 inhibitors: Exploring the S20 region, Bioorganic & Medicinal Chemistry Letters 21 (2011) 5164-5170.
Malamas, et al., Novel pyrrolyl 2-aminopyridines as potent and selective human b-secretase (BACE1) inhibitors, Bioorganic & Medicinal Chemistry Letters 20 (2010) 2068-2073 (Available online Feb. 23, 2010).
Mandal M, et al., Design and validation of bicyclic iminopyrimidinones as beta amyloid cleaving enzyme-1 (BACE1) inhibitors: conformational constraint to favor a bioactive conformation. J Med Chem. Nov. 8, 2012;55(21):9331-45. doi: 10.1021/jm301039c.
May, et al., Robust Central Reduction of B Amyloid in Humans with an Orally Available, Non-Peptidic B-Secretase Inhibitor, The Journal of Neuroscience, Nov. 16, 2011 • 31(46):16507-16516 • 16507.
McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.
Nowak, et al., Discovery and initial optimization of 5,50-disubstituted aminohydantoins as potent b-secretase (BACE1) inhibitors, Bioorganic & Medicinal Chemistry Letters 20 (2010) 632-635. (Available online Nov. 20, 2009).
Ohno, et al., BACE1 deficiency rescues memory deficits and Cholinergic function in a mouse model of Alzheimer's disease, Neuron, vol. 41, 27-33, Jan. 8, 2004.
Ohno, et al. BACE1 gene deletion prevents neuron loss and memory deficits in 5XFAD APP/PS1 transgenic mice, Neurobiology of disease 26 (2006), pp. 134-145.
Osherovich, L. AB's Dry (AMD) Humor, SciBX 4(26); doi:10.1038/scibx.2011.727, Published online Jun. 30, 2011.
Probst, et al., Small-molecule BACE1 inhibitors: a patent literature review, Expert Opinion on Therapeutic Patents, (2006-2011), 2012, 22(5):511-540.
Roberds, et al., Bace knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.
Salloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.
Scott, et al., "Novel Imino Pyrimidinone B-Secretase (BACE1) Inhibitors. P1 Thiophenes", Poster presentation, American Chemical Society, Sprint 2011.
Southan, BACE2 as a New Diabetes Target: a patent review 2010-2012, Expert Opinion on Therapeutic Patents, 2013, Informa UK, Ltd., ISSN 1354-3776, e-1744-7674.
Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.
Stachel, et al., Structure-Based Design of Potent and Selective Cell-Permeable Inhibitors of Human Beta-Secretase (BACE-1), J. Med. Chem., 2004, vol. 47, pp. 6447-6450.
Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.
Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.
Stamford, et al., Inhibitors of BACE for treating Alzheimer's disease: a fragment-based drug discovery story, Current Opinion in Chemical Biology; v:17 i:3 p:320-328; Jun. 2013 Elsevier.
Statchel, et al., Conformationally biased P3 amide replacements of b-secretase inhibitors, S. J. Stachel et al./Bioorg. Med. Chem. Lett. 16.(2006) 641-644.

(56) References Cited

OTHER PUBLICATIONS

Statchel, et al., Discovery of aminoheterocycles as a novel b-secretase inhibitor class: pH dependence on binding activity part 1, Bioorganic & Medicinal Chemistry Letters 19 (2009) 2977-2980.

Swahn, et al., "Aminimidazoles as BACE-1 inhibitors: The challenge to achieve in vivo brain efficacy", Bioorganic and Medicinal Chemistry Letters, 22 (2012) 1854-1859.

Swahn, et al., "Design and synthesis of beta-site amyloid precursor protein cleaving enzyme (BACE1) inhibitors with in vivo brain reduction of B-amyloid peptides", Journal of Medicinal Chemistry, 2012, 55, 9346-9361.

Tresadern, et al., Rational design and synthesis of aminopiperazinones as b-secretase (BACE) inhibitors, Bioorganic & Medicinal Chemistry Letters 21 (2011) 7255-7260.

Wang YS, et al., Application of fragment-based NMR screening, X-ray crystallography, structure-based design, and focused chemical library design to identify novel microM leads for the development of nM BACE-1 (beta-site APP cleaving enzyme 1) inhibitors. J Med Chem. 2010;53:942-50.

Weiner, Further insights into Alzheimer disease pathogenesis, Weiner, M.W. Nat. Rev. Neurol. 9, 65-66 (2013); published online Jan. 22, 2013.

Welch, J.T., et al., The synthesis and biological activity of pentafluorosulfanyl analogs of fluoxetine, fenfluramine, and norfenfluramine, Bioorganic & Medicinal Chemistry; v:15 i:21 p:6659-6666; Nov. 1, 2007.

Wyss Df, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

Zhi, et al., Self-organizing molecular field analysis on human b-secretase nonpeptide inhibitors: 5, 5-disubstituted aminohydantoins, European Journal of Medicinal Chemistry 46 (2011) 58-64.

Zhou, et al., An efficient synthesis of 2-amino-4-(4-fluoro-3-(2-fluoropyridin-3-yl)phenyl)-4-(4-methoxy-3-methylphenyl)-1-methyl-1H-imidazol-5(4H)-one, a potent BACE1 inhibitor, ARKIVOC 2010 (vi) 84-88.

Zhou, et al., Pyridinyl aminohydantoins as small molecule BACE1 inhibitors, Bioorganic & Medicinal Chemistry Letters 20 (2010) 2326-2329 (Available online Feb. 12, 2010).

Zhu, et al., Discovery of Cyclic Acylguanidines as Highly Potent and Selective β-Site Amyloid Cleaving Enzyme (Bace) Inhibitors: Part I; Inhibitor Design and Validation),1, J. Med. Chem. 2010, 53, 951-965.

PYRROLIDINE-FUSED THIADIAZINE DIOXIDE COMPOUNDS AS BACE INHIBITORS, COMPOSITIONS, AND THEIR USE

CROSS-REFERENCE TO RELATED APPLICATIONS

This application is a U.S. National Stage Application under 35 U.S.C. 371 of PCT Application No. PCT/US2012/031783, filed Apr. 2, 2012, which claims priority under 35 U.S.C. 199(e) of U.S. Provisional Application No. 61/473,066, filed Apr. 7, 2011.

FIELD OF THE INVENTION

This invention provides certain imino thiadiazine dioxide compounds and compositions comprising these compounds. The imino thiadiazine compounds and compositions of the invention have, surprisingly and advantageously, improved solution stability and improved expected exposure to target sites for centrally acting compounds compared to certain known imino pyrimidinones. They are useful as BACE inhibitors and for the treatment and prevention of various pathologies, including those related to β-amyloid production.

BACKGROUND

Amyloid beta peptide ("Aβ") is a primary component of β amyloid fibrils and plaques, which are regarded playing a role in an increasing number of pathologies. Examples of such pathologies include, but are not limited to, Alzheimer's Disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ($\beta_2$ microglobulins and complications arising therefrom), neurodegenerative diseases such as scrapie, bovine spongiform encephalitis, and Creutzfeld-Jakob disease and the like.

Aβ peptides are short peptides which are made from the abnormal proteolytic break-down of the transmembrane protein called amyloid precursor protein ("APP"). Aβ peptides are made from the cleavage of APP by β-secretase activity at the position corresponding to the N-terminus of Aβ, and by γ-secretase activity at the position corresponding to the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of abnormal Aβ by β-secretase activity. The inhibition of BACE-1 has been shown to inhibit the production of Aβ.

Alzheimer's disease is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, abnormally formed through β-secretase and γ-secretase activity, can form tertiary structures that aggregate to form amyloid fibrils. Aβ peptides have also been shown to form Aβ oligomers (sometimes referred to as "Abeta aggretates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ and Aβ fibrils and plaque play a causal role in AD pathophysiology. (See Ohno et al., *Neurobiology of Disease*, No. 26 (2007), 134-145.) Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuron cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., *J. Bio. Chem.*, vol. 282, No. 36 (September 2007), have shown that partial reductions of BACE-1 enzyme activity and concomitant reductions of Aβ levels lead to a dramatic inhibition of Aβ-driven AD-like pathology (while minimizing side effects of full inhibition), making β-secretase a target for therapeutic intervention in AD. Ohno et al. *Neurobiology of Disease*, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and conclude that BACE-1 inhibition has been validated as an approach for the treatment of AD. Roberds et al., *Human Mol. Genetics*, 2001, Vol. 10, No. 12, 1317-1324, established that inhibition or loss of β-secretase activity produces no profound phenotypic defects while inducing a concomitant reduction in β-amyloid peptide. Luo et al., *Nature Neuroscience*, vol. 4, no. 3, March 2001, report that mice deficient in BACE-1 have normal phenotype and abolished β-amyloid generation.

BACE-1 has also been identified or implicated as a therapeutic target for a number of other diverse pathologies in which Aβ or Aβ fragments have been identified to play a role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 may be useful in reducing Alzheimer's type pathology in Down's syndrome patients.

Another example is in the treatment of glaucoma (Guo et al., *PNAS*, vol. 104, no. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., *Neurobiology of Aging*, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., *Ann NY Acad Sci* 2002; 855:723-31; Crino P B, Martin J A, Hill W D, et al., *Ann Otol Rhinol Laryngol*, 1995; 104:655-61; Davies D C, et al., *Neurobiol Aging*, 1993; 14:353-7; Devanand D P, et al., *Am J Psychiatr*, 2000; 157:1399-405; and Doty R L, et al., *Brain Res Bull*, 1987; 18:597-600. It is reasonable to suggest that addressing such changes by reduction of Aβ by inhibition of BACE-1 could help to restore olfactory sensitivity in patients with AD.

Other diverse pathologies characterized by the inappropriate formation and deposition of Aβ or fragments thereof, and/or by the presence of amyloid fibrils, include neurodegenerative diseases such as scrapie, bovine spongiform encephalitis, Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. Another example is the treatment of traumatic brain injury. As another example, Loane, et al. report the targeting of amyloid precursor protein secretases as therapeutic targets for traumatic brain injury. (Loane et al., "Amyloid precursor protein secretases as therapeutic targets for traumatic brain injury", *Nature Medicine, Advance Online Publication*, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify inhibitors of BACE-1 and of other secretase enzyme inhibitors. Examples from the patent literature are growing and include US2005/0282826, WO2006009653, WO2007005404, WO02007005366, WO2007038271, WO2007016012, US2007072925, WO2007149033, WO2007145568, WO2007145569, WO2007145570, WO2007145571, WO2007114771, US20070299087, US2007/0287692, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, WO2009/131975, and WO2010/047372.

BACE inhibitors, particularly BACE-2 inhibitors, are an art-recognized target for the treatment of diabetes. Type 2 diabetes (T2D) is caused by insulin resistance and inadequate insulin secretion from the pancreatic beta-cells, leading to poor blood-glucose control and hyperglycemia (M Prentki & C J Nolan, "Islet beta-cell failure in type 2 diabetes." *J. Clin. Investig.*, 2006, 116(7), 1802-1812). Patients with T2D have an increased risk of microvascular and macrovascular disease and a range of related complications including diabetic neuropathy, retinopathy, and cardiovascular disease.

Beta-cell failure and consequent dramatic decline in insulin secretion and hyperglycemia marks the onset of T2D M Prentki & C J Nolan, "Islet beta-cell failure in type 2 diabetes." *J. Clin. Investig.*, 2006, 116(7), 1802-1812). Most current treatments do not prevent the loss of beta-cell mass characterizing overt T2D. However, recent developments with GLP-1 analogues, gastrin and other agents show that prevention and proliferation of beta-cells is possible to achieve, leading to an improved glucose tolerance and slower progression to overt T2D. (L L. Baggio & D J. Drucker, "Therapeutic approaches to preserve islet mass in type 2 diabetes", *Annu. Rev. Med.* 2006, 57, 265-281.)

Tmem27 has been identified as a protein promoting beta-cell proliferation (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397) and insulin secretion (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Tmem27 is a 42 kDa membrane glycoprotein which is a constitutively shed from the surface of beta-cells, resulting from a degradation of the full-length cellular Tmem27. Over expression of Tmem27 in a transgenic mouse increases beta-cell mass and improves glucose tolerance in a DIO model of diabetes. (P. Akpinar, S. Juqajima, J. Krutzfeldt, M. Stoffel, "Tmem27: A cleaved and shed plasma membrane protein that stimulates pancreatic beta-cell proliferation", *Cell. Metab.* 2005, 2, 385-397; (K. Fukui, Q. Yang, Y. Cao, N. Takahashi et al., "The HNF-1 target Collectrin controls insulin exocytosis by SNARE complex formation", *Cell. Metab.* 2005, 2, 373-384.) Furthermore, siRNA knockout of Tmem27 in a rodent beta-cell proliferation assay (e.g., using INS1e cells) reduces the proliferation rate, indicating a role for Tmem27 in control of beta-cell mass.

In vitro, BACE-2 (but reportedly not BACE-1) cleaves a peptide based on the sequence of Tmem27. BACE-2 is a membrane-bound aspartyl protease and is colocalized with Tmem27 in rodent pancreatic beta-cells (G. Finzi, F. Franzi, C. Placidi, F. Acquati, et al., "BACE-2 is stored in secretory granules of mouse and rat pancreatic beta cells", *Ultrastruct. Palhol.* 2008, 32(6), 246-251). It is also known to be capable of degrading APP (I. Hussain, D. Powell, D. Howlett, G. Chapman, et al., "ASP1 (BACE2) cleaves the amyloid precursor protein at the beta-secretase site", *Mol. Cell. Neurosci.* 2000, 16, 609-619), IL-1 R2 (P. Kuhn, E. Marjaux, A. Imhof, B. De Strooper, et al., "Regulated intramembrane proteolysis of the interleukin-1 receitpro II by alpha-, beta-, and gamma-secretase", *J. Biol. Chem.,* 2007, 282(16), 11982-11995). Inhibition of BACE-2 is therefore proposed as a treatment for T2D with the potential to preserve and restore beta-cell mass and stimulate insulin secretion in pre-diabetic and diabetic patients. See, e.g., WO2010128058.

SUMMARY OF THE INVENTION

The present invention provides certain imino thiadiazine dioxide compounds compounds which are collectively or individually referred to herein as "compound(s) of the invention", as described herein. The compounds of the invention are inhibitors of BACE-1. In some embodiments, the compounds of the invention are inhibitors of BACE-2. The compounds of the present invention have been found, surprisingly and advantageously, to exhibit improved solution stability.

In one embodiment, the compounds of the invention have the structural Formula (I):

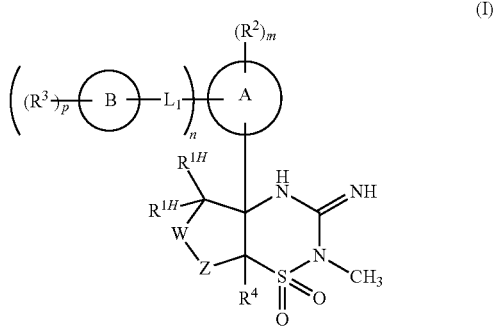

or its tautomeric form, Formula (I'):

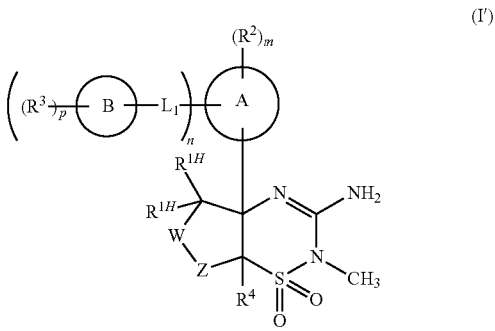

or pharmaceutically acceptable salt thereof, wherein:
one of W and Z is $C(R^{1H})_2$ and the other is $N(R^1)$;
ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;

each ring B (when present) is independently selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;
m, n, and p are each independently selected integers, wherein:
m is 0 or more;
n is 0 or 1; and
p is 0 or more,
wherein the maximum value of m is the maximum number of available substitutable hydrogen atoms on ring A, and wherein the maximum value of p is the maximum number of available substitutable hydrogen atoms on ring B;
-$L_1$- (when present) independently represents a bond or a divalent moiety selected from the group consisting of -alkyl-, -haloalkyl-, -heteroalkyl-, -alkenyl-, -alkynyl-, —$N(R^6)$—, —NHC(O)—, —C(O)NH—, $NHS(O)_2$—, —$S(O)_2NH$—, —O—$CH_2$, —$CH_2$—O—, —$NHCH_2$—, —$CH_2NH$—, and —$CH(CF_3)NH$—;
$R^1$ is selected from the group consisting of: H, —$C(O)R^6$, —$C(O)_2R^6$, —$C(O)N(R^6)_2$, —$C(=NOR^7)R^6$, —$S(O)R^6$, —$S(O)_2R^6$, —$S(O)_2N(R^6)_2$, alkyl, haloalkyl, heteroalkyl, alkenyl, alkynyl, phenyl, monocyclic heteroaryl, monocyclic cycloalkyl, and monocyclic heterocycloalkyl,
wherein said alkyl, said haloalkyl, said heteroalkyl, said alkenyl, said alkynyl, said phenyl, said monocyclic heteroaryl, said monocyclic cycloalkyl, and said monocyclic heterocycloalkyl of $R^1$ is optionally unsubstituted or substituted with one or more groups independently selected from $R^8$;
each $R^{1H}$ is independently selected from the group consisting of: H, halogen, —OH, —CN, —$SF_5$, —$OSF_5$, —$Si(R^5)_3$, —$N(R^6)_2$, —$NR^7C(O)R^6$, —$NR^7S(O)_2R^6$, —$NR^7C(O)N(R^6)_2$, —$NR^7C(O)OR^6$, —$OR^6$, —$SR^6$, —$C(O)R^6$, —$C(O)_2R^6$, —$C(O)N(R^6)_2$, —$P(O)(OR^5)_2$, —$P(O)(OR^5)(R^5)$, —$S(O)R^6$, —$S(O)_2R^6$, —$S(O)_2N(R^6)_2$, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, and -alkyl-(multicyclic group);
wherein said alkyl, said haloalkyl, said heteroalkyl, said alkenyl, said alkynyl, said aryl, said -alkyl-aryl, said monocyclic heteroaryl, said alkyl-(monocyclic heteroaryl), said monocyclic cycloalkyl, said -alkyl-(monocyclic cycloalkyl), said monocyclic heterocycloalkyl, said multicyclic group, and said -alkyl-(multicyclic group) of $R^{1H}$ is optionally unsubstituted or substituted with one or more groups independently selected from $R^8$;
each $R^2$ (when present) is independently selected from the group consisting of: halogen, —OH, —CN, —$SF_5$, —$OSF_5$, —$NO_2$, —$Si(R^5)_3$, —$P(O)(OR^5)_2$, —$P(O)(OR^5)(R^5)$, —$N(R^6)_2$, —$NR^7C(O)R^6$, —$NR^7S(O)_2R^6$, —$NR^7C(O)N(R^6)_2$, —$NR^7C(O)OR^6$, —$C(O)R^6$, —$C(O)_2R^6$, —$C(O)N(R^6)_2$, —$S(O)R^6$, —$S(O)_2R^6$, —$S(O)_2N(R^6)_2$, —$OR^6$, —$SR^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;
each $R^3$ (when present) is independently selected from the group consisting of: halogen, —OH, —CN, —$SF_5$, —$OSF_5$, —NO$_2$, —Si(R$^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of R$^2$ are each optionally unsubstituted or substituted with one or more groups independently selected from R$^8$;

R$^4$ is selected from the group consisting of H, halogen, optionally substituted alkyl, optionally substituted heteroalkyl, optionally substituted -alkyl-cycloalkyl, optionally substituted -alkyl-aryl, and optionally substituted -alkyl-heteroaryl, wherein said optional, substituents are each independently selected from R$^8$;

each R$^5$ (when present) is independently selected from the group consisting of H, alkyl, aryl, arylalkyl-, haloalkyl, cycloalkyl, -alkyl-cycloalkyl, heteroaryl, and heteroarylalkyl-;

each R$^6$ (when present) is independently selected from the group consisting of H, alkyl, alkenyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, aryl, -alkyl-aryl, heteroaryl, and -alkyl-heteroaryl, wherein each said aryl, -alkyl-aryl, heteroaryl, and -alkyl-heteroaryl of R$^6$ is unsubstituted or substituted with one or more groups independently selected from halogen, alkyl, heteroalkyl, haloalkyl, alkoxy, heteroalkoxy, and haloalkoxy;

each R$^7$ (when present) is independently selected from the group consisting of H, alkyl, cycloalkyl, -alkyl-cycloalkyl, aryl, -alkyl-aryl, heteroaryl, and -alkyl-heteroaryl; and each R$^8$ (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

In one embodiment, the compounds of the invention have the structural Formula (I) as described above.

In one embodiment, the compounds of the invention have the structural Formula (IA):

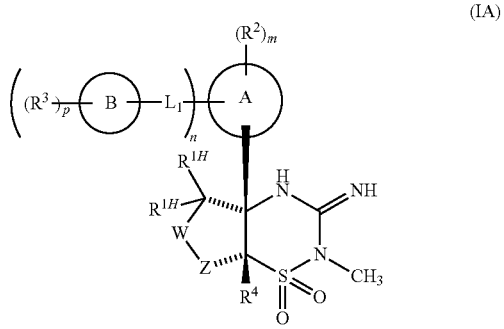

or its tautomeric form, Formula (IA'):

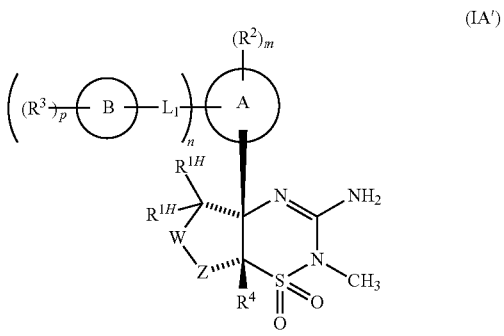

and include pharmaceutically acceptable salts thereof, wherein ring A, ring B, W, Z, -L$_1$-, R$^2$, R$^3$, R$^4$, m, n, and p are each defined in Formula (I).

In one embodiment, in each of Formulas (I), (I'), (IA), and (IA'):

W is N(R$^1$); and Z is C(R$^{1H}$)$_2$.

In one embodiment, in each of Formulas (I), (I'), (IA), and (IA'):

W is C(R$^{1H}$)$_2$ and Z is NR$^1$.

In one embodiment, in each of Formulas (I), (I'), (IA), and (IA'):

each R$^{1H}$ is independently selected from the group consisting of H, fluoro, methyl, ethyl, cyclopropyl, —CH$_2$-cyclopropyl, —OCH$_3$, —CH$_2$OH, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl, benzyl, —CH$_2$-pyridyl, —CH$_2$-pyrimidinyl, —CH$_2$-pyrazinyl;

wherein each said phenyl, pyridyl, pyrimidinyl, pyrazinyl, benzyl, —CH$_2$-pyridyl, —CH$_2$-pyrimidinyl, —CH$_2$-pyrazinyl of R$^1$ is unsubstituted or substituted with one or more groups independently selected from the group consisting of halogen, alkyl, cycloalkyl, heteroalkyl, alkoxy, —O-cycloalkyl, and haloalkyl.

In one embodiment, in each of Formulas (I), (I'), (IA), and (IA'):

each R$^{1H}$ is independently selected from the group consisting of H, methyl, ethyl, cyclopropyl, —CH$_2$-cyclopropyl, —CH$_2$OH, —CH$_2$OCH$_3$, —CH$_2$OCH$_2$CH$_3$, trifluoromethyl, —CH$_2$F, —CHF$_2$, phenyl, pyridyl, pyrimidinyl, pyrazinyl;

wherein each said phenyl, pyridyl, pyrimidinyl, pyrazinyl of $R^1$ is unsubstituted or substituted with one or more groups independently selected from the group consisting of halogen, alkyl, cycloalkyl, heteroalkyl, alkoxy, —O-cycloalkyl, and haloalkyl.

In one embodiment, in each of Formulas (I), (I'), (IA), and (IA'):

each $R^{1H}$ is independently selected from the group consisting of H, methyl, cyclopropyl, —CH$_2$OH, —CH$_2$OCH$_3$-trifluoromethyl, —CH$_2$F, —CHF$_2$.

In one embodiment, in each of Formulas (I), (I'), (IA), and (IA'):

each $R^{1H}$ is H.

In one embodiment, the compounds of the invention have the structural Formula (II):

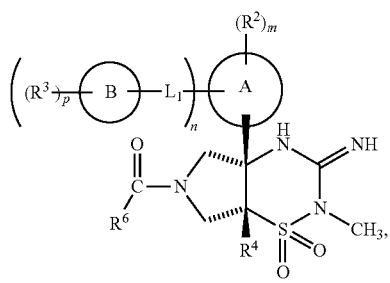
(II)

or its tautomeric form, Formula (II'):

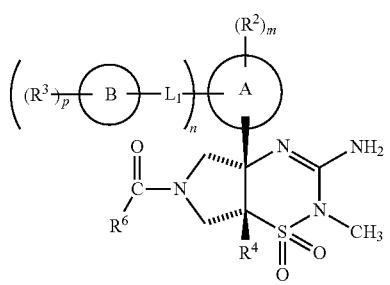
(II')

and include pharmaceutically acceptable salts thereof, wherein:

$R^6$ is selected from the group consisting of H, alkyl, alkenyl, -heteroalkyl, haloalkyl, cycloalkyl, cycloalkylalkyl-, aryl, and heteroaryl; and ring A, ring B, -L$_1$-, $R^2$, $R^3$, $R^4$, m, n, and p are each as defined in Formula (I).

In one embodiment, in each of Formulas (II) and (II'), $R^6$ is lower alkyl.

In one embodiment, in each of Formulas (II) and (II), $R^6$ is selected from the group consisting of methyl and ethyl.

In one embodiment, in each of Formulas (II) and (II'), $R^6$ is methyl.

In one embodiment, the compounds of the invention have the structural Formula (III):

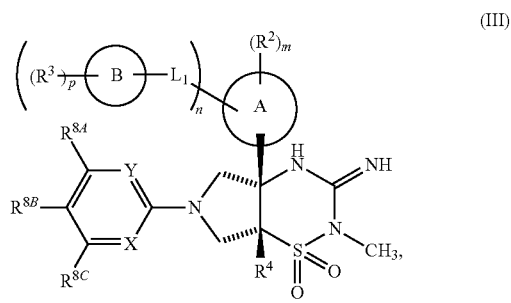
(III)

or its tautomeric form, Formula (III'):

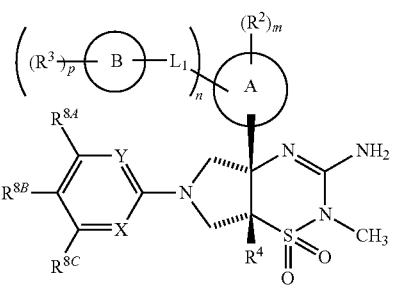
(III')

and include pharmaceutically acceptable salts thereof, wherein:

X is N or CH;
Y is N or CH;
$R^{8A}$, $R^{8B}$, and $R^{8C}$ are each independently selected from the group consisting of H, fluorine, chlorine, lower alkyl, lower alkoxy, lower haloalkyl, lower haloalkoxy, lower alkyl-OH, cycloalkyl, -alkyl-cycloalkyl, —O-cycloalkyl, —O-alkyl-cycloalkyl, lower heteroalkyl, and lower —O-heteroalkyl;

and ring A, ring B, -L$_1$-, $R^2$, $R^3$, m, n, and p are each as defined in Formula (I).

In another embodiment, in each of Formulas (III) and (III'):
X is N; and
Y is N.

In another embodiment, in each of Formulas (III) and (III'):
X is N; and
Y is CH.

In another embodiment, in each of Formulas (III) and (III'):
X is CH; and
Y is N.

In another embodiment, in each of Formulas (III) and (III'):
X is CH; and
Y is CH.

In another embodiment, in each of Formulas (III) and (III'):
$R^{8A}$ is selected from lower alkyl, lower alkoxy, lower haloalkyl, lower heteroalkyl, cyclopropyl, and -loweralkyl-cyclopropyl;
$R^{8B}$ is selected from H, fluorine and chlorine; and
$R^{8C}$ is selected from lower alkyl, lower alkoxy, lower haloalkyl, lower heteroalkyl, cyclopropyl, and -loweralkyl-cyclopropyl.

In another embodiment, in each of Formulas (III) and (III'):
$R^{8A}$ is selected from methyl, ethyl, isopropyl, cyclopropyl, cyclobutyl, difluoromethyl, 1,1-difluoroethyl, 2,2,2-trifluoroethyl, —O—CH$_3$, —O—CH$_2$CH$_3$, —(CH$_2$)—O—CH$_3$, and —CH$_2$—O—CH$_2$—CH$_3$;
$R^{8B}$ is selected from H, fluorine and chlorine; and $R^{8C}$ is selected from methyl, ethyl, isopropyl, cyclopropyl, cyclobutyl, difluoromethyl, 1,1-difluoroethyl, 2,2,2-trifluoroethyl, —O—CH$_3$, —O—CH$_2$CH$_3$, —(CH$_2$)—O—CH$_3$, and —CH$_2$—O—CH$_2$—CH3.
Non-limiting examples, in Formula (III) and (III'), of the moiety
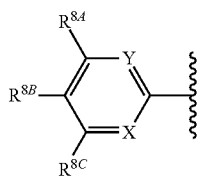
include
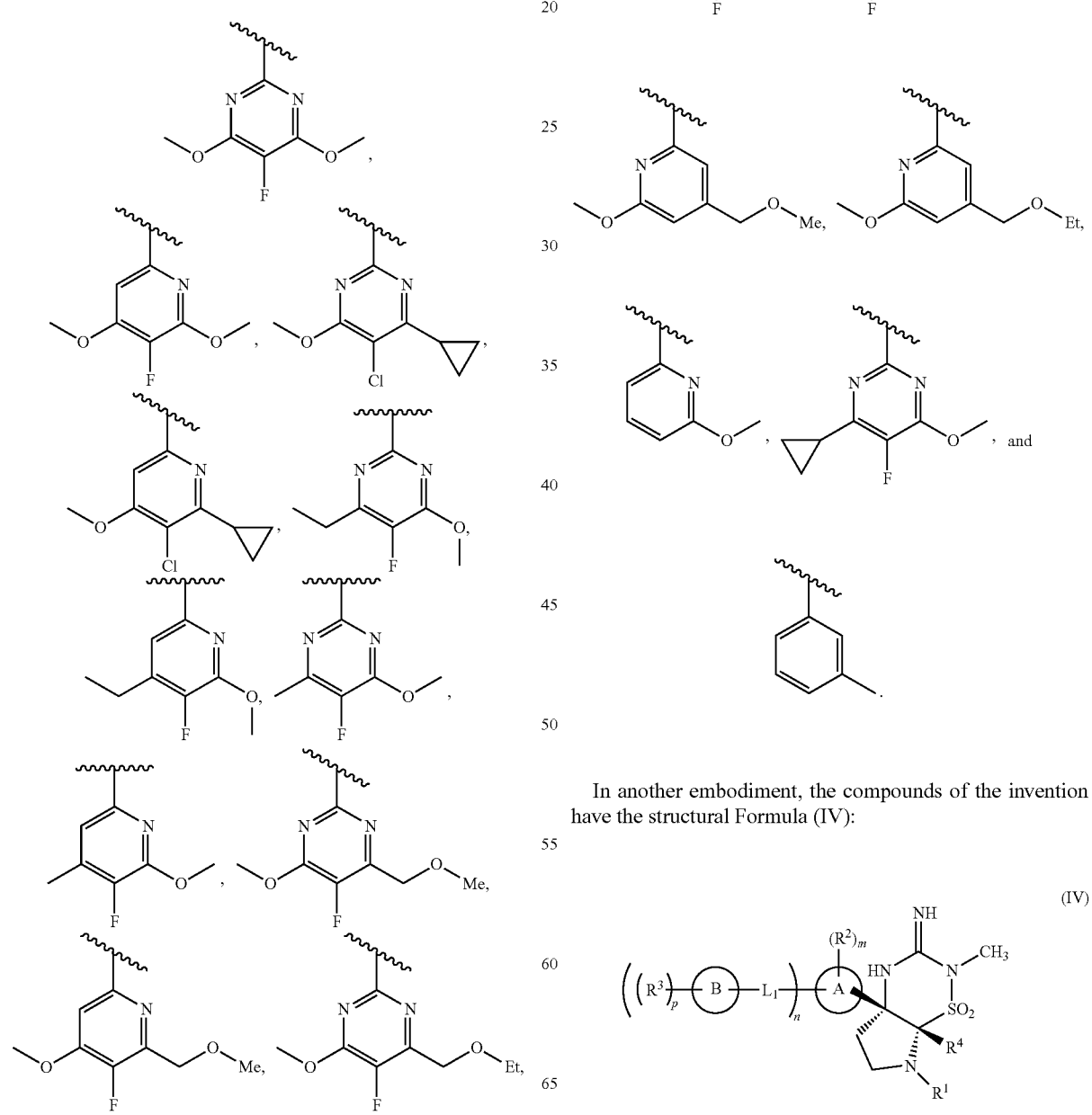
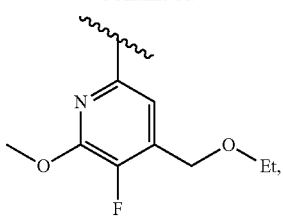
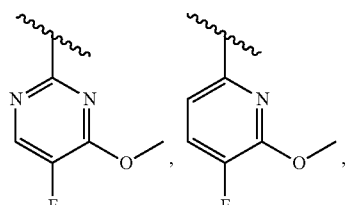
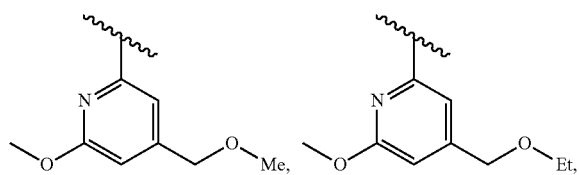
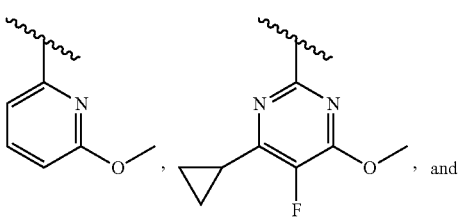
and
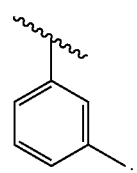
In another embodiment, the compounds of the invention have the structural Formula (IV):
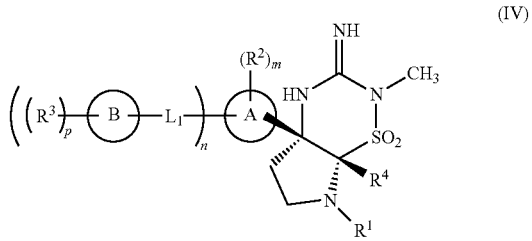
(IV)

or a tautomer thereof having the structural Formula (VI'):

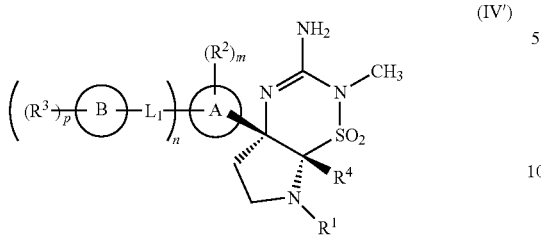
(IV')

or pharmaceutically acceptable salt thereof, wherein:

$R^1$ is selected from the group consisting of: H, —C(O)$R^6$, alkyl, cycloalkyl, haloalkyl, heteroalkyl, aryl, monocyclic heteroaryl, wherein said alkyl, said haloalkyl, said heteroalkyl, said aryl, said monocyclic heteroaryl of $R^1$ is optionally unsubstituted or substituted with one or more groups independently selected from $R^8$; and ring A, ring B, -$L_1$-, $R^2$, $R^3$, $R^4$, m, n, and p are each as defined in Formula (I).

In another embodiment, in each of Formulas (I), (I'), (IA), (IA'), (IV), and (IV'):

each $R^1$ is independently selected from the group consisting of: H, —C(O)(lower alkyl), lower alkyl, lower cycloalkyl, haloalkyl, heteroalkyl, phenyl, pyridyl, pyrimidinal, and pyrazinyl, wherein said lower alkyl, lower cycloalkyl, heteroalkyl, phenyl, pyridyl, pyrimidinal, and pyrazinyl of $R^1$ is optionally unsubstituted or substituted with one or more groups independently selected from $R^8$.

In another embodiment, in each of Formulas (I), (I'), (IA), (IA'), (IV), and (IV'):

each $R^1$ is independently selected from the group consisting of: H, —C(O)CH$_3$, —C(O)cyclopropyl, —C(O)—CH$_2$cyclopropyl, phenyl, methyl, ethyl, and —CH$_2$CF$_3$.

In one embodiment, in each of Formulas (I), (I'), (IA), (IA'), (II), (II'), (III), (III'), (IV), and (IV'), $R^4$ is selected from the group consisting of H, fluoro, methyl, ethyl, —CH$_2$-cyclopropyl, benzyl, —CH$_2$-pyridyl, —CH$_2$OCH$_3$ and —CH$_2$OCH$_2$CH$_3$, wherein said benzyl and said —CH$_2$-pyridyl of $R^4$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In another embodiment, in each of Formulas (I), (I'), (IA), (IA'), (II), (II'), (III), (III'), (IV), and (IV'):

$R^4$ is selected from the group consisting of H, fluoro, methyl, —CH$_2$-cyclopropyl, and —CH$_2$OCH$_3$.

In another embodiment, in each of Formulas (I), (I'), (IA), (IA'), (II), (II'), (III), (III'), (IV), and (IV'):

$R^4$ is H.

In another embodiment, in each of Formulas (I), (I'), (IA), (IA'), (II), (II'), (III), (III'), (IV), and (IV'):

$R^4$ is selected from the group consisting of H, lower alkyl, and —CH$_2$-cyclopropyl.

In some embodiments, in each of Formulas (I), (I'), (IA), (IA'), (II), (II'), (III), (III'), (IV), and (IV'), n is 0. In these embodiments, the moiety:

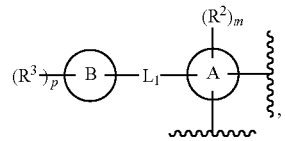

has the form

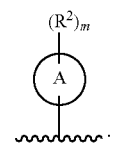

In another embodiment, in each of Formulas (I), (I'), (IA), (IA'), (II), (II'), (III), (III'), (IV), and (IV'):

n is 0;

ring A is selected from the group consisting of phenyl, pyridyl, pyrazinyl, furanyl, thienyl, pyrimidinyl, pyridazinyl, thiazolyl, and oxazolyl; and $R^2$ and m are each as defined in Formula (I).

In another embodiment, in each of Formulas (I), (I'), (IA), (IA'), (II), (II'), (III), (III'), (IV), and (IV'):

n is 0;

ring A is selected from the group consisting of phenyl, pyridyl, pyrazinyl, furanyl, thienyl, pyrimidinyl, pyridazinyl, thiazolyl, and oxazolyl;

m is 0 to 5; and each $R^2$ (when present) is independently selected from the group consisting of halogen, —OH, —CN, —SF$_5$, —OSF$_5$, —NO$_2$, —N($R^6$)$_2$, —N$R^7$C(O)$R^6$, —N$R^7$S(O)$_2$$R^6$, —N$R^7$C(O)N($R^6$)$_2$, —N$R^7$C(O)O$R^6$, —C(O)$R^6$, —C(O)$_2$$R^6$, —C(O)N($R^6$)$_2$, —S(O)$R^6$, —S(O)$_2$$R^6$, —S(O)$_2$N($R^6$)$_2$, —O$R^6$, —S$R^6$, lower alkyl, -(lower alkyl)-OH, lower haloalkyl, lower heteroalkyl, lower alkenyl, lower alkynyl, phenyl, benzyl, lower cycloalkyl, monocyclic heteroaryl, and —CH$_2$-(monocyclic heteroaryl), wherein said phenyl, benzyl, lower cycloalkyl, monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In one such embodiment, each $R^6$ (when present) is independently selected from the group consisting of H, lower alkyl, lower haloalkyl, and lower heteroalkyl, and $R^7$ (when present) is selected from the group consisting of H, lower alkyl.

In another embodiment, in each of Formulas (I), (I'), (IA), (IA'), (II), (II'), (III), (III'), (IV), and (IV'):

n is 0;

ring A is selected from the group consisting of phenyl, pyridyl, and thienyl; and $R^2$ and m are each as defined in Formula (I).

In another embodiment, in each of Formulas (I), (I'), (IA), (IA'), (II), (II'), (III), (III'), (IV), and (IV'):

n is 0;

ring A is phenyl; and $R^2$ and m are each as defined in Formula (I).

In another embodiment, in each of Formulas (I), (I'), (IA), (IA'), (II), (II'), (III), (III'), (IV), and (IV'):

n is 0;

ring A is phenyl;

m is 0 to 5; and each $R^2$ (when present) is independently selected from the group consisting of halogen, —CN, —$SF_5$, —$OSF_5$, —$NO_2$, —$NH_2$, —N(alkyl)$_2$, —NH(alkyl), —NHC(O)$R^6$, —NHS(O)$_2R^6$, —NHC(O)N($R^6$)$_2$, —NHC(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, lower alkyl, lower haloalkyl, lower heteroalkyl, lower alkenyl, lower alkynyl, phenyl, benzyl, lower cycloalkyl, monocyclic heteroaryl, and —$CH_2$-(monocyclic heteroaryl), wherein said phenyl, benzyl, lower cycloalkyl, monocyclic heteroaryl, and —$CH_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —$SF_5$, and —$OSF_5$.

In one such embodiment, each $R^6$ (when present) is independently selected from the group consisting of H, lower alkyl, lower haloalkyl, lower cycloalkyl, and lower heteroalkyl.

In another embodiment, in each of Formulas (I), (I'), (IA), (IA'), (II), (II'), (III), (III'), (IV), and (IV'):

n is 0;

ring A is phenyl;

m is 0 to 4; and each $R^2$ group (when present) is independently selected from the group consisting of halogen, —CN, —$SF_5$, —$NH_2$, —$NHCH_3$, —N($CH_3$)$_2$, —$OCH_3$, —$OCH_2CH_3$, —O-cyclopropyl, —S($CH_3$), methyl, ethyl, propyl, cyclopropyl, —$CH_2$-cyclopropyl, —C≡C—$CH_3$, —$CF_3$, —$CHF_2$, —C(O)OH, —C(O)O$CH_3$, —C(O)O$CH_2CH_3$, —O$CF_3$, and —$OCHF_2$.

In another embodiment, in each of Formulas (I), (I'), (IA), (IA'), (II), (II'), (III), (III'), (IV), and (IV'):

n is 0;

ring A is phenyl;

m is 0 to 4; and each $R^2$ group (when present) is independently selected from the group consisting of halogen, haloalkyl, cyclopropyl, and —CN.

In another embodiment, in each of Formulas (I), (I'), (IA), (IA'), (II), (II'), (III), (III'), (IV), and (IV'):

n is 0;

ring A is phenyl;

m is 0 to 4; and each $R^2$ group (when present) is independently selected from the group consisting of fluorine, chlorine, bromo, cyclopropyl, —$CF_3$, and —CN.

Non-limiting examples, in each of Formulas (I), (I'), (IA), (IA'), (II), (II'), (III), (III'), (IV), and IV'), when n is 0, of the moiety

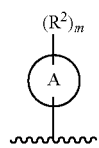

include:

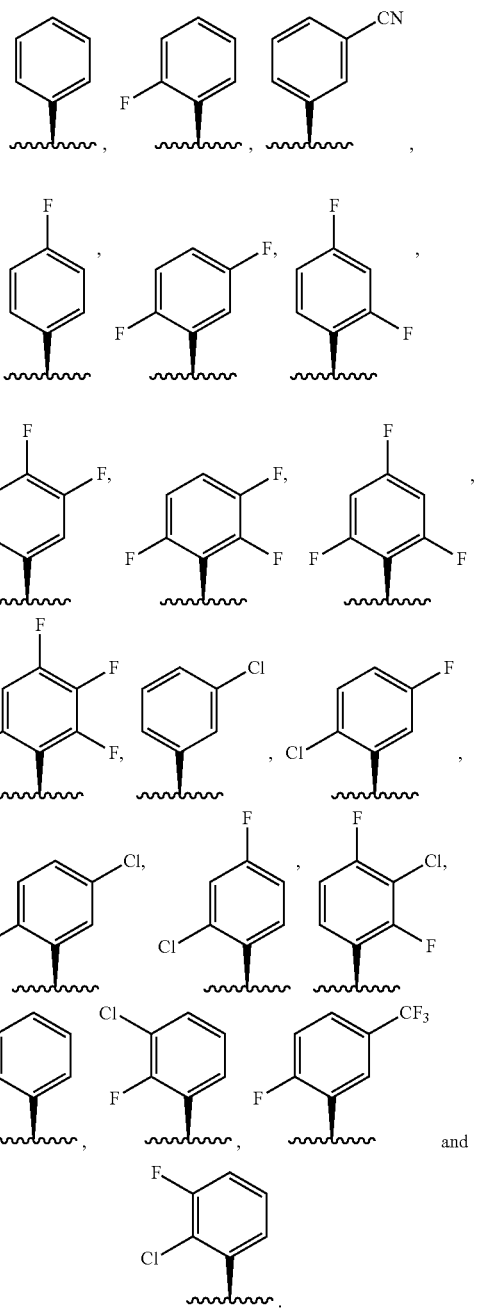

Additional non-limiting examples, in each of Formulas (I), (I'), (IA), (IA'), (II), (II'), (III), (III'), (IV), and (IV'), when n is 0, of the moiety

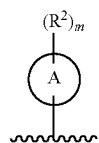

include:

[chemical structures of various substituted thiophene groups]

In some embodiments, in each of Formulas (I), (I'), (IA), (IA'), (II), (II'), (III), (III'), (IV), (IV'), (V), (V'), (VI) and (VI'):

n is 1. In these embodiments, the moiety:

[structural formula with (R³)$_p$—B—L$_1$—A—(R²)$_m$]

has the form:

[structural formula with (R³)$_p$—B—L$_1$—A—(R²)$_m$]

In another embodiment, in each of Formulas (I), (I'), (IA), (IA'), (II), (II'), (III), (III'), (IV), (IV'), (V), (V'), (VI) and (VI'):
n is 1;
m is 0 or more; and
ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, and thienopyrazolyl.

In another embodiment, in each of Formulas (I), (I'), (IA, (IA'), (II), (II'), (III), (III'), (IV), (IV'), (V), (V'), (VI) and (VI'):
n is 1;
m is 0 or more; and
ring A is selected from the group consisting of phenyl, pyridyl, thienyl, thiazolyl, naphthyl, isoquinolinyl, benzothienyl, benzimidazolyl, indazolyl, indolyl, and thienopyrazolyl.

In another embodiment, in each of Formulas (I), (I'), (LA), (IA'), (II), (II'), (III), (III'), (IV), (IV'), (V), (V'), (VI) and (VI)':
n is 1;
m is 0 or more; and
ring A is selected from the group consisting of phenyl, thienyl, and pyridyl.

In another embodiment, in each of Formulas (I), (I'), (IA), (IA'), (II), (II'), (III), (III'), (IV), (IV'), (V), (V'), (VI) and (VI'):
n is 1;
m is 0 or more; and
each R² (when present) is independently selected from the group consisting of halogen, —CN, —SF$_5$, —OSF$_5$, —NO$_2$, —NH$_2$, —N(alkyl)$_2$, —NH(alkyl), —NHC(O)R⁶, —NHS(O)$_2$R⁶, —NHC(O)N(R⁶)$_2$, —NHC(O)OR⁶, —C(O)R⁶, —C(O)$_2$R⁶, —C(O)N(R⁶)$_2$, —S(O)R⁶, —S(O)$_2$R⁶, —S(O)$_2$N(R⁶)$_2$, —OR⁶, —SR⁶, lower alkyl, lower haloalkyl, lower heteroalkyl, lower alkenyl, lower alkynyl, phenyl, benzyl, lower cycloalkyl, monocyclic heteroaryl, and —CH$_2$-(monocyclic heteroaryl),
wherein said phenyl, benzyl, lower cycloalkyl, monocyclic heteroaryl, and —CH$_2$-(monocyclic heteroaryl) of R² is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In one such embodiment, each R⁶ (when present) is independently selected from the group consisting of H, lower alkyl, lower cycloalkyl, lower haloalkyl, and lower heteroalkyl.

In another embodiment, in each of Formulas (I), (I'), (IA), (IA'), (II), (II'), (III), (III'), (IV), (IV'), (V), (V'), (VI) and (VI'):
n is 1;
m is 0 or more; and
each R² group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

In another embodiment, in each of Formulas (I), (I'), (IA), (IA'), (II), (II'), (III), (III'), (IV), (IV'), (V), (V'), (VI) and (VI'):
n is 1;
m is 0, 1, or 2; and
each R² group (when present) is independently selected from F, Cl, Br, —CN, —CF$_3$, —CHF$_2$, cyclopropyl, —OCF$_3$, and —OCHF$_2$.

In another embodiment, in each of Formulas (I), (I'), (IA), (IA'), (II), (II'), (III), (III'), (IV), and (IV'):

n is 1;

ring A is selected from the group consisting of phenyl, thienyl, and pyridyl;

m is 0, 1, or 2; and each $R^2$ group (when present) is independently selected from the group consisting F, Cl, Br, —CN, —$CF_3$, —$CHF_2$, cyclopropyl, —$OCF_3$, and —$OCHF_2$.

In another embodiment, in each of Formulas (I), (I'), (IA), (IA'), (II), (II'), (III), (III'), (IV), and (IV'):

n is 1; and

-$L_1$- represents a bond or a divalent moiety selected from the group consisting of —NHC(O), —C(O)NH—, —NHS(O)$_2$—, —S(O)$_2$NH—, —O—CH$_2$—, —CH$_2$—O—, —NHCH$_2$—, —CH$_2$NH—, and —CH(CF$_3$)NH—.

In another embodiment, in each of Formulas (I), (I'), (IA), (IA'), (II), (II'), (III), (III'), (IV), and (IV'):

n is 1; and

-$L_1$- represents a bond or a divalent moiety selected from the group consisting of —NHC(O)— and —C(O)NH—.

In another embodiment, in each of Formulas (I), (I'), (IA), (IA'), (II), (II'), (III), (III'), (IV), and (IV'):

n is 1; and

-$L_1$- represents a bond.

In another embodiment, in each of Formulas (I), (I'), (IA), (IA'), (II), (II'), (III), (III'), (IV), and (IV'):

n is 1; and

-$L_1$- represents a divalent moiety selected from the group consisting of —NHC(O)— and —C(O)NH—.

In another embodiment, in each of Formulas (I), (I'), (IA), (IA'), (II), (II'), (III), (III'), (IV), and (IV'):

n is 1;

p is 0 or more; and ring B is selected from the group consisting of phenyl, monocyclic heterocycloalkyl, monocyclic heteroaryl, and a multicyclic group.

In another embodiment, in each of Formulas (I), (I'), (IA), (IA'), (II), (II'), (III), (III'), (IV), and (IV'):

n is 1;

p is 0 or more; and ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl.

In another embodiment, in each of Formulas (I), (I'), (IA), (IA'), (II), (II'), (III), (III'), (IV), and (IV'):

n is 1;

p is 0 or more; and ring B is selected from the group consisting of phenyl, pyridinyl, pyrimidinyl, oxazolyl, pyrrolyl, and a multicyclic group.

In another embodiment, in each of Formulas (I), (I'), (IA), (IA'), (II), (II'), (III), (III'), (IV), and (IV'):

n is 1;

p is 0 or more; and ring B is selected from the group consisting of phenyl, pyridinyl, pyrimidinyl, oxazolyl, pyrrolyl, and indolyl.

In another embodiment, in each of Formulas (I), (I'), (IA), (IA'), (II), (I'), (III), (III'), (IV), and (IV'):

n is 1;

p is 0 or more; and each $R^3$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, monocyclic heteroaryl, and —CH$_2$-(monocyclic heteroaryl), wherein said phenyl, benzyl, lower cycloalkyl, monocyclic heteroaryl, and —CH$_2$-(monocyclic heteroaryl) of R$^3$ is unsubstituted or substituted with one or more groups independently selected from the group consisting of halogen, alkyl, heteroalkyl, haloalkyl, alkoxy, —O-cyclopropyl, heteroalkoxy, haloalkoxy, —CN, —SF$_5$, and —OSF$_5$.

In one such embodiment, each R$^6$ (when present) is independently selected from the group consisting of H, lower alkyl, lower cycloalkyl, lower haloalkyl, and lower heteroalkyl.

In another embodiment, in each of Formulas (I), (I'), (IA), (IA'), (II), (II'), (III), (III'), (IV), and (IV'):

n is 1;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), and (IV'):

n is 1;

ring A is selected from the group consisting of phenyl, thienyl, and pyridyl;

m is 0 or 1;

each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-$L_1$- is a bond or a divalent moiety selected from the group consisting of —NHC(O)— and —C(O)NH—;

ring B is selected from the group consisting of phenyl, monocyclic heterocycloalkyl, and monocyclic heteroaryl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (I'), (IA), (IA'), (II), (II'), (III), (III'), (IV), and (IV'):

n is 1; ring A is phenyl or pyridyl; and the moiety

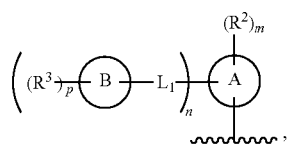

has the form:

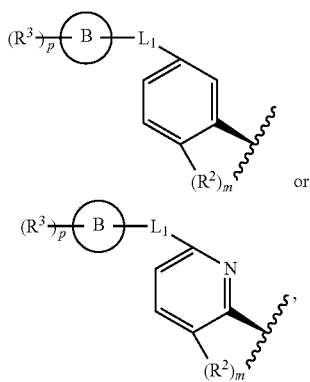

wherein:
m is 0 or 1;
each R² group (when present) is independently selected from the group consisting of halogen, —CN, —SF₅, —NHCH₃, —N(CH₃)₂, —OCH₃, —OCH₂CH₃, —O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, and —OCHF₂;

-L₁- is a bond or a divalent moiety selected from the group consisting of —NHC(O)— and —C(O)NH—;
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and
each R³ group (when present) is independently selected from the group consisting of halogen, —OH, —CN, —SF₅, —NH₂, —NH(CH₃), —N(CH₃)₂, —OCH₃, —OCH₂CH₃, O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, —OCH₂CF₃, and —OCHF₂.

In another embodiment, in each of Formulas (I), (I'), (IA), (IA'), (II), (II'), (III), (III'), (IV), (IV'), (V), (V'), (VI) and (VI'):
n is 1; ring A is thienyl; and the moiety

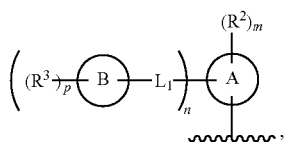

as the form:

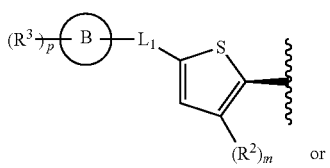

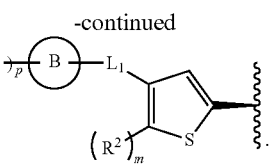

wherein:
m is 0 or 1;
each R² group (when present) is independently selected from the group consisting of halogen, —CN, —SF₅, —NHCH₃, —N(CH₃)₂, —OCH₃, —OCH₂CH₃, —O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, and —OCHF₂.

-L₁- is a bond or a divalent moiety selected from the group consisting of —NHC(O)— and —C(O)NH—;
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, and isothiazolyl;

p is 0 or more; and
each R³ group (when present) is independently selected from the group consisting of halogen, —OH, —CN, —SF₅, —NH₂, —NH(CH₃), —N(CH₃)₂, —OCH₃, —OCH₂CH₃, O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, —OCH₂CF₃, and —OCHF₂.

In another embodiment, in each of Formulas (I), (I'), (IA), (IA'), (II), (II'), (III), (III'), (IV), (IV'), (V), (V'), (VI) and (VI'), n is 1, and the moiety

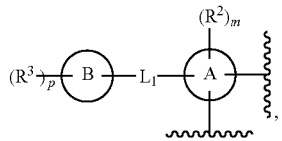

is selected from the group consisting of:

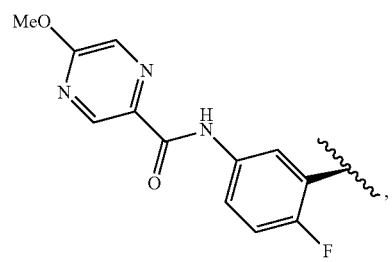

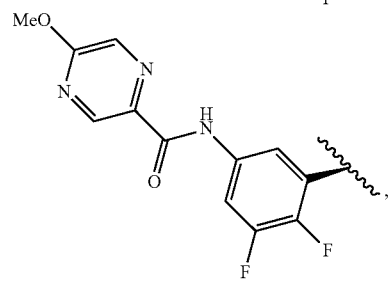

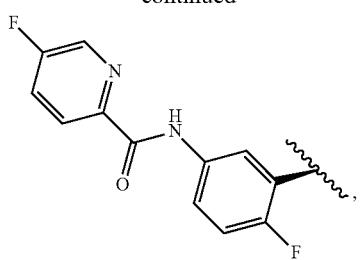
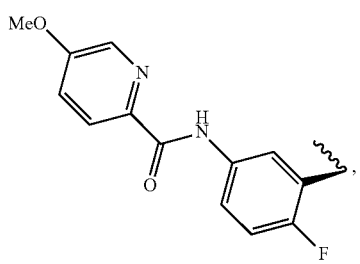
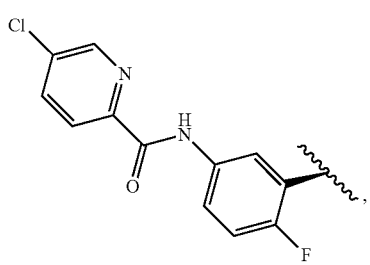
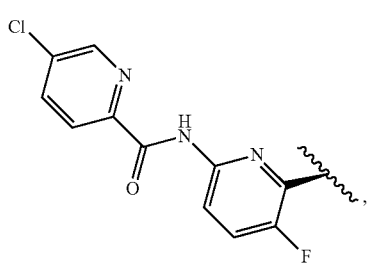
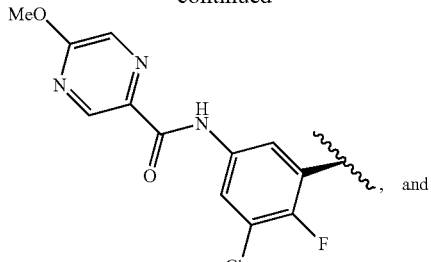
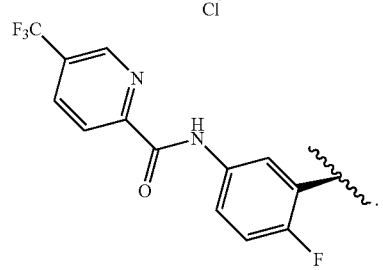
In another embodiment, in each of Formulas (I), (I'), (IA), (IA'), (II), (II'), (III), (III'), (IV), and (IV'), n is 1 and the moiety
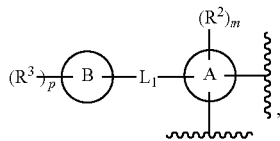
is selected from the group consisting of:
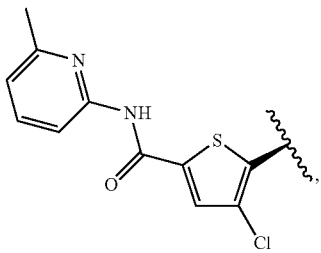
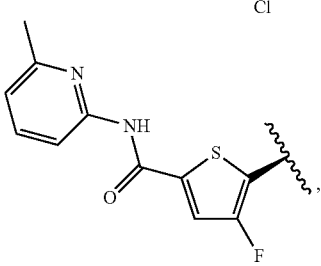
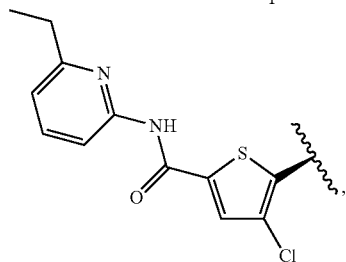

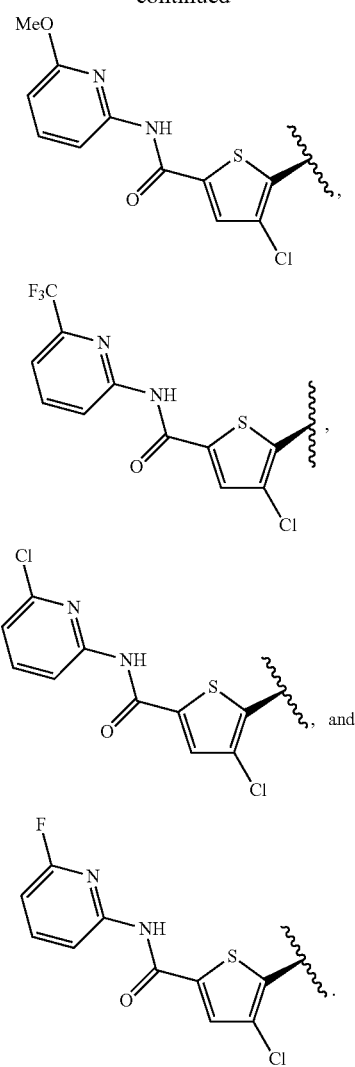

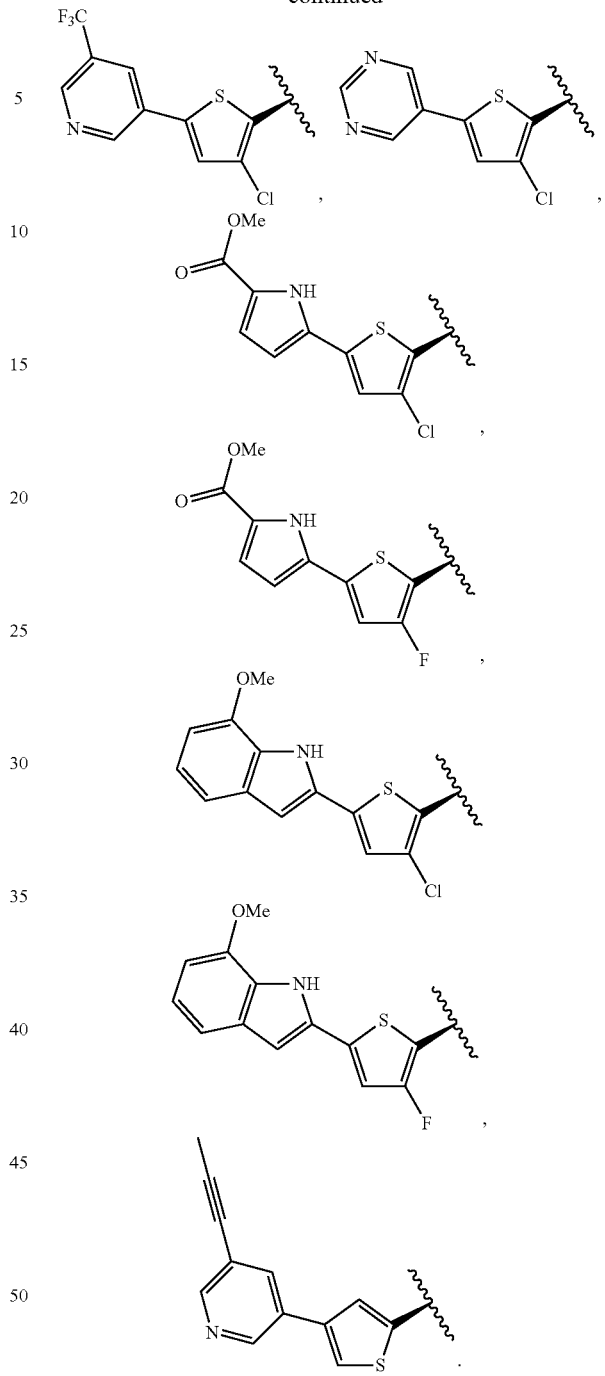

In another embodiment, in each of Formulas (I) (I'), (IA), (IA') (II), (II'), (III), (III'), (IV), and (IV'), n is 1, -L₁- is a bond, and the moiety

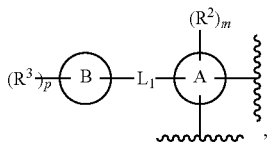

is selected from the group consisting of:

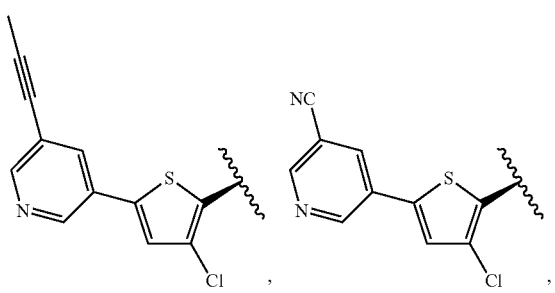

Specific non-limiting examples of compounds of the invention are shown in Table 4 below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents for use in combination with the compounds of the invention include those selected from the group consisting of: (a) drugs useful for the treatment of Alzheimer's disease and/or drugs useful for treating one or more symptoms of Alzheimer's disease, (b) drugs useful for inhibiting the synthesis Aβ, (c) drugs useful for treating neurodegenerative diseases, and (d) drugs useful for the treatment of type II diabetes and/or one or more symptoms or associated pathologies thereof.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, Cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase (BACE-1 and/or BACE-2) comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro.

Another embodiment provides a method of inhibiting β-secretase in a patient in need thereof. Another embodiment provides a method of inhibiting the formation of Aβ from APP in a patient in need thereof. Another embodiment, the invention provides a method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

As described herein, variables of the formulas presented herein, such as ring A and ring B may be unsubstituted or substituted with "one or more" groups. For example, ring A may be unsubstituted or substituted with one or more $R^2$ groups; ring B may be unsubstituted or substituted with one or more $R^3$ groups. It shall be understood that the upper limit of the number of substituents (referred to in the phrase "one or more substituents") is the number of available hydrogen atoms on the relevant moiety (e.g., ring A or ring B) that are available for replacement by a substituent which will result in a chemically stable and chemically neutral moiety. Thus, for example, in the various Formulas of the compounds of the invention, e.g., in Formula (I), m, n, and p are each independently selected integers, wherein:

m is 0 or more,
n is 0 or 1, and
p is 0 or more, wherein the maximum value of m is the maximum number of available substitutable hydrogen atoms on ring A, and wherein the maximum value of p is the maximum number of available substitutable hydrogen atoms on ring B. By way of non-limiting illustration, when ring A is a

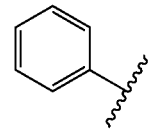

group, the maximum value of m is 5. When ring A is a

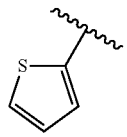 [SMILES: *c1cccs1]

group, the maximum value of m is 3. When ring A is a

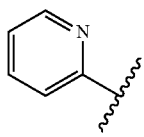

group, the maximum value of m is 4.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

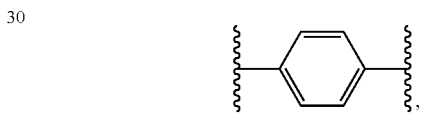

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—:

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

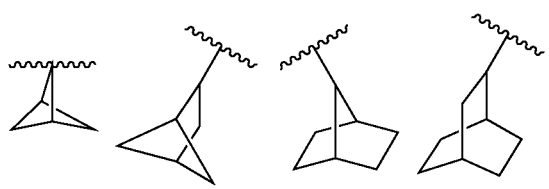

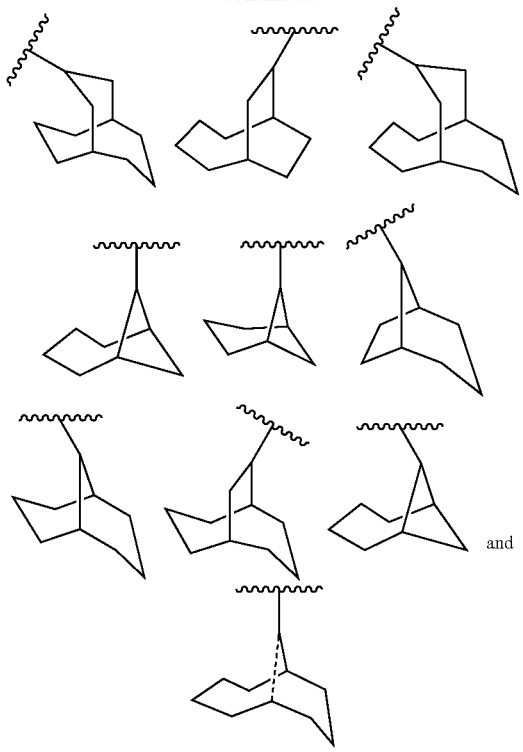

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide.

"Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

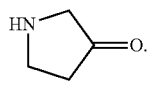

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

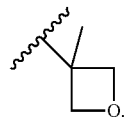

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

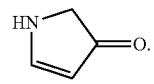

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N,N-oxide, O, S, S-oxide, S(O), and S(O)$_2$. The point of attachment to the parent moiety is to any available ring carbon or ring heteroatom. Non-limiting examples of monocyclic heterocyloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

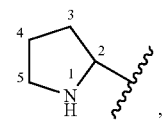

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

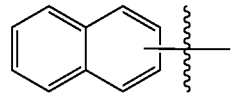

The term multicyclic groups includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof. Non-limiting examples of multicyclic groups which are bicyclic heteroaromatic groups comprising from 1 to 3 ring heteroatoms, each said ring heteroatom being independently selected from N, O, and S include the following, and oxides thereof:
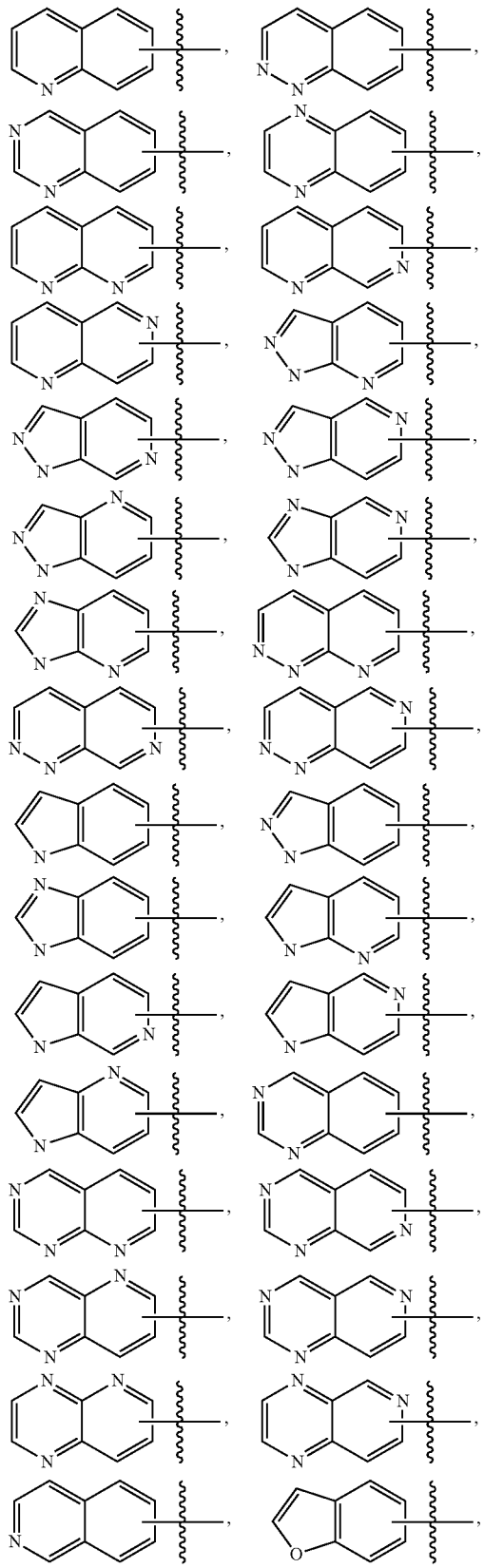
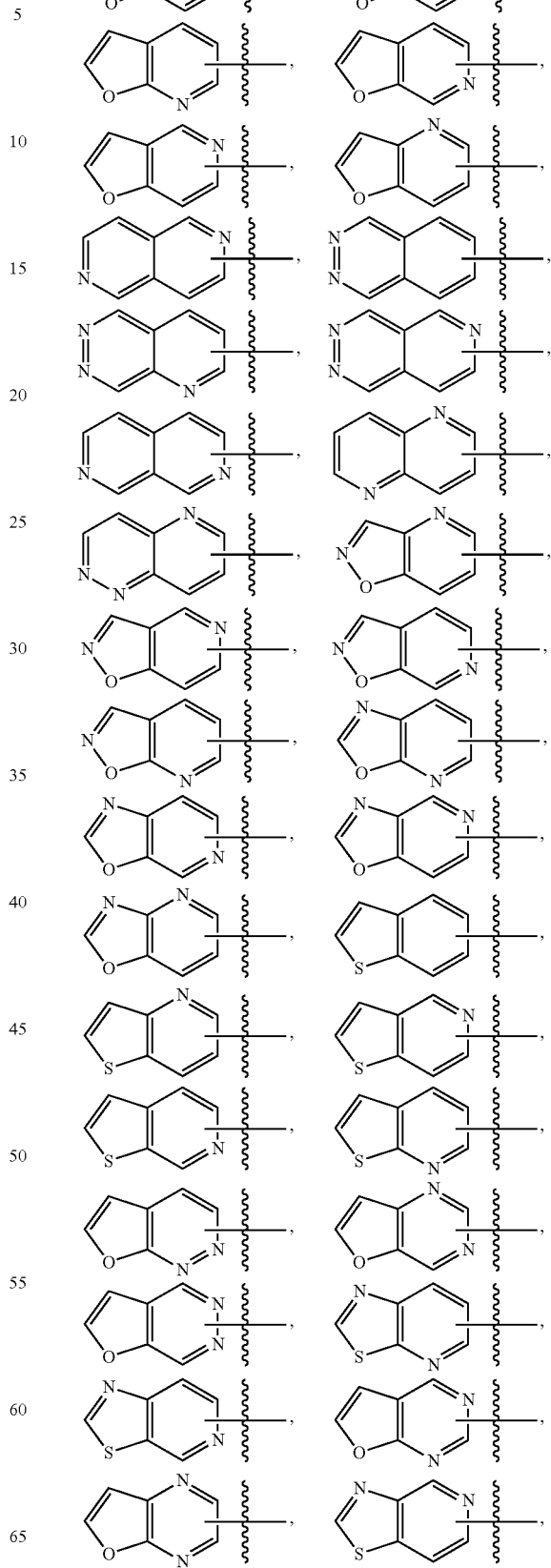

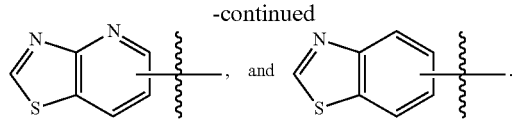, and

The term multicyclic group includes saturated bicyclic cycloalkyl groups. Non-limiting examples of multicyclic groups which are saturated bicyclic cycloalkyl groups include the following:

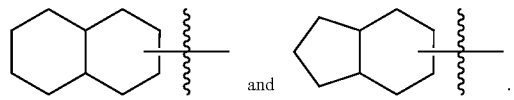

The term multicyclic group includes partially unsaturated bicyclic cycloalkyl groups. Non-limiting examples of multicyclic groups which comprise partially unsaturated bicyclic cycloalkyl groups include the following:

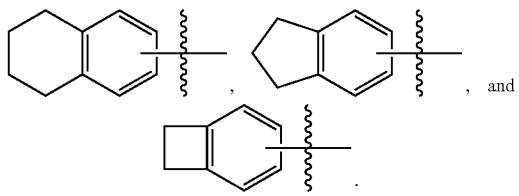

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S. Non-limiting examples of multicyclic groups which are partially or fully saturated bicyclic groups comprising from 1 to 3 ring heteroatoms, each said ring heteroatom being independently selected from N, O, and S include the following, and oxides thereof:

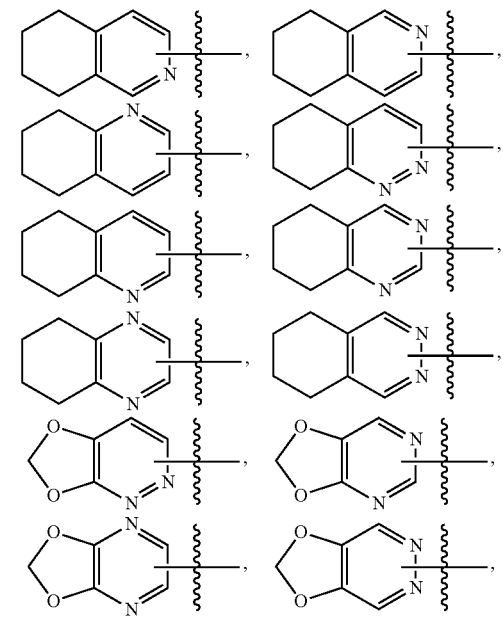

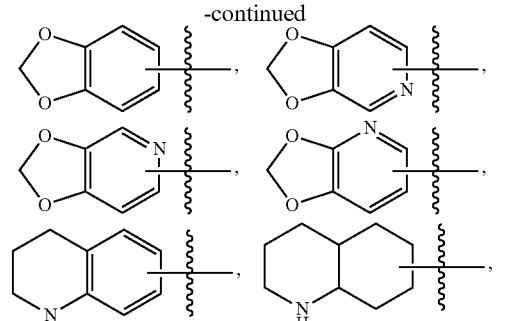

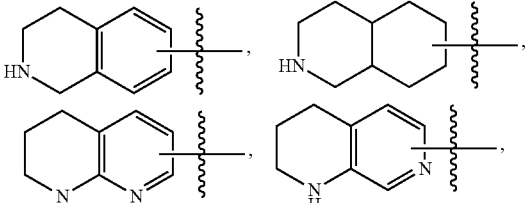

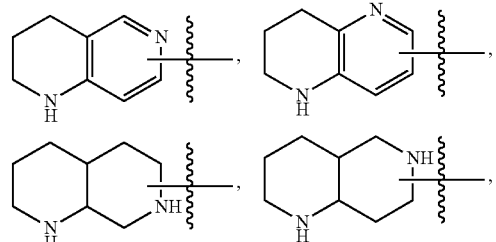

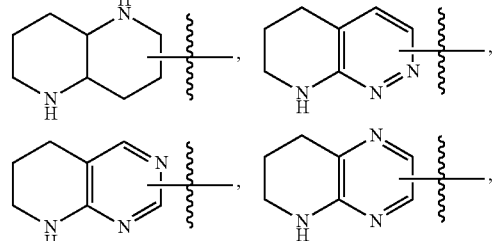

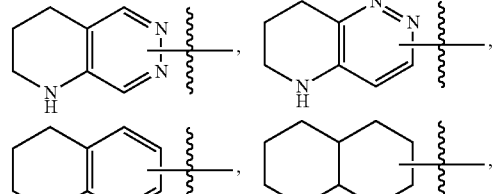

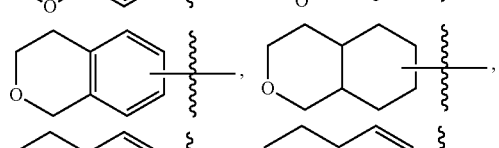

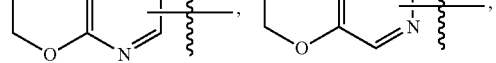

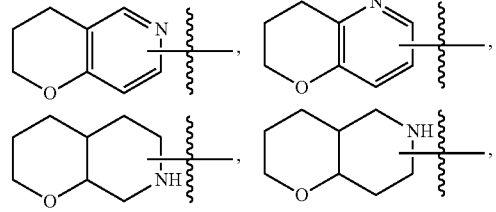

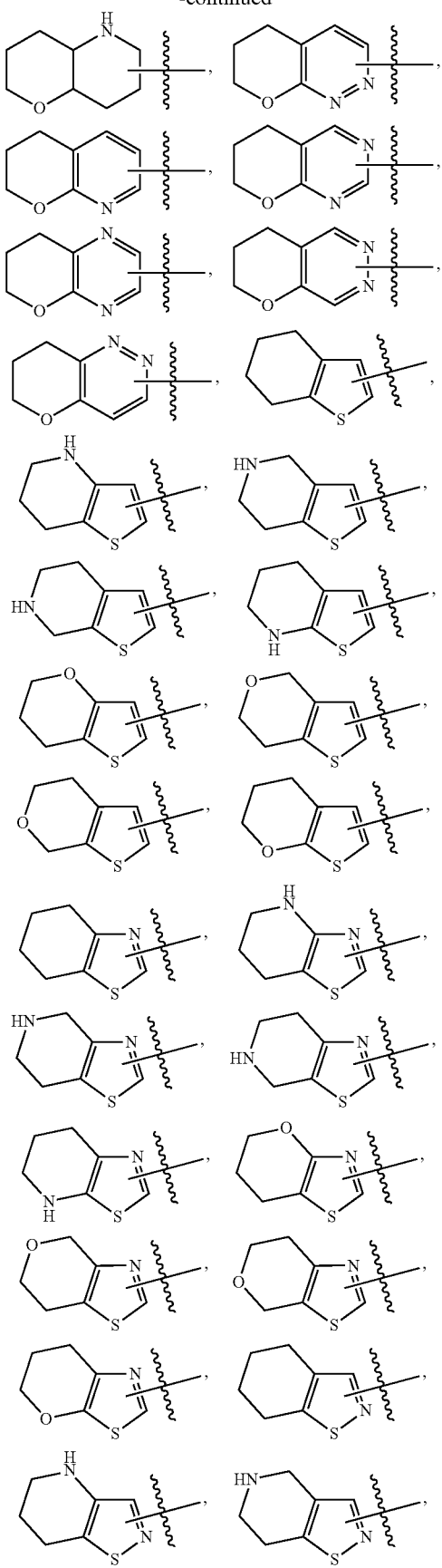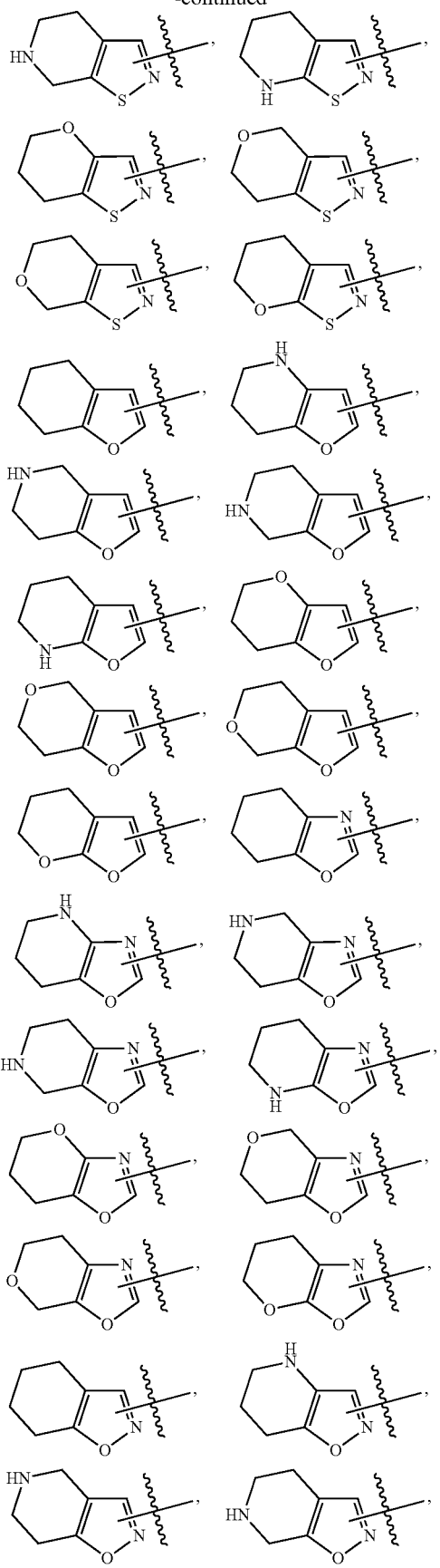

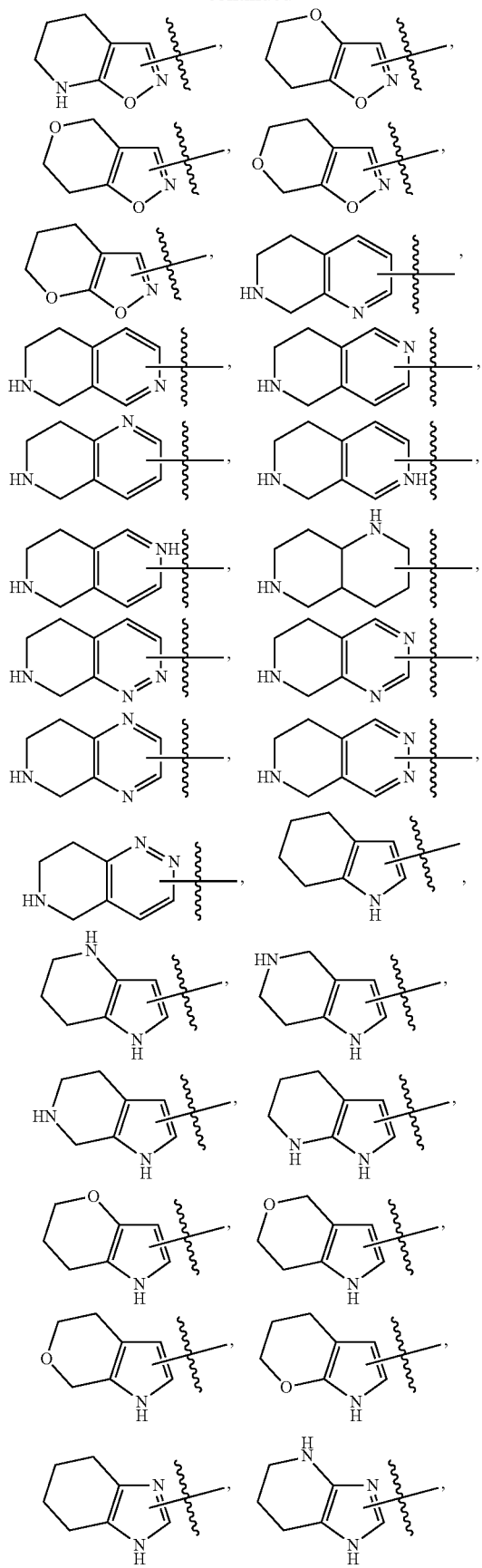
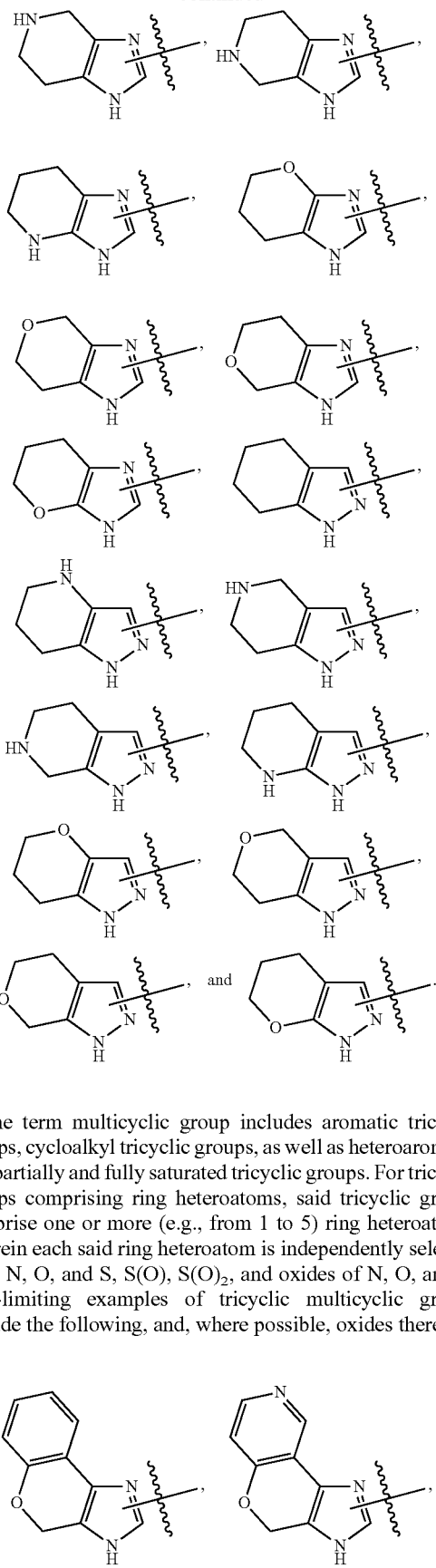

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S: Non-limiting examples of tricyclic multicyclic groups include the following, and, where possible, oxides thereof:

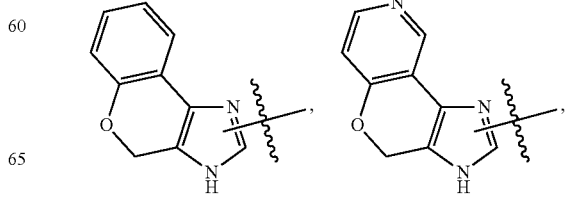

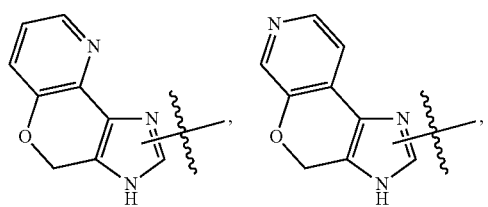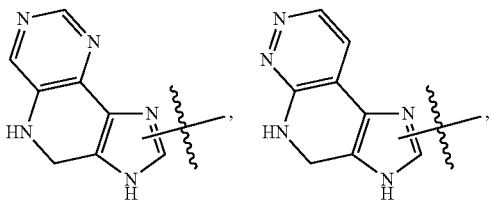

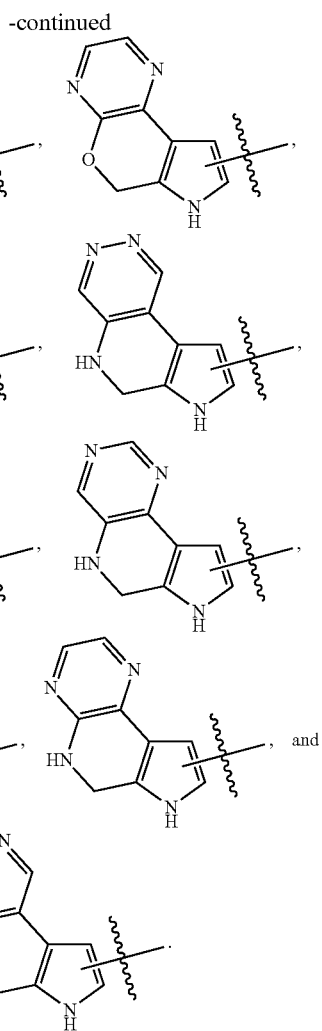

"Arylalkyl" (or "aralkyl") means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Spirocycloalkyl" means a cycloalkyl group attached to a parent moiety at a single carbon atom. Non-limiting examples of spirocycloalkyl wherein the parent moiety is a cycloalkyl include spiro[2.5]octane, spiro[2.4]heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

"Sprioheterocycloalkyl" means a heterocycloalkyl group, as defined herein, attached to a parent moiety at a single carbon atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in $-N(R^6)_2$, or a variable appears more than once in a structure presented herein, the variables can be the same or different.

The line ----, as a bond generally indicates a mixture of, or either of, the possible isomers, e.g., containing (R)- and (S)-stereochemistry. For example:

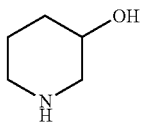

means containing both

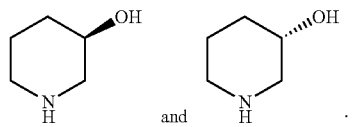

The wavy line ∿∿∿, used herein, indicates a point of attachment to the rest of the compound. Lines drawn into the ring systems, such as, for example:

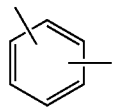

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

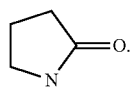

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

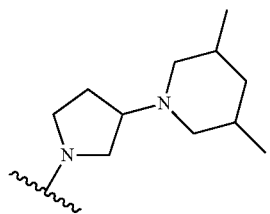 [SMILES: *N1CCC(N2CC(C)CC(C)C2)C1]

represents

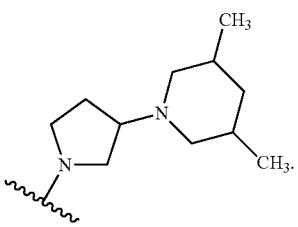 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt thereof, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$ alkylcarbamoyl-$(C_1-C_2)$alkyl and piperidino-, pyrrolidino- or morpholino$(C_2-C_3)$alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Another embodiment provides tautomers of the compounds of the invention, and salts, solvates, esters and prodrugs thereof. Also, for example, all keto-enol and imine-enamine forms of the compounds are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment provides isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for compositions comprising a compound of the invention formulated for subcutaneous delivery. Another embodiment provides for compositions suitable for oral delivery. In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. In Schemes A, B, and C, q is an integer from 0 to 3 and the other variables shown are defined as in Formula I.

Techniques, solvents and reagents may be referred to by their abbreviations as follows:

[1,1'-Bis(diphenylphosphino)ferrocene]dichloro palladium (II): $PdCl_2dppf$
1-(3-Dimethylaminopropyl)-3-ethylcarbodiimide hydrochloride: EDCI
1,2-dimethoxyethane: DME
2-(Trimethylsilyl)ethanol: TMSethanol
2-(Trimethylsilyl)ethoxycarbonyl: Teoc
3-Chloroperoxybenzoic acid: mCPBA
Acetonitrile: MeCN 35
Allyl carbamate: ALLOC
Benzyl: Bn
Centimeters: cm
Diisopropylamine: $iPr_2NH$
Diisopropylethylamine: DIEA or $iPr_2NEt$
Dimethylacetamide: DMA
Dimethylformamide: DMF
Dimethylsulfoxide: DMSO
Diphenylphosphoryl azide: DPPA
Ether or diethyl ether: $Et_2O$
Ethyl acetate: AcOEt or EtOAc
Grams: g
High performance liquid chromatography: HPLC
High resolution mass spectrometry: HRMS
Iron(III) acetylacetonate: $Fe(acac)_3$
Liquid chromatography mass Spectrometry: LCMS
Lithium diisopropylamide: LDA
Methanesulfonyl chloride: $MeSO_2Cl$ Methanol: MeOH
Methyl magnesium bromide: MeMgBr
Microliters: μl
Milligrams: mg
Milliliters: mL
Millimoles: mmol
N-bromosuccinimide: NBS
n-Butyllithium: nBuLi
Nuclear magnetic resonance spectroscopy: NMR
Palladium(II) acetate: Pd(OAc)$_2$
paramethoxy benzyl: PMB
Retention time: $t_R$
Room temperature (ambient, about 25° C.): rt
tert-Butoxycarbonyl: t-Boc or Boc
Tetrahydrofuran: THF
Thin layer chromatography: TLC
Triethylamine: Et$_3$N or TEA Trifluoroacetic acid: TFA
Trifluoric acid: TFA

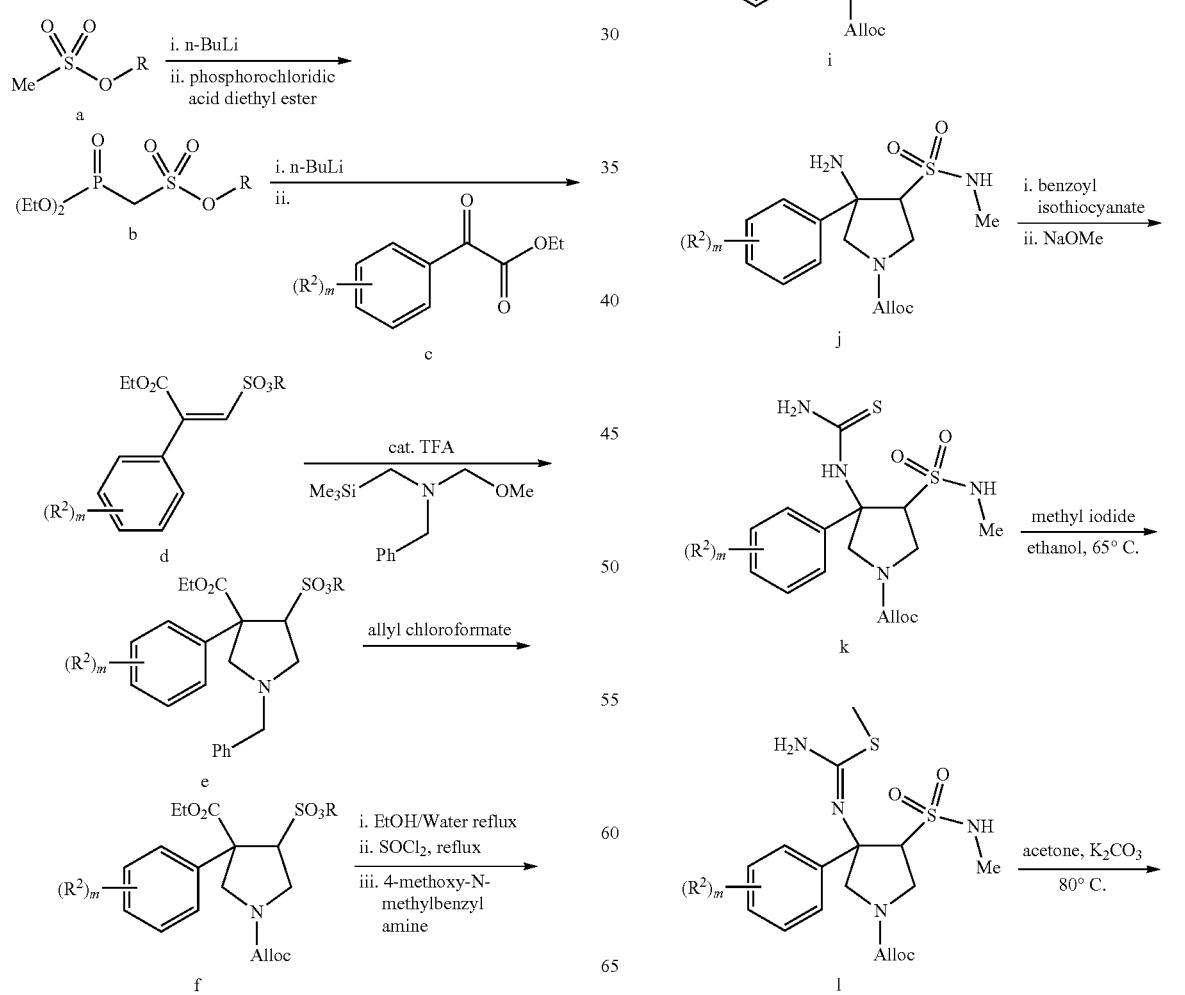

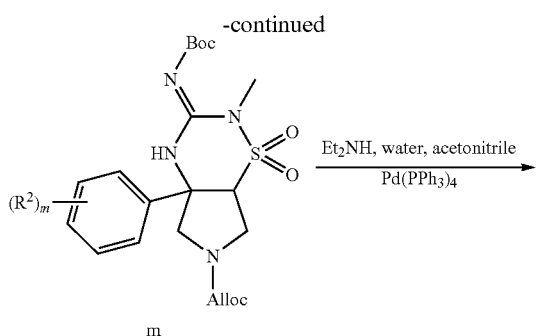

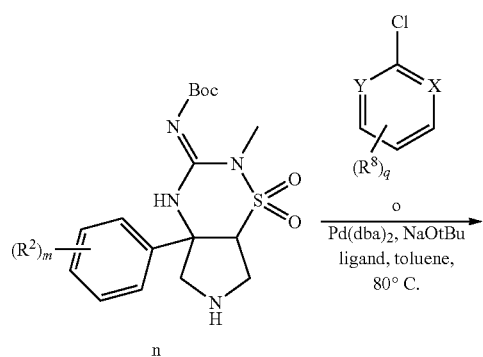

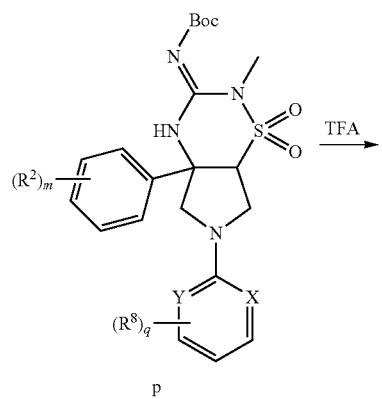

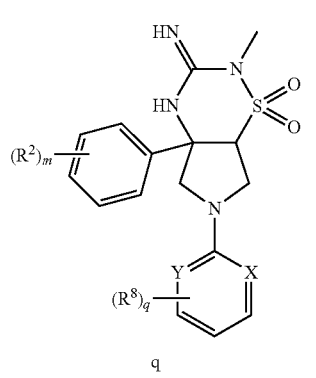

An alkyl methane sulfonat a such as isopropyl methan sulfonate can be treated with an alkyl lithium such as n-butyllithium at low temperature. The anion can be treated with a dialkyl chlorophosphate such as diethyl chlorophosphate to provide sulfonate b. Treatment of b with an alkyl lithium such as n-butyllithium at low temperature (−78° C.) and subsequent treatment with an alkyl benzoylformate such as ethyl benzoylformate c will afford d. Treatment of d with N-benzyl-N-methoxymethyl-N-(trimethylsilyl)methylamine in a halogenated solvent such as dichloromethane with a catalytic amount of TFA will provide the pyrrolidine e. The pyrrolidine e can be treated with an alkyl chloroformate such as ally chloroformate to yield the allyl carbamate f. The alkyl sulfonate f can be converted to a sulfonamide by first treating f with ethanol and water at reflux to provide the sulfonic acid. The sulfonic acid can be treated with $SOCl_2$ at relux to provide the sulfonyl chloride. Treatment of the sulfonyl chloride with an amine such as 4-methoxy-N-methylbenzylamine will yield g. Treatment of g with an aqueous base such as LiOH at elevated temperature (60° C.) will afford the carboxylic acid h. Conversion of the carboxylic acid of h to an acyl azide by treatment with DPPA and subsequent heating in the presence of water and TFA will provide the amine i. The PMB group on i can be removed by heating i in a halogenated solvent such as chloroform in the presence of TFA and dimethoxybenzene to provide j. Treatment of the amine j with benzoyl isothiocyanate followed by sodium methoxide will yield the thiourea k. The thiourea k can be converted to the S-methylthiourea l by the treatment with iodomethane in an alcoholic solvent such as ethanol at elevated temperature. Treatment of l with potassium carbonate in acetone at 80° C. will provide the fused bicyclic pyrrolidine m. The alloc protecting group can be removed by treating m with a palladium catalyst such as $Pd(PPh_3)_4$ in water and acetonitrile in the presence of a dialkyl amine such as diethylamine to provide the pyrrolidine n. Treatment of n with an aryl chloride such as o in the presence of a palladium catalyst such as $Pd(dba)_2$, a ligand such as 2-di-t-butylphosphino-2'-(N,N-dimethoxyamino)biphenyl, and a base such as sodium tert-butoxide in a nonpolar solvent such as toluene at elevated temperature (80° C.) will afford the N-arylpyrrolidine p. Treatment of p with an acid such as TFA will provide q.

Scheme B

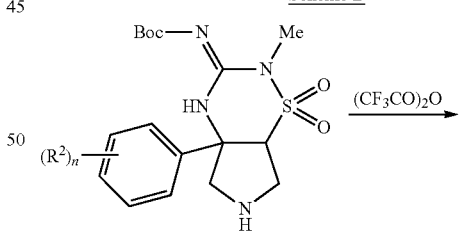

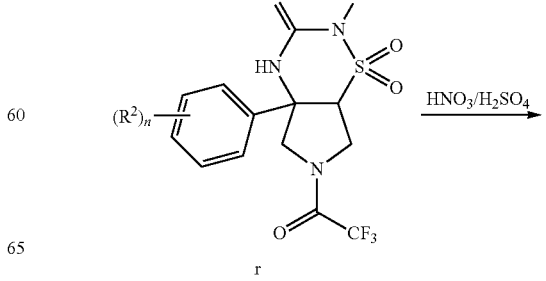

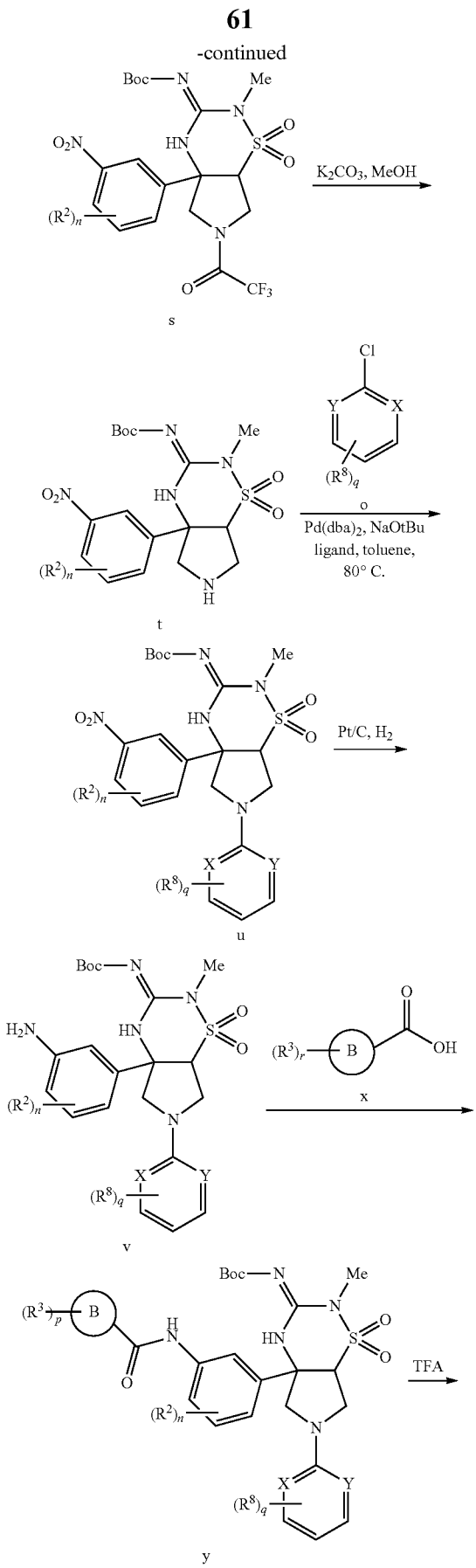

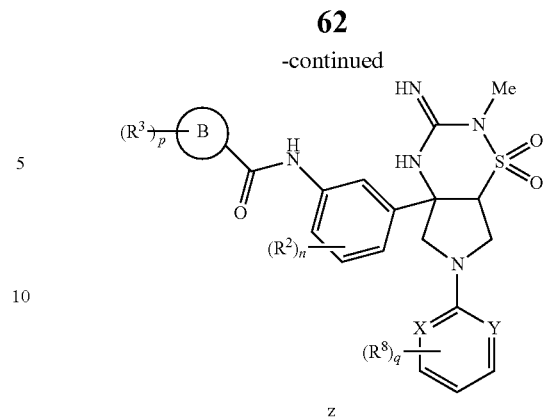

The pyrrolidine can be protected with a nitrogen protecting group such as trifluoroacetamide by the treatment with trifluoroacetic anhydride in the presence of a base such as pyridine in a halogenated solvent such as dichloromethane. The aromatic ring in r can be nitrated by the treatment with fuming nitric acid and concentrated sulfuric acid. Treatment of the crude product with di-tert-butyldicarbonate in dichloromethane would provide s. The protecting group can be removed upon the treatment of s with potassium carbonate in methanol at room temperature. Treatment of t with an aryl chloride such as o in the presence of a palladium catalyst such as Pd(dba)$_2$, a ligand such as 2-di-t-butylphosphino-2'-(N,N-dimethoxyamino)biphenyl, and a base such as sodium tert-butoxide in a nonpolar solvent such as toluene at elevated temperature (80° C.) will afford the N-arylpyrrolidine u. The nitro group can be reduce to the amine by the treatment of u with platinum on carbon in an alcoholic solvent such as methanol under an atmosphere of hydrogen (40 psi). The resulting aniline can be coupled with an acid such as x using a coupling agent such as bis(2-oxo-3-oxazolidinyl)phosphonic chloride to provide y. The Boc group can be removed under acidic conditions such as trifluoracetic acid in dichloromethane to yield z.

Scheme C

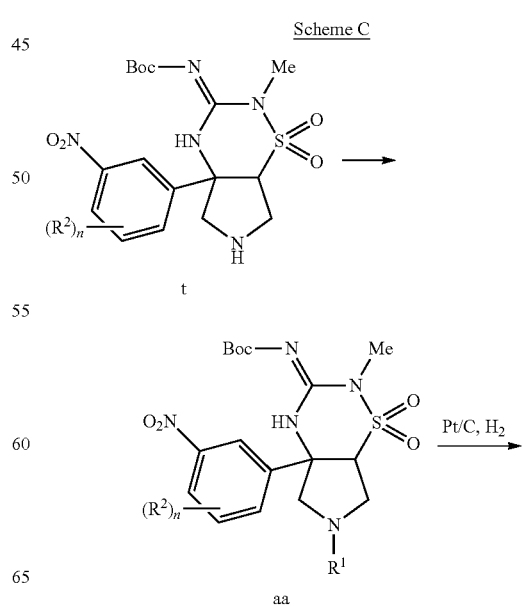

-continued

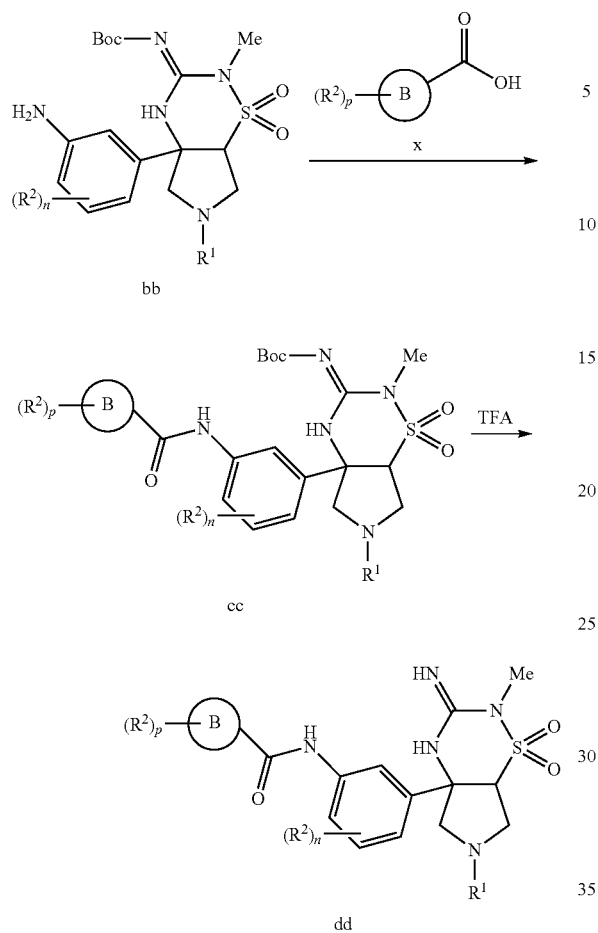

The pyrrolidine t prepared in Scheme B can be reacted with acid chlorides, sulfonyl chlorides, or isocyanates in the presence of a halogenated solvent such as DCM and a tertiary amine base such as diisopropylethyl amine to install the $R^1$ moiety in aa. In addition, t can be reacted with alkyl halides in a solvent such as DMF in the presence of a base such as potassium carbonate at elevated temperature to prepare aa in which $R^1$ is an alky group. The nitro group of aa can be reduced with platinum on carbon under an atmosphere of hydrogen (40 psi) in an alcoholic solvent to provide the aniline bb. The resulting aniline bb can be coupled with an acid such as x using a coupling agent such as bis(2-oxo-3-oxazolidinyl)phosphonic chloride to provide cc. The Boc group can be removed under acidic conditions such as trifluoracetic acid in dichloromethane to yield dd.

Scheme 1

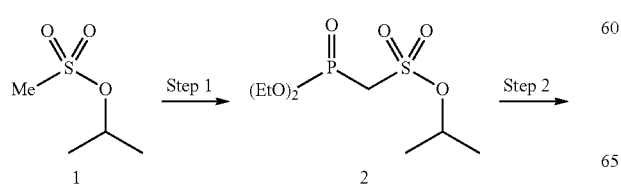

-continued

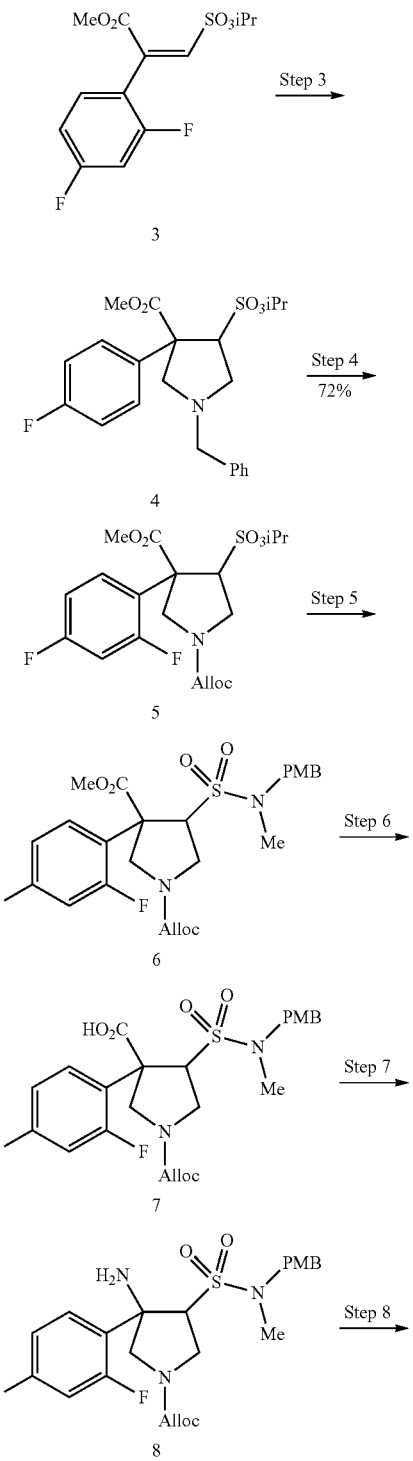

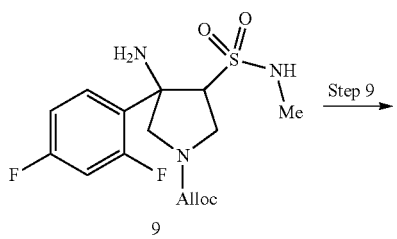

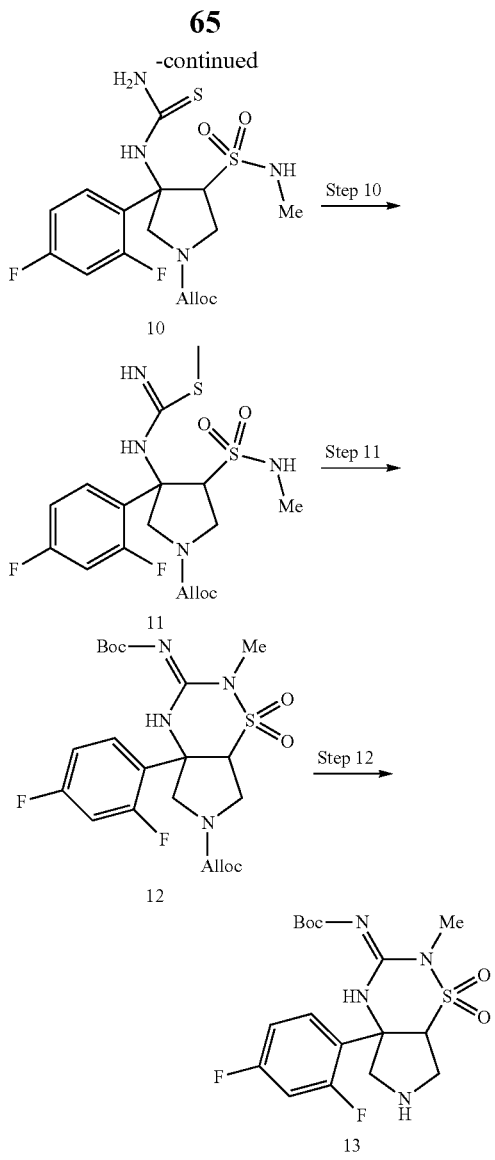

Step 1

To isopropyl methanesulfonate 1 (24.9 g, 180 mmol) in THF (475 mL) at −78° C. was added n-butyllithium (124 mL, 1.6 M in hexane, 199 mmol) dropwise over 20 minutes. Stirred for 1 hour at −78° C. and then added phosphorochloridic acid diethyl ester (14.0 mL, 97.3 mmol). Transferred to a −50° C. bath (acetonitrile/CO$_2$) and stirred for 1.5 h. Worked up by adding saturated aqueous NH$_4$Cl and allowing to warm to room temperature. Added water and extracted with EtOAc. Combined organics and washed with water and brine. Dried (MgSO$_4$), filtered, and concentrated in vacuo to provide a yellow liquid. Purified by silica gel chromatography (10-90% EtOAc/hex over 30 minutes) to provide 2 as a straw-colored oil (23.2 g, 87%).

Step 2

To the sulfonate 2 (9.8 g, 35.8 mmol) in THF (116 mL) at −78° C. was added n-butyllithium (24.6 mL, 1.6 M in hexane, 39.4 mmol). Stirred for 1 h at −78° C. Added ethyl-2,4-difluorobenzoylformate (9.59 g, 44.8 mmol) in THF (15 mL). Stirred for 1 h at −78° C. and then took cold bath away and stirred for an additional 1 hour. Added saturated NH$_4$Cl and extracted with EtOAc. Combined organics and washed with water and brine. Dried (MgSO$_4$), filtered and concentrated in vacuo to provide a pale yellow liquid. Purified by silica gel chromatography (0-10% EtOAc/hex over 30 minutes then 10-15% EtOAc/hex over 15 minutes) to provide 3 as a straw-colored liquid (7.93 g, 66%).

Step 3

To 3 (15.6 g, 46.6 mmol) in methylene chloride (150 mL) at room temperature was added N-benzyl-N-methoxymethyl-N-(trimethylsilyl)methylamine (19.1 mL, 74.6 mmol) and trifluoroacetic acid (0.36 mL, 4.66 mmol). The reaction was put in an ice bath for 30 minutes and then warmed to room temperature. After stirring for 18 h, the reaction was concentrated in vacuo. The oil was taken up into methylene chloride and washed with saturated NaHCO$_3$, water, and brine. The organic layer was dried (MgSO$_4$), filtered, and concentrated in vacuo to provide an oil. The oil was purified by silica gel chromatography (SiO$_2$, 300 g: 0-20% EtOAc/hex over 30 minutes to provide 4 as a golden oil (20.4 g) that was contaminated with ~10-15% of 3. The mixture was carried on directly to the next step.

Step 4

To 4 (20.4 g, 45.5 mmol) in methylene chloride (140 mL) at 0° C. was added N,N,N',N'-tetramethyl-1,8-naphthalene-diamine (0.47 g, 2.2 mmol) and allyl chloroformate (11.6 mL, 109 mmol). Took the cold bath away and stirred for 18 h. The reaction was diluted with methylene chloride and washed with water and brine. The organic layer was dried (MgSO$_4$), filtered, and concentrated in vacuo to provide a golden oil. The oil was purified by silica gel chromatography (SiO$_2$, 330 g: 0-35% EtOAc/hex over 30 minutes and then 35-40% EtOAc/hex over the next ten minutes) to provide 5 (12.4 g, 61.5%) as a mixture of diastereomers.

Step 5

To 5 (12.4 g, 26.8 mmol) in ethanol (500 mL) was added water (24 mL). The mixture was warmed to reflux and stirred for 2 h. The reaction was concentrated in vacuo to provide the sulfonic acid (10.3 g). The sulfonic acid was carried on directly by taking it up into thionyl chloride (98 mL). The reaction was warmed to reflux and stirred for 4 h. The mixture was concentrated in vacuo to provide an oil. The oil was taken up into methylene chloride (86 mL) and cooled to 0° C. Added 4-methoxy-N-methylbenzylamine (6.07 g, 40.2 mmol) followed by N,N-diisopropylethyl amine (9.33 mL, 53.6 mmol). Took cold bath away and stirred for 28 h. Worked up by washing with 1N HCl, water, and brine. The organic layer was dried (MgSO$_4$), filtered, and concentrated in vacuo to provide a yellow/tan foam. Purification by silica gel chromatography (SiO$_2$—200 g: 0-40% EtOAc/hex over 30 minutes) provided 6 (7.0 g, 47%).

Step 6

To 6 (7.0 g, 13 mmol) in ethanol (49 mL) was added 2N LiOH$_{aq}$ (19 mL, 38 mmol). The reaction was warmed to 60° C. and stirred for 4 h. The reaction was cooled to room temperature and the ethanol was removed in vacuo. The mixture was acidified with 6N HCl and then extracted with EtOAc. The combined organic layers were washed with water and brine. The organic layer was dried (MgSO$_4$), filtered, and concentrated in vacuo to provide 7 (6.4 g, 96%).

Step 7

To 7 (6.24 g, 11.9 mmol) in THF (39 mL) at room temperature was added triethylamine (3.70 mL, 26.5 mmol) followed by diphenylphosphonic azide (3.18 mL, 14.8 mmol). The reaction was stirred for 24 h. Most of the solvent was removed in vacuo followed by the addition of acetonitrile (60 mL). The acetonitrile solution was added dropwise to a solution of acetonitrile (62 mL), water (43 mL), and trifluoroacetic acid (5.5 mL, 71 mmol) at 80° C. over 30 minutes. The reaction was stirred at 80° C. for 1.5 h. The reaction was cooled to room temperature and then concentrated in vacuo. EtOAc was added and the mixture was washed with saturated NaHCO$_3$, water, and brine. The organic layer was dried (MgSO$_4$), filtered, and concentrated in vacuo. Purification by silica gel chromatography (SiO$_2$—80 g: 0-6% MeOH/DCM to provide 8 (4.5 g, 77%).

Step 8

To 8 (4.5 g, 9.1 mmol) in chloroform (22 mL) was added m-dimethoxybenzene (8.34 mL, 64 mmol) and trifluoroacetic acid (21 mL). The mixture was warmed to reflux and stirred for 19 h. The mixture was then concentrated in vacuo and then taken up into DCM. The organic layer was washed with saturated NaHCO$_3$, water, and brine. The organic layer was then dried (MgSO$_4$), filtered, and concentrated in vacuo. Purification by silica gel chromatography (SiO$_2$—80 g: 0-10% MeOH/DCM) provided 9 (3.3 g, 96%).

Step 9

To 9 (0.27 g, 0.71 mmol) in methylene chloride (2.3 mL) was added benzoyl isothiocyanate (0.11 mL, 0.78 mmol). Stirred at room temperature for 24 h and then concentrated in vacuo. Added 0.5 M sodium methoxide in methanol (3.6 mL) and stirred for 3 h. Concentrated the reaction in vacuo. Added saturated NaHCO$_3$, and extracted with EtOAc. Combined the organics and washed with water and brine. Dried (MgSO$_4$) the organic layer, filtered, and concentrated in vacuo. The residue was purified by silica gel chromatography (0% MeOH/DCM over 10 minutes and then 0-6% MeOH/DCM over 30 minutes) to provide 10 (0.26 g, 86%).

Step 10

To 10 (0.31 g, 0.71 mmol) in ethanol (2.5 mL) was added methyl iodide (0.053 mL, 0.86 mmol). The reaction was warmed to 65° C. and stirred for 3 h. The reaction was then cooled to room temperature and concentrated in vacuo. The residue was partitioned between EtOAc and saturated NaHCO$_3$ and then extracted with EtOAc. The organics were combined and washed with water and brine. Dried (MgSO$_4$) the organic layer, filtered, and concentrated in vacuo to provide 11 (0.24 g, 75%) that was carried on directly without further purification.

Step 11

To 11 (0.24 g, 0.54 mmol) in acetone (2.5 mL) in a glass reaction tube was added potassium carbonate (0.15 g, 1.1 mmol). The reaction tube was capped and warmed to 80° C. The reaction was heated for 16 h and then concentrated in vacuo. To the residue was added methylene chloride (2.0 mL) and di-tert-butyldicarbonate (0.18 g, 0.80 mmol). The reaction was stirred for 72 h and methylene chloride and water was added. The mixture was extracted with methylene chloride. The organic layers were combined and washed with water and brine, dried (MgSO$_4$), filtered, and concentrated in vacuo. The residue was purified by silica gel chromatography (0-30% EtOAc/hex over 30 minutes) to provide 12 (0.11 g, 41%).

Step 12

To 12 (1.30 g, 2.60 mmol) in 1:1 acetonitrile:water (12 mL) was added diethylamine (5.4 mL, 52 mmol) and tetrakis(triphenylphosphine)palladium (0.03 g, 0.026 mmol). The reaction was stirred at room temperature for 20 h and then concentrated in vacuo. The residue was partitioned between EtOAc and brine. The mixture was extracted with EtOAc. The combined organic layers were washed with brine, dried (MgSO$_4$), filtered, and concentrated in vacuo. The residue was purified by silica gel chromatography (0-80% EtOAc/hex over 30 minutes) to provide 13 (0.84 g, 77%).

Preparation of methyl-2,4,5-benzoylformate

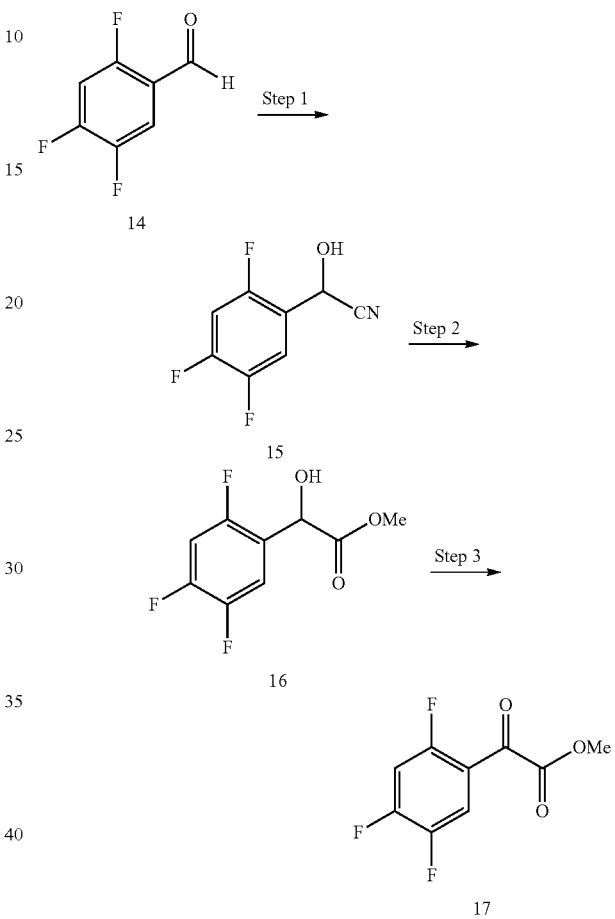

Step 1

To a solution of sodium bisulfate (53.6 g, 510 mmol) in water (200 mL) was added the 2,4,5-trifluorobenzaldehyde 14 (40.0 g, 250 mmol) in portions. The mixture was stirred at room temperature for 2-3 h. The mixture was then cooled in an ice bath and a solution of potassium cyanide (33.0 g, 510 mmol) in water (130 mL) was added dropwise over 30 minutes. The cold bath was removed and the reaction was stirred for 18 h at room temperature. Extracted with ether and then ethyl acetate. Combined the organics and washed with water and brine. Dried (NaSO$_4$), filtered, and concentrated in vacuo to provide 15 as an oil (42.11 g) that was carried on directly to the next step.

Step 2

A solution of 15 (42.1 g, 230 mmol) in concentrated HCl (100 mL) was heated to 80° C. and stirred for 6 h. The reaction was cooled to room temperature and then cooled in ice/brine bath. The mixture was basified to ~pH 10 using solid KOH. The mixture was extracted with ether. The organic layer was acidified using sulfuric acid and then extracted with ether. The organics were combined, washed with brine, dried (NaSO$_4$), and filtered to provide a yellow solid. To the solid was added MeOH (200 mL) and H₂SO₄ (9 mL). The reaction was warmed to reflux and stirred for 4 h. The reaction was then cooled room temperature and the pH was adjusted to pH 9 by the addition of 2N Na₂CO₃. The mixture was extracted with ether. The organics were combined and washed with brine, dried (NaSO₄), filtered, and concentrated in vacuo to provide 16 (29.7 g, 60%).

Step 3

To 16 (6.53 g, 29.7 mmol) in methylene chloride (100 mL) at 0° C. was added MnO₂ (39.0 g, 87.0 mmol). Stirred at room temperature for 18 h. Filtered through a pad of silica gel eluting with methylene chloride followed by ethyl acetate. Removed the solvent in vacuo to provide 17 (3.66 g, 56%).

The intermediate pyrrolidines in Table 1 were prepared using the chemistry described in Scheme 1 while utilizing the shown keto ester in step 2 of Scheme 1.

TABLE 1

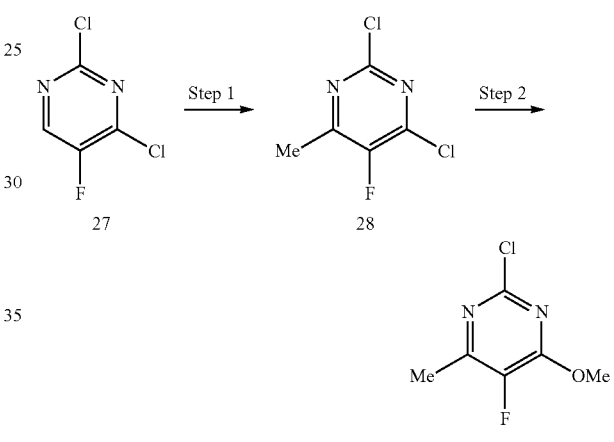

Preparation of
2-chloro-5-fluoro-4-methoxy-6-methylpyrimidine

Step 1

A solution of 2,4-dichloro-5-fluoropyrimidine 27 (10 g, 60 mmol) in DME (30 mL) was added to a solution of methyl magnesium bromide (3 M in ether/30 mL/1.5 equiv) in THF (30 mL) at 0° C. over 10 minutes. The reaction was stirred at 10-15° C. for 1 h and then cooled to 0° C. Triethyl amine (8.3 mL, 1 equiv) in THF (16 mL) was added to the reaction mixture while keeping the reaction temperature below 5° C. Iodine (15.2 g, 1 equiv) in THF (24 mL) was then added dropwise keeping the temperature below 15° C. The reaction was stirred for 30 minutes and water was added (150 mL). The pH was adjusted to pH=1 by the addition of aqueous 5N HCl. The mixture was extracted with EtOAc. The combined organics were washed with 2% aqueous sodium bisulfite and brine. The organic layer was dried (Na₂SO₄), filtered, and concentrated in vacuo. The resulting solid was purified by silica gel chromatography (0-8% EtOAc/hex over 30 minutes) to provide 28 (6.75 g, 64%).

Step 2

To 28 (25 g, 138 mmol) in THF (250 mL) at 0° C. was added 30 g of a 25%/wt NaOMe in methanol solution (138 mmol). Allowed to warm to room temperature over 30 minutes. Concentrated the reaction in vacuo. Purified the residue by silica gel chromatography (0-20% acetone/hexane over 20 minutes) to provide 29 (12.6 g, 52%).

Preparation of 2-chloro-4-ethyl-5-fluoro-6-methoxypyrimidine

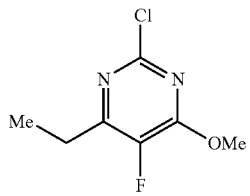
30

The pyrimidine 30 was prepared in the same manner as 29 in scheme 3 except that ethyl magnesium bromide was used instead of methyl magnesium bromide in step 1.

Preparation of 2-chloro-4-cyclopropyl-5-fluoro-6-methoxypyrimidine

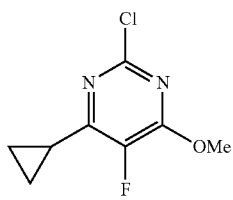
31

The pyrimidine 31 was prepared in the same manner as 29 in scheme 3 except that cyclopropyl magnesium bromide was used instead of methyl magnesium bromide in step 1.

Preparation of 2-chloro-4-methoxy-4-(methoxymethyl)pyridine

Scheme 4

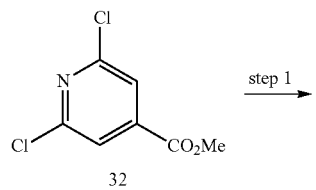
32

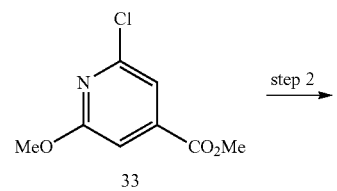
33

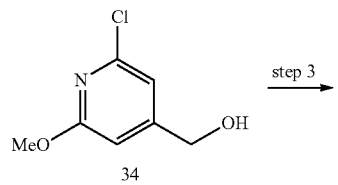
34

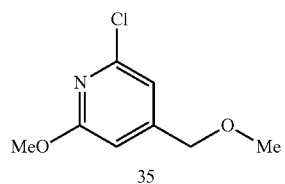
35

Step 1

To methyl-2,6-dichloroisonicotonate (10.3 g, 50 mmol) in methanol (45 mL) was added 25% NaOMe in methanol (13 mL). Stirred at room temperature for 5 h. The reaction was then poured into water (200 mL). The white precipitate was filtered, washed with water, and air-dried to provide 33 (7.89 g, 79%).

Step 2

To 33 (4.03 g, 20 mmol) in THF (50 mL) in a water bath was added LiBH$_4$ (1.31 g, 60 mmol). Ethanol (10 mL) was added to the reaction mixture dropwise and the reaction mixture was stirred at room temperature for 15 h. Excess aqueous 1N NaOH was added and the mixture extracted with EtOAc. The combined organics were washed with water and brine, dried (MgSO$_4$), filtered, and concentrated in vacuo to provide 34 (3.43 g, 99%).

Step 3

To 34 (3.43 g, 19.8 mmol) in DMF (30 mL) at room temperature was added sodium hydride (60% dispersion in mineral oil, 1.19 g, 29.6 mmol). The solution was stirred at room temperature for 30 minutes and iodomethane (6.1 mL, 98.8 mmol) was added. The reaction was stirred at room temperature for 18 h. Water was added and the mixture was extracted with EtOAc. The organic layers were combined, washed with water and brine, dried (MgSO$_4$), filtered, and concentrated in vacuo to provide 35 (2.71 g, 73%).

Preparation of 2-chloro-6-methoxy-4-(ethoxymethyl)pyridine

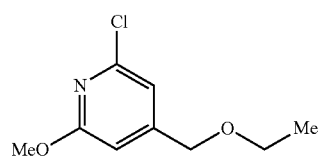
36

The pyridine 36 was prepared in a similar fashion as 35 in scheme 4 except that ethyliodide was used instead of iodomethane in step 3.

Preparation of 2-chloro-5-fluoro-4,6-dimethoxypyrimidine

Scheme 5

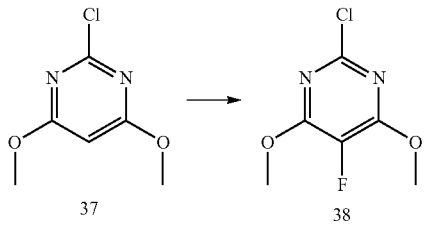

To THF (200 mL) at 0° C. was added diisopropyl amine (93 mL, 307 mmol) followed by n-butyllithium (2.5 M in hexanes, 115 mL, 287 mmol). Stirred at room temperature for 30 minutes. Cooled the reaction to −78° C. and added the LDA solution via cannula to a solution of 2-chloro-4,6-dimethoxypyrimidine 37 (25 g, 143 mmol) in THF (1.4 L) at −78° C. After addition, stirred for an additional 1.5 h at −78° C. A solution of N-fluorobenzenesulfinimide (135 g, 428 mmol) in THF (400 mL) was slowly added to the reaction using a cannula. Allowed the reaction to warm to room temperature and stirred for 15 h. Worked up by adding saturated aqueous NH₄Cl and extracted with EtOAc. Combined organics and washed with water and brine, dried (MgSO₄), filtered, and concentrated in vacuo. Purified by silica gel chromatography (0.5% EtOAc/hex) to provide 38 (12.1 g, 63 mmol).

Preparation of Ex. 1

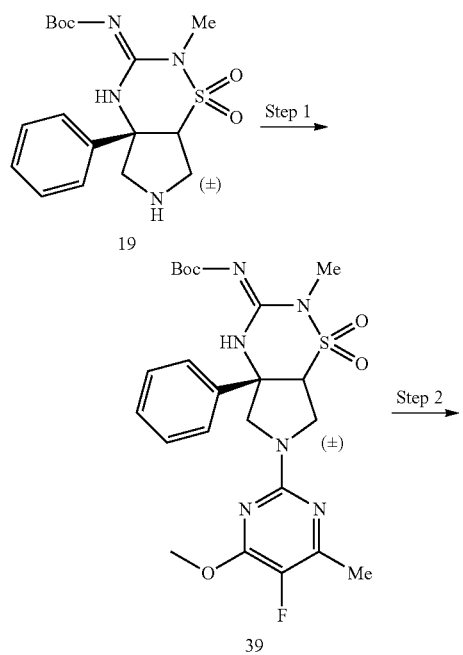

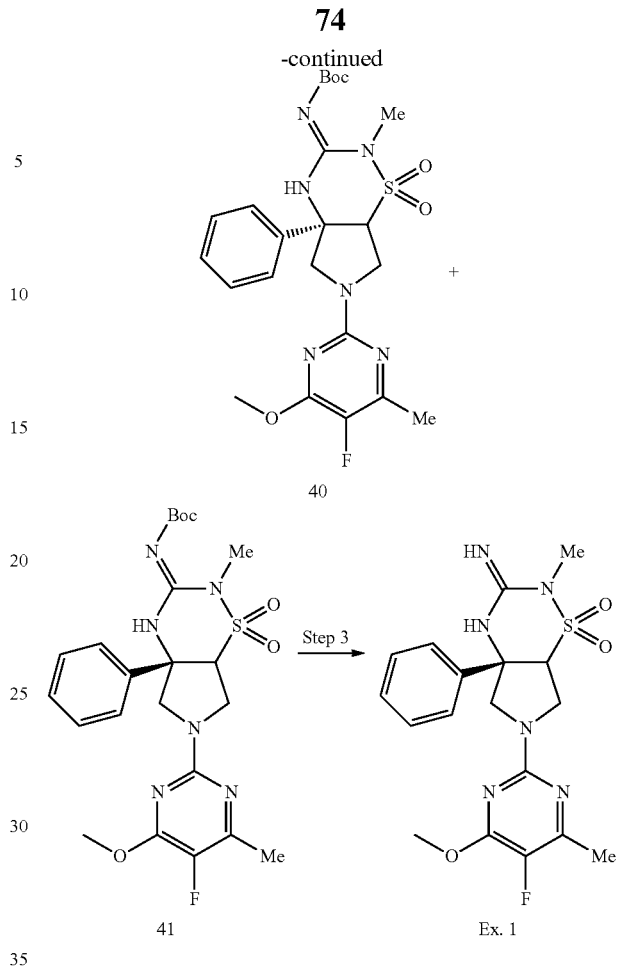

Step 1

To 19 (394 mg, 1.04 mmol) in a reaction tube was added toluene (4.5 mL). Nitrogen was bubbled through the reaction for 5 minutes. 2-chloro-5-fluoro-4-methoxypyrimidine 29 (219 mg, 1.24 mmol), 2-di-t-butylphosphino-2'-(N,N-dimethoxyamino)biphenyl (18 mg, 0.052 mmol), sodium t-butoxide (219 mg, 2.28 mmol), and Pd(dba)₂ (30 mg, 0.052 mmol) were added. Nitrogen was bubbled through the reaction mixture for 5 minutes. The reaction vessel was sealed and warmed to 80° C. and stirred for 30 minutes. The reaction mixture was cooled to room temperature and aqueous saturated NH₄Cl was added. The mixture was extracted with EtOAc. The combined organics were washed with water and brine, dried (MgSO₄), filtered, and concentrated in vacuo. The residue was purified by silica gel chromatography (0-25% EtOAc/hex over 25 minutes) to provide 39 (360 mg, 67%) as a racemate.

Step 2

The racemate 39 (360 mg) was resolved using chiral HPLC (Chiralcel OD, 95% hexane/IPA, 50 ml/min, 220 nm) to provide the desired enantiomer 41 (143 mg) as the faster eluting peak and the other enantiomer 40 as the slower eluting peak.

Step 3

To 41 (138 mg, 0.26 mmol) in DCM (1.5 mL) was added TFA (1.5 mL). The reaction was stirred for 1 h at room temperature. The reaction mixture was concentrated in vacuo. The residue was taken up into DCM and washed with water and brine, dried (MgSO₄), filtered, and concentrated in vacuo to provide Ex. 1 (106 mg, 97%).

75

Preparation of (7aR)-6-(5-fluoro-4-methoxy-6-methyl-2-pyrimidinyl)hexahydro-2-methyl-4aS-phenylpyrrolo[3,4-e]-1,2,4-thiadazin-3(2H)-imine-1,1-dioxide Scheme 7

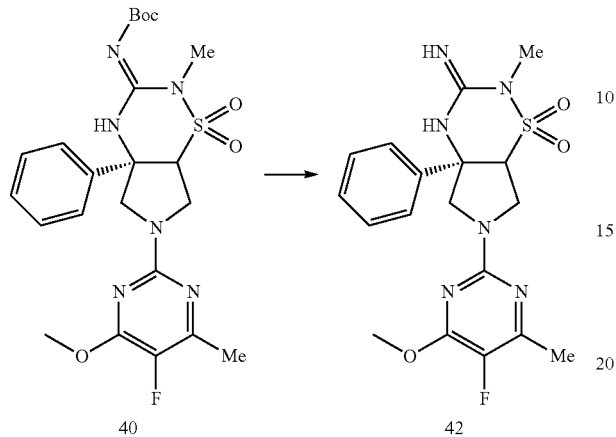

76

Using the conditions in step 3 of scheme 6, 40 was converted to 42.

The examples in table 2 were prepared in a similar fashion as Ex. 1 in scheme 6 using the specified intermediate pyrrolidine and aryl chloride as the coupling partners in step 1.

TABLE 2

| Intermediate Pyrrolidine | Aryl Chloride | HPLC Conditions for Step 2 | Example number | Example |
|---|---|---|---|---|
| 21 | 29 | A | Ex. 2 | |
| 23 | 29 | B | Ex. 3 | |

TABLE 2-continued
| Intermediate Pyrrolidine | Aryl Chloride | HPLC Conditions for Step 2 | Example number | Example |
|---|---|---|---|---|
| 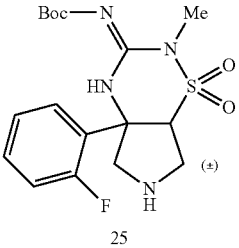 [SMILES: CN1/C(=N/C(=O)OC(C)(C)C)NC2(c3ccccc3F)CNCC2S1(=O)=O] 25 | 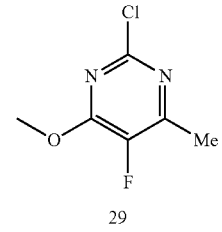 29 | B | Ex. 4 | 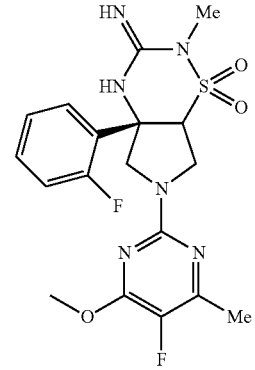 [SMILES: COc1nc(N2CC3[C@](c4ccccc4F)(C2)NC(=N)N(C)S3(=O)=O)nc(C)c1F] |
| 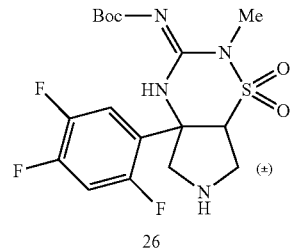 26 | 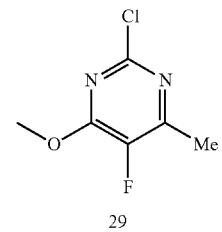 29 | C | Ex. 5 | 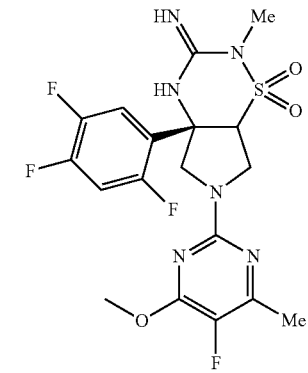 [SMILES: COc1nc(N2CC3[C@](c4cc(F)c(F)cc4F)(C2)NC(=N)N(C)S3(=O)=O)nc(C)c1F] |
| 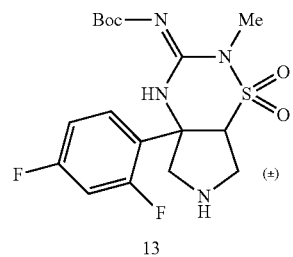 [SMILES: CN1/C(=N/C(=O)OC(C)(C)C)NC2(c3ccc(F)cc3F)CNCC2S1(=O)=O] 13 | 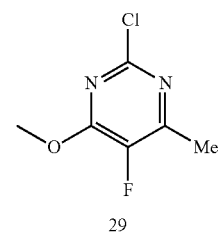 29 | B | Ex. 6 | 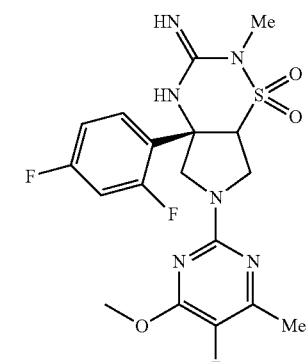 |
| 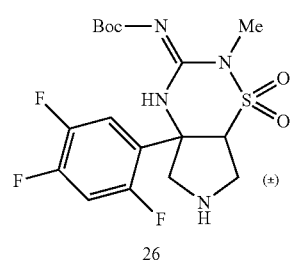 [SMILES: CN1/C(=N/C(=O)OC(C)(C)C)NC2(c3cc(F)c(F)cc3F)CNCC2S1(=O)=O] 26 | 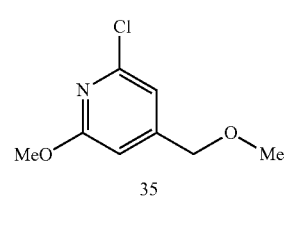 [SMILES: COCc1cc(Cl)nc(OC)c1] 35 | C | Ex. 7 | 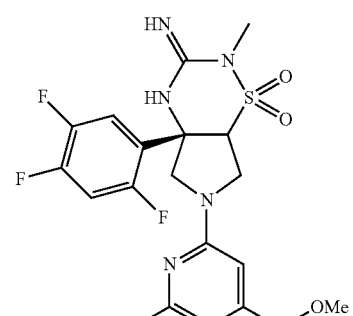 |

TABLE 2-continued

| Intermediate Pyrrolidine | Aryl Chloride | HPLC Conditions for Step 2 | Example number | Example |
|---|---|---|---|---|
| 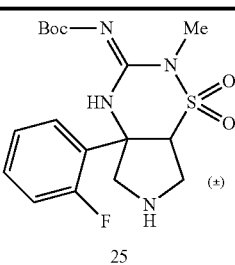 25 | 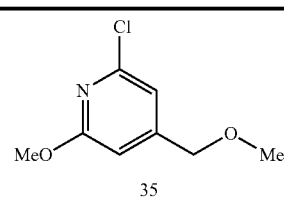 35 | B | Ex. 8 | 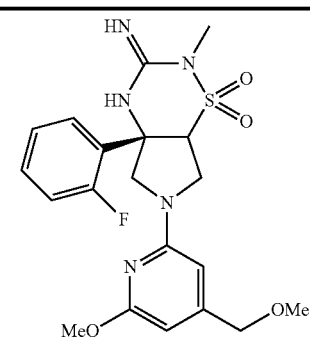 |
| 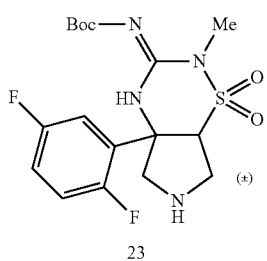 [SMILES: CN1/C(=N/C(=O)OC(C)(C)C)NC2(c3cc(F)ccc3F)CNCC2S1(=O)=O] 23 | 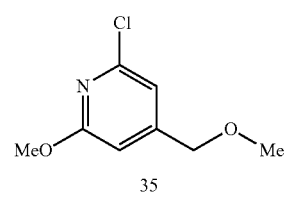 [SMILES: COCc1cc(Cl)nc(OC)c1] 35 | D | Ex. 9 | 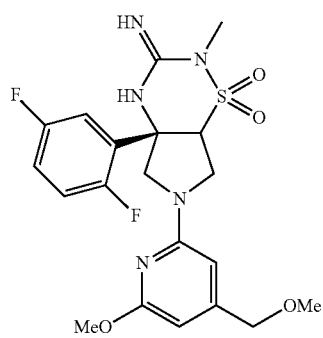 [SMILES: COCc1cc(OC)nc(N2CC3[C@](c4cc(F)ccc4F)(C2)NC(=N)N(C)S3(=O)=O)c1] |

HPLC conditions for step 2 in scheme 6
A Chiralcel OD, 5% IPA/hex, 50 mL/min, faster eluting peak
B Chiralpak AD, 10% IPA/hex, 50 mL/min, slower eluting peak
C Chiralpak AD, 5% IPA/hex, 50 mL/min, slower eluting peak
D Chiralpak AD, 3% IPA/hex, 50 mL/min, slower eluting peak The compounds in table 3 were prepared in a similar fashion as Ex. 1 in scheme 6 using the specified pyrrolidine and the aryl chloride as coupling partners in step 1. In addition, step 2 was omitted and thus final products are racemic.

TABLE 3

| Intermediate Pyrrolidine | Aryl Chloride | Example number | Example |
|---|---|---|---|
| 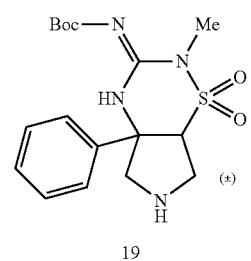 [SMILES: CN1/C(=N/C(=O)OC(C)(C)C)NC2(c3ccccc3)CNCC2S1(=O)=O] 19 | 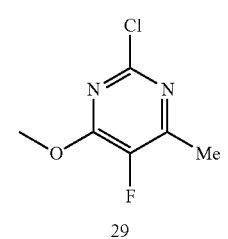 29 | Ex. 10 | 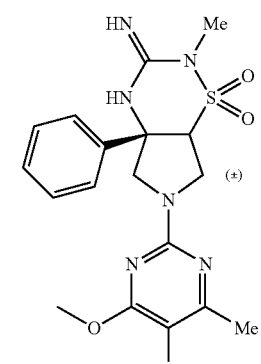 |

TABLE 3-continued

| Intermediate Pyrrolidine | Aryl Chloride | Example number | Example |
|---|---|---|---|
| 19 | 36 | Ex. 11 | |
| 19 | 35 | Ex. 12 | |
| 19 | 38 | Ex. 13 | |
| 19 | | Ex. 14 | |

TABLE 3-continued
| Intermediate Pyrrolidine | Aryl Chloride | Example number | Example |
|---|---|---|---|
| 19 | 30 | Ex. 15 | |
| 19 | 31 | Ex. 16 | |
| 19 | | Ex. 17 | |
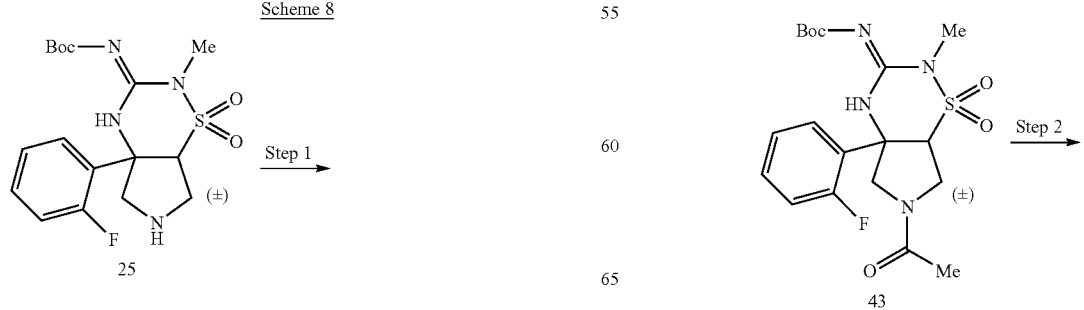
Scheme 8

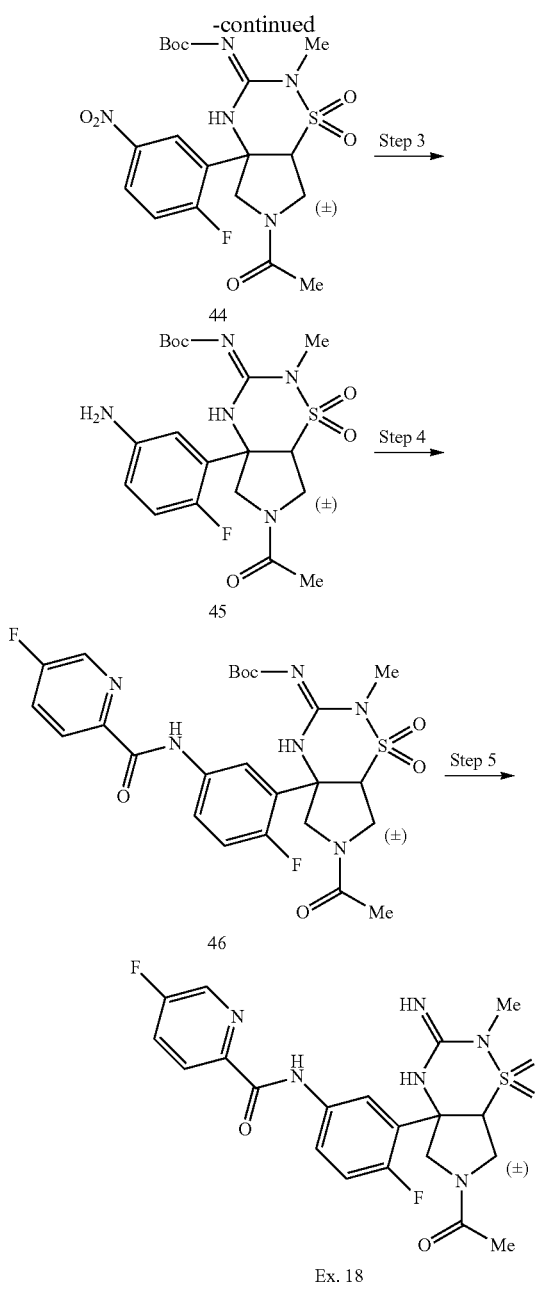

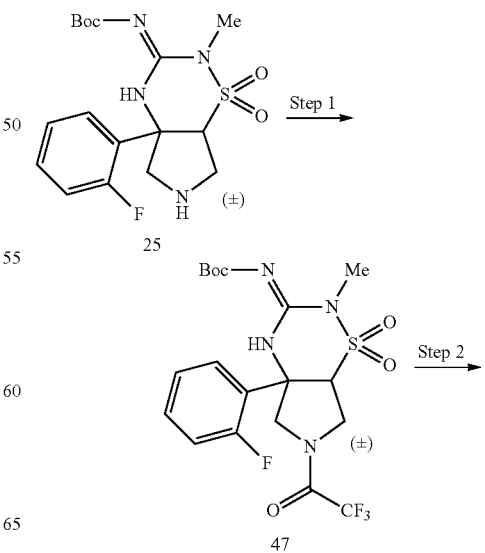

Ex. 18

Step 1

To 25 (0.10 g, 0.25 mmol) in pyridine (0.5 mL) was added acetic anhydride (0.036 mL, 0.28 mmol). The reaction was stirred at room temperature for 2.5 h and then concentrated in vacuo. The residue was taken up into EtOAc and water. The aqueous layer was extracted with EtOAc. The combined organic layers were washed with brine and dried ($MgSO_4$). The organic layer was filtered and concentrated in vacuo to provide 43 (0.085 g, 0.19 mmol) that was used directly in the next step.

Step 2

To 43 (0.10 g, 0.23 mmol) in sulfuric acid (0.2 mL) at 0° C. was added a mixture of fuming nitric acid (0.019 mL) and sulfuric acid (0.045 mL). The cold bath was taken away and the reaction stirred for 45 minutes. Ice and solid potassium carbonate was added to the reaction to basify to pH~10. The reaction mixture was extracted with EtOAc. The combined organic layers were washed with water and brine. The organic layer was dried ($MgSO_4$), filtered, and concentrated in vacuo to provide a pale yellow foam (0.085 g). The residue was taken up into DCM and di-tert-butyldicarbonate was added (0.075 g, 0.34 mmol). The reaction was stirred at room temperature for 16 h and then concentrated in vacuo. The residue was purified by preparative TLC (90% EtOAc/hex) to provide 44 (74 mg, 66%-2 steps).

Step 3

To 44 (66 mg, 0.14 mmol) in THF (0.8 mL) and water (0.08 mL) was added zinc powder (88 mg, 1.4 mmol) and ammonium chloride (36 mg, 0.7 mmol). The mixture was heated to reflux and stirred for 30 minutes and additional zinc powder (44 mg) and ammonium chloride (18 mg) was added. The reaction mixture was stirred at reflux for and additional 0.5 h and additional zinc powder (44 mg) and ammonium chloride (18 mg) and the reaction stirred at reflux for an additional 1 h. The reaction was cooled to room temperature and filtered through a bed of Celite, washing with methanol. The filtrate was concentrated in vacuo. The residue was taken up into EtOAc and saturated $NaHCO_3$. The aqueous layer was extracted with EtOAc. The combined organic layers were washed with water and brine. The organic layer was dried ($MgSO_4$), filtered, and concentrated in vacuo to provide 45 (28 mg, 44%) that was used directly in the next step.

Step 4

To 45 (28 mg, 0.06 mmol) in pyridine (0.5 mL) was added 5-fluoropyridine-2-carboxylic acid (13 mg, 0.09 mmol) and BOP-Cl (35 mg, 0.14 mmol). The reaction was stirred at room temperature for 16 h and then concentrated in vacuo. The residue was take up into EtOAc and water. The aqueous layer was extracted with EtOAc. The combined organic layers were washed with water and brine. The organic layer was dried ($MgSO_4$), filtered, and concentrated in vacuo. The residue was purified by preparative silica TLC (80% EtOAc/hex) to provide 46 (20 mg, 57%).

Step 5

To 46 (20 mg, 0.03 mmol) in DCM (0.5 mL) was added TFA (0.5 mL). The reaction was stirred at room temperature for 1 h and then concentrated in vacuo to provide Ex. 18 (20 mg) as the TFA salt.

Scheme 9

-continued

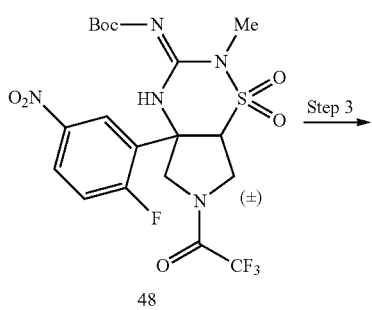

48

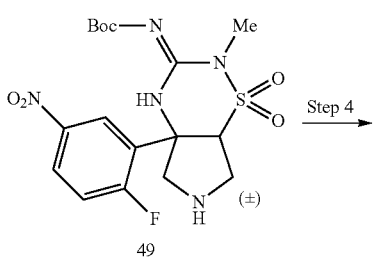

49

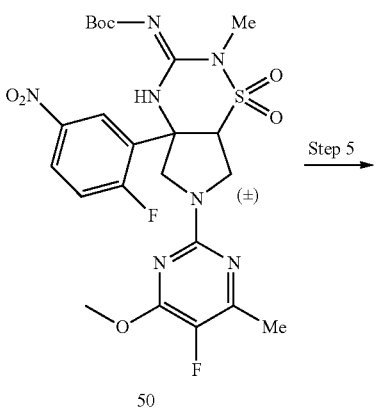

50

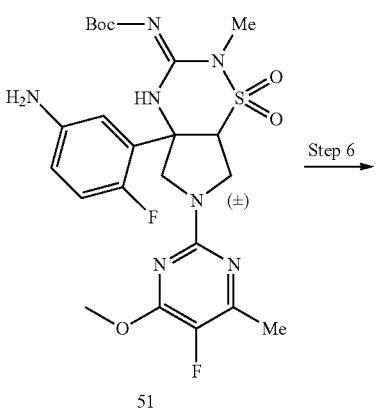

51

-continued

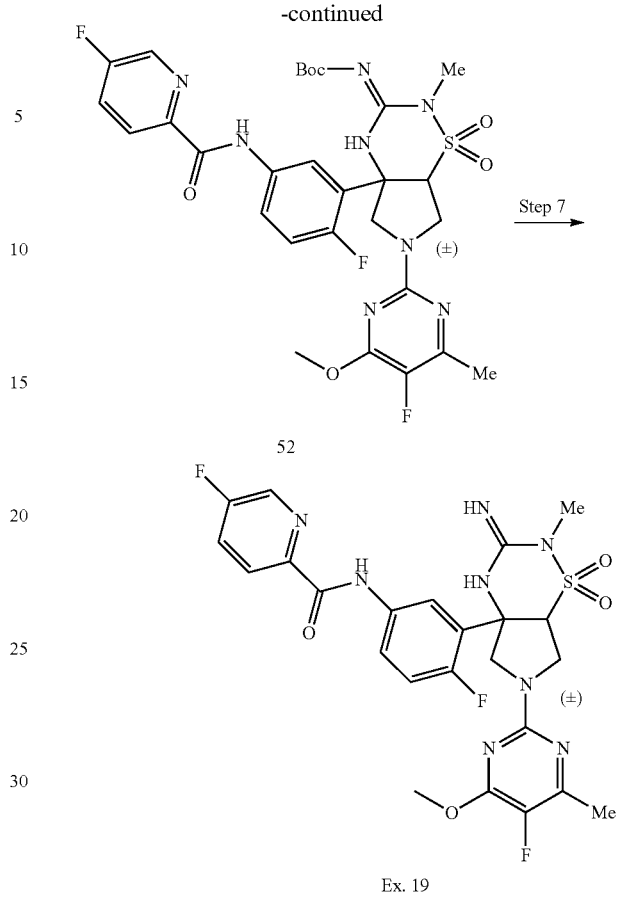

Step 1

To 25 (0.30 g, 0.75 mmol) in DCM (2.5 mL) at 0° C. was added pyridine (0.12 mL, 1.5 mmol) and trifluoroacetic anhydride. The reaction was stirred for 2 h and then DCM was added. The mixture was washed with 1:1 saturated NaHCO₃ (1:1 v/v saturated NaHCO₃/water), water, and brine. The organic layer was dried (MgSO₄), filtered, and concentrated in vacuo. The residue was purified by silica gel chromatography (0-30% EtOAc/hex over 30 minutes) to provide 47 (0.37 g, 100%).

Step 2

Using the conditions described in step 2 of scheme 8, 47 (0.37 g, 0.75 mmol) was converted to 48 (0.21 g, 52%—2 steps).

Step 3

To 48 (0.21 g, 0.38 mmol) in methanol (0.9 mL) was added water (0.3 ml) and potassium carbonate (120 mg). The reaction was stirred at room temperature for 1 h. The reaction was neutralized with saturated NH₄Cl. The methanol was removed in vacuo. The aqueous layer was extracted with EtOAc. The combined organic layers were washed with saturated NaHCO₃, water and brine. The organic layer was dried (MgSO₄), filtered, and concentrated in vacuo. The residue was purified by silica gel chromatography (0-100% EtOAc/hex over 25 minutes) to provide 49 (0.14 g, 83%).

Step 4

To 49 (55 mg, 0.12 mmol) in toluene (0.5 mL) was bubbled nitrogen gas for 5 minutes. To the reaction mixture was added 2-chloro-5-fluoro-4-methoxypyridine 29 (25 mg, 0.14 mmol), Pd(dba)₂ (3.4 mg, 0.006 mmol), 2-di-1-butylphosphino-2'-(N,N-dimethylamino) biphenyl (2.0 mg, 0.006 mmol), and sodium tert-butoxide (25 mg, 0.26 mmol). Nitrogen was bubbled through the reaction mixture for 5 minutes. The reaction mixture was heated to 65° C. and stirred for 3.5 h. The reaction mixture was cooled to room temperature and saturated NH$_4$Cl was added. The mixture was extracted with EtOAc. The combined organic layers were washed with water and brine. The organic layer was dried (MgSO$_4$), filtered, and concentrated in vacuo. The residue was purified by preparative silica gel TLC (30% EtOAc/hex) to provide 50 (32 mg, 46%).

Step 5

To 50 (60 mg, 0.10 mmol) in MeOH (5 mL) was added 1% platinum on carbon vanadium doped (50% wetted powder) Evonik F4 (available from Strem Chemicals) (12 mg). The reaction was put under hydrogen (40 psi) for 12 h. The reaction was filtered through a pad of Celite, washing with methanol. The filtrate was concentrated in vacuo to provide 51 (48 mg, 87%).

Step 6

To 51 (48 mg, 0.087 mmol) in pyridine (0.5 mL) was added 5-fluoropyridine-2-carboxylic acid (18 mg, 0.13 mmol) and BOP-Cl (51 mg, 0.20 mmol). The reaction mixture was stirred at room temperature for 1 h and then concentrated in vacuo. The residue was taken up into water and EtOAc. The aqueous layer was extracted with EtOAc. The combined organic layers were washed with water and brine. The organic layer was dried (MgSO$_4$), filtered, and concentrated in vacuo. The residue was purified by preparative silica gel TLC (30% EtOAc/hex) to provide 52 (26 mg, 44%).

Step 7

To 52 (26 mg, 0.038 mmol) in DCM (0.5 mL) was added TFA (0.5 mL). The reaction was stirred at room temperature for 30 minutes and then concentrated in vacuo. The residue was purified by reverse phase chromatography (C18 column: gradient elution 90:10:0.1 to 0:100:0.1 water:acetonitrile:formic acid) to provide Ex. 19 as the formate salt (15 mg, 63%).

ASSAYS

The protocol that was used to determine the recited potency values is described as follows.

BACE1 HTRF FRET Assay

Reagents

Na$^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay was used to determine IC$_{50}$ values for inhibitors of the soluble human BACE1 catalytic domain. This assay monitored the increase of 620 nm fluorescence that resulted from BACE1 cleavage of an APPswedish APP$^{swe}$ mutant peptide FRET substrate (QSY7-EISEVNLDAEFC-Europium-amide). This substrate contained an N-terminal QSY7 moiety that served as a quencher of the C-terminal Europium fluorophore (620 nm Em). In the absence of enzyme activity, 620 nm fluorescence was low in the assay and increased linearly over 3 hours in the presence of uninhibited BACE1 enzyme. Inhibition of BACE1 cleavage of the QSY7-APP$^{swe}$-Eu substrate by inhibitors was manifested as a suppression of 620 nm fluorescence.

Varying concentrations of inhibitors at 3× the final desired concentration in a volume of 10 ul were preincubated with purified human BACE1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions were initiated by addition of 10 µl of 600 nM QSY7-APP$^{swe}$-Eu substrate (200 nM final) to give a final reaction volume of 30 µl in a 384 well Nunc HTRF plate. The reactions were incubated at 30° C. for 1.5 hours. The 620 nm fluorescence was then read on a Rubystar HTRF plate reader (BMG Labtechnologies) using a 50 □s delay followed by a 400 millisecond acquisition time window. Inhibitor IC$_{50}$ values were derived from non-linear regression analysis of concentration response curves. K$_i$ values were then calculated from IC$_{50}$ values using the Cheng-Prusoff equation using a previously determined µm value of 8 µM for the QSY7-APP$^{swe}$-Eu substrate at BACE1.

BACE-2 Assay

Inhibitor IC$_{50s}$ at purified human autoBACE-2 were determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO were pre-incubated with an equal volume of autoBACE-2 enzyme diluted in 1×BACE assay buffer (final enzyme concentration 1 nM) in black 384-well NUNC plates for 30 minutes at 30° C. The assay was initiated by addition of an equal volume of the QSY7-EISEV NLDAEFC-Eu-amide substrate (200 nM final concentration, K$_m$=8 µM for 4 µM for autoBACE-2) prepared in 1×BACE assay buffer supplemented with 7.5% DMSO and incubated for 90 minutes at 30° C. DMSO was present at 5% final concentration in the assay. Following laser excitation of sample wells at 320 nm, the fluorescence signal at 620 nm was collected for 400 ms following a 50 µs delay on a RUBYstar HTRF plate reader (BMG Labtechnologies). Raw RFU data was normalized to maximum (1.0 nM BACE/DMSO) and minimum (no enzyme/DMSO)RFU values. IC$_{50s}$ were determined by nonlinear regression analysis (sigmoidal dose response, variable slope) of percent inhibition data with minimum and maximum values set to 0 and 100 percent respectively. Similar IC$_{50s}$ were obtained when using raw RFU data. The K$_i$ values were calculated from the IC$_{50}$ using the Cheng-Prusoff equation.

BACE Inhibitor Whole Cell IC50 Determination Using HEK293-APP$^{swe/lon}$ Cells

HEK293 cells were obtained from the American Type Culture Collection (ATCC) and stably transfected with the human amyloid precursor protein cDNA containing the FAD Swedish (enhances β-secretase processing) and London (enhances Aβ42 cleavage) mutations. A HEK293 stable clone with Aβ expression (HEK293-APP$^{swe/lon}$) was identified and maintained at 37° C., 5% CO$_2$ in the ATCC-recommended growth media supplemented with hygromycin. Determination of compound IC$_{50}$ values for inhibition of APP processing (reduction of Aβ1-40, Aβ1-42 and sAPPβ levels) in HEK293-APP$^{swe/lon}$ cells was accomplished by treatment of cells with various concentrations of compounds diluted in fresh complete growth media for 4 hours at 37° C., 5% CO$_2$. Aβ40 or Aβ42 were measured in 15 µl of media using a mesoscale based ELISA assay. Full length Aβ40 and Aβ42 peptides were captured with the N-terminal specific biotinylated-WO2 monoclonal antibody and detected using either the ruthenylated Aβ40 C-terminal specific monoclonal antibody, G2-10 or the ruthenylated Aβ42 C-terminal specific monoclonal antibody G2-11 respectively. Raw electrochemiluminescnce values were measured using a Mesoscale Sector Imager plate reader and were plotted as a function of compound concentration. IC$_{50}$ values were interpolated from the data using nonlinear regression analysis (Sigmoidal dose response fit with variable slope) of the data using GraphPad Prism software.

LC/MS Contitions
Method A:
Column: Gemini C-18, 50×4.6 mm, 5 micron, obtained from Phenomenex.
  Mobile phase: A: 0.05% Trifluoroacetic acid in water
  B: 0.05% Trifluoroacetic acid in acetonitrile
  Gradient: 90:10 to 5:95 (A:B) over 5 min.
Flow rate: 1.0 mL/min; UV detection: 254 nm
ESI-MS: Electro Spray Ionization Liquid chromatography-mass spectrometry (ESI-LC/MS) was performed on a PE SCIEX API-150EX, single quadrupole mass spectrometer.
Method B:
Column: Agilent Zorbax SB-C18 (3.0×50 mm) 1.8 uM
  Mobile phase: A: 0.05% Trifluoroacetic acid in water
  B: 0.05% Trifluoroacetic acid in acetonitrile
  Gradient: 90:10 (A:B) for 0.3 min, 90:10 to 5:95 (A:B) over 1.2 min, 5:95 (A:B) for 1.2 min.
Flow rate: 1.0 mL/min
UV detection: 254 and 220 nm
Mass spectrometer Agilent 6140 quadrupole.

Table 4 sets forth non-limiting examples of compounds of the invention. Esters, prodrugs, solvates, and tautomers of these compounds, and salts (including pharmaceutically acceptable salts) of said compounds, esters, prodrugs, solvates, and tautomers thereof, are also included within the scope of the invention. The compounds of the examples, set forth in the table below, were synthesized using the appropriate intermediates and essentially the procedures described in the methods above.

TABLE 4

| Ex. No. | structure | BACE-1 Ki (nM) | BACE-2 Ki (nM) | LC/MS conditions | [M + H] observed | retention time (min.) |
|---|---|---|---|---|---|---|
| 1 | 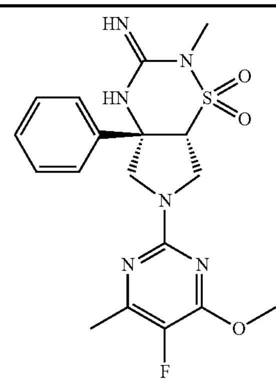 | 51 | 16 | A | 421.2 | 2.99 |
| 2 | 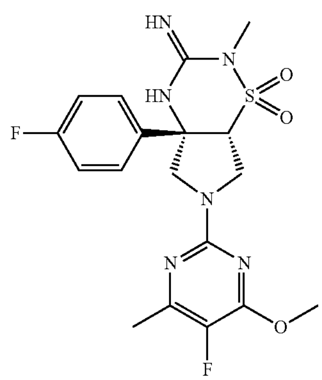 [SMILES: COc1nc(N2C[C@@H]3[C@](c4ccc(F)cc4)(C2)NC(=N)N(C)S3(=O)=O)nc(C)c1F] | 35 | 14 | A | 439.2 | 3.10 |
| 3 | 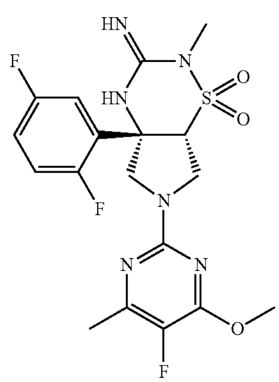 [SMILES: COc1nc(N2C[C@@H]3[C@](c4cc(F)ccc4F)(C2)NC(=N)N(C)S3(=O)=O)nc(C)c1F] | 20 | 14 | A | 457.3 | 3.91 |

TABLE 4-continued

| Ex. No. | structure | BACE-1 Ki (nM) | BACE-2 Ki (nM) | LC/MS conditions | [M + H] observed | retention time (min.) |
|---|---|---|---|---|---|---|
| 4 | 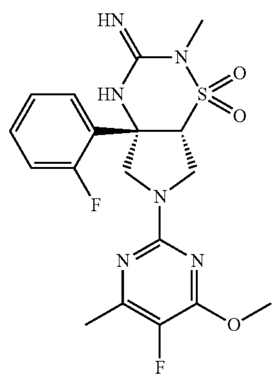 [SMILES: COc1nc(N2C[C@@H]3[C@](c4ccccc4F)(C2)NC(=N)N(C)S3(=O)=O)nc(C)c1F] | 19 | 5.4 | A | 439.2 | 3.82 |
| 5 | 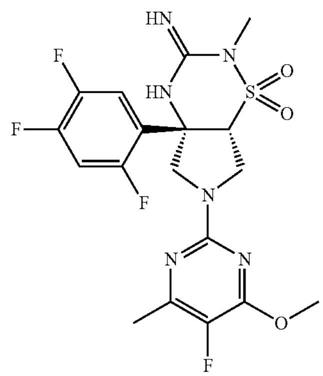 [SMILES: COc1nc(N2C[C@@H]3[C@](c4cc(F)c(F)cc4F)(C2)NC(=N)N(C)S3(=O)=O)nc(C)c1F] | 32 | 19 | B | 475.0 | 1.94 |
| 6 | 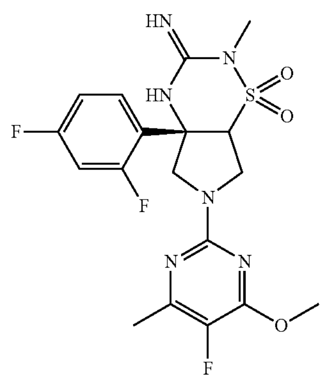 [SMILES: COc1nc(N2CC3[C@](c4ccc(F)cc4F)(C2)NC(=N)N(C)S3(=O)=O)nc(C)c1F] | 30 | 8.5 | A | 457.3 | 3.96 |
| 7 | 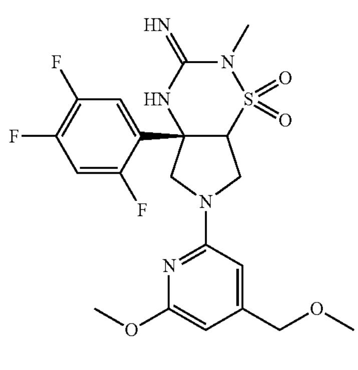 [SMILES: COCc1cc(OC)nc(N2CC3[C@](c4cc(F)c(F)cc4F)(C2)NC(=N)N(C)S3(=O)=O)c1] | 7 | 3.2 | B | 486.0 | 1.92 |

TABLE 4-continued

| Ex. No. | structure | BACE-1 Ki (nM) | BACE-2 Ki (nM) | LC/MS conditions | [M + H] observed | retention time (min.) |
| --- | --- | --- | --- | --- | --- | --- |
| 8 | 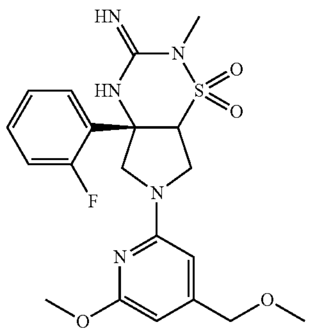 [SMILES: COCc1cc(OC)nc(N2CC3[C@](c4ccccc4F)(C2)NC(=N)N(C)S3(=O)=O)c1] | 7 | 5.0 | B | 450.2 | 1.90 |
| 9 | 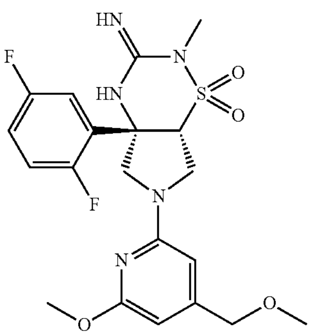 [SMILES: COCc1cc(OC)nc(N2C[C@@H]3[C@](c4cc(F)ccc4F)(C2)NC(=N)N(C)S3(=O)=O)c1] | 10 | 1.7 | B | 468.0 | 1.91 |
| 10 | 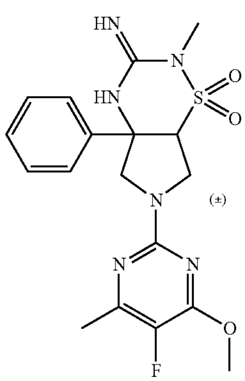 [SMILES: COc1nc(N2CC3C(c4ccccc4)(C2)NC(=N)N(C)S3(=O)=O)nc(C)c1F] | 93 | 57 | A | 421.2 | 3.02 |
| 11 | 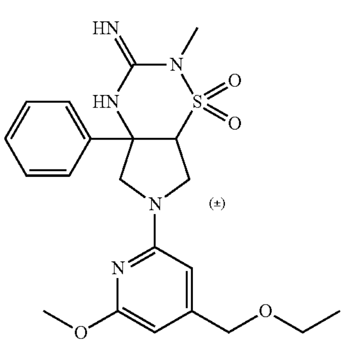 [SMILES: CCOCc1cc(OC)nc(N2CC3C(c4ccccc4)(C2)NC(=N)N(C)S3(=O)=O)c1] | 61 | 6.7 | A | 446.2 | 2.31 |

TABLE 4-continued
| Ex. No. | structure | BACE-1 Ki (nM) | BACE-2 Ki (nM) | LC/MS conditions | [M + H] observed | retention time (min.) |
|---|---|---|---|---|---|---|
| 12 | 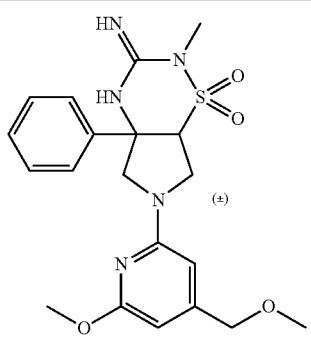 [SMILES: COCc1cc(OC)nc(N2CC3C(c4ccccc4)(C2)NC(=N)N(C)S3(=O)=O)c1] | 27 | 6.4 | A | 432.2 | 2.13 |
| 13 | 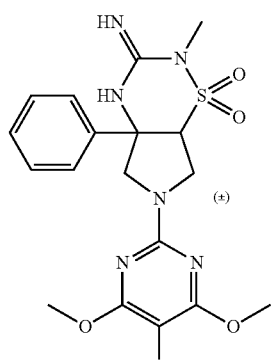 | 30 | 10 | A | 437.2 | 4.63 |
| 14 | 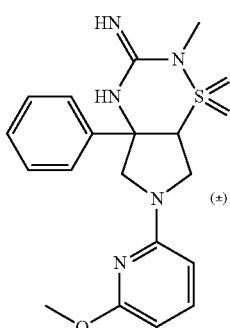 | 86 | 26 | B | 388.0 | 1.85 |
| 15 | 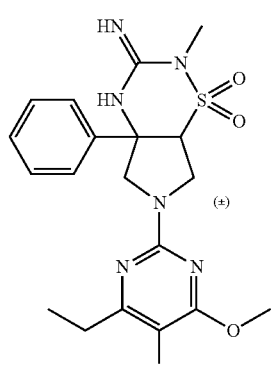 | 82 | 21 | B | 435.2 | 1.96 |

TABLE 4-continued

| Ex. No. | structure | BACE-1 Ki (nM) | BACE-2 Ki (nM | LC/MS conditions | [M + H] observed | retention time (min.) |
|---|---|---|---|---|---|---|
| 16 | 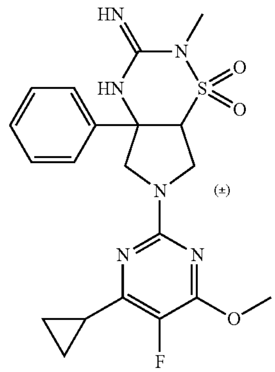 [SMILES: COc1nc(N2CC3C(c4ccccc4)(C2)NC(=N)N(C)S3(=O)=O)nc(C2CC2)c1F] | 42 | 5.7 | B | 447.2 | 1.99 |
| 17 | 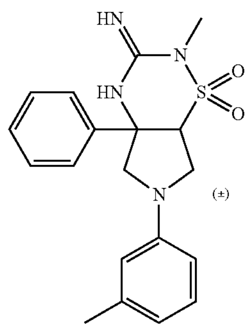 [SMILES: Cc1cccc(N2CC3C(c4ccccc4)(C2)NC(=N)N(C)S3(=O)=O)c1] | 1563 | 890 | B | 371.2 | 1.91 |
| 18 | 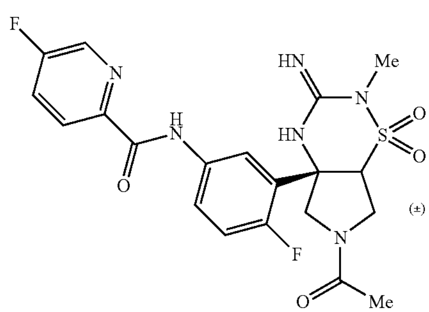 [SMILES: CC(=O)N1CC2[C@](c3cc(NC(=O)c4ccc(F)cn4)ccc3F)(C1)NC(=N)N(C)S2(=O)=O] | 32 | 3.2 | B | 479.0 | 1.73 |
| 19 | 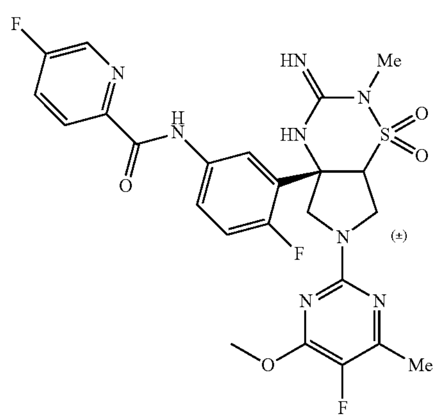 [SMILES: COc1nc(N2CC3[C@](c4cc(NC(=O)c5ccc(F)cn5)ccc4F)(C2)NC(=N)N(C)S3(=O)=O)nc(C)c1F] | 1.2 | 1.6 | B | 577.0 | 2.03 |

Bi-Directional Permeability

It has been found, surprisingly and advantageously, that thiadiazine dioxide compounds of the invention exhibit reduced susceptibility to efflux by P-glycoprotein (P-gp), as indicated by the relatively lower human MDR1 (BA/AB ratio) shown in the table below, when compared to otherwise structurally identical iminopyrimidinones. P-gp is found, among other locations, at the blood-brain barrier. Reduced susceptibility of the compounds of the invention to efflux by this protein is regarded as a desirable characteristic, associated with improved expected exposure to target sites for centrally acting compounds. (A. Schinkel, *Advanced Drug Delivery Reviews* 1999, 36, 179-194). The following procedures were used. Results are shown below.

Method

Bi-directional transport was evaluated in LLC-PK1 cells and in LLC-PK1 cells stably transfected with a human MDR1 or rat Mdr1a cDNAs, which encode the human and rat multidrug resistance P-glycoproteins (Pgp), respectively. The transfected cell lines are called LLC-MDR1 and LLC-rMdr1a, respectively. LLC-PK1 derived cell lines can form a tight monolayer and therefore can be used to assess vectorial transport of compounds from basolateral to apical (B→A) and from apical to basolateral (A→B).

To determine if a compound was a substrate of human and rat Pgp, LLC-PK1, LLC-MDR1 and LLC-rMdr1a cell lines were cultured in 96-well transwell culture plates (Millipore). Solutions containing the test compounds were prepared in Hank's Balanced Salt Solution with 10 mM HEPES. Substrate solution (150 µL) was added to either the apical (A) or the basolateral (B) compartment of the culture plate, and buffer (150 µL) was added to the compartment opposite to that containing the compound. At t=3 hr, 50 µL samples were removed from both sides of monolayers dosed with test compound and placed in 96 well plates, scintillant (200 µL) or internal standard (100 µL labetolol 1 µM) was added to the samples and concentration was determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 µM) was used as the positive control. The experiment was performed in triplicate.

The $P_{app}$ was calculated by the following formula for samples taken at t=3 hr:

$$P_{app} = \frac{\text{Volume of Receptor Chamber (mL)}}{[\text{Area of membrane (cm}^2)][\text{Initial Concentration (}\mu\text{M)}]} \times \frac{\Delta \text{ in Concentration (}\mu\text{M)}}{\Delta \text{ in Time (s)}}$$

Where: Volume of Receptor Chamber was 0.15 mL; Area of membrane was 0.11 cm$^2$; the Initial Concentration is the sum of the concentration measured in the donor plus concentration measured in receiver compartments at t=3 h; $\Delta$ in Concentration is concentration in the receiver compartment at 3 hr; and $\Delta$ in Time is the incubation time (3×60×60=10800 s). $P_{app}$ was expressed as $10^{-6}$ cm/s. The $P_{app}$ (LLC-PK1 cells) are the average of the $P_{app}$ for transport from A to B and $P_{app}$ for transport from B to A at t=3 hr:

$$P_{app}(LLC-PK1 \text{ Cells}) = \frac{P_{app}(A \to B) + P_{app}(B \to A)}{2}$$

The $P_{app}$ B→A/A→B ratios were calculated by dividing the $P_{app}$ from B to A by the $P_{app}$ from $$A \text{ to } B \text{ at } t = 3 \text{ hr: } P_{app} \text{ } B \to A/A \to B \text{ Ratio} = \frac{P_{app}(B \to A)}{P_{app}(A \to B)}$$

| Compound ID | Example | Structure | Human MDR1 (BA/AB ratio) |
|---|---|---|---|
| Thiadiazine Dioxide | Ex. 10 | 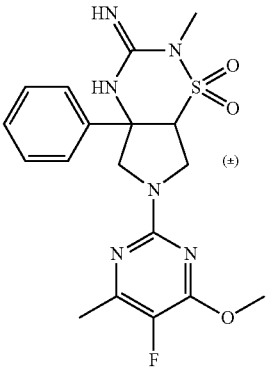 [SMILES: COc1nc(N2CC3C(c4ccccc4)(C2)NC(=N)N(C)S3(=O)=O)nc(C)c1F] | 5.4 |
| Iminopyrimidinone | WO 2009131975 Racemate of enantiomer shown in Ex. 12 | 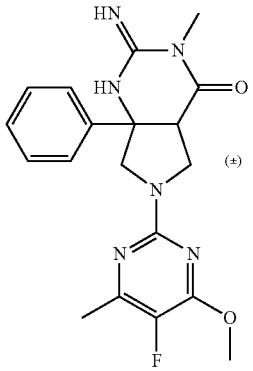 [SMILES: COc1nc(N2CC3C(=O)N(C)C(=N)NC3(c3ccccc3)C2)nc(C)c1F] | 26 |

-continued

| Compound ID | Example | Structure | Human MDR1 (BA/AB ratio) |
|---|---|---|---|
| Thiadiazine Dioxide | Ex. 2 | | 2.2 |
| Iminopyrimidinone | WO 2009131975 Racemate of enantiomer shown in Ex. 17 | | 24 |
| Thiadiazine Dioxide | Ex. 6 | | 1.6 |
| Iminopyrimidinone | WO 2009131975 Ex. 20 | | 7.7 |

-continued

| Compound ID | Example | Structure | Human MDR1 (BA/AB ratio) |
|---|---|---|---|
| Thiadiazine Dioxide | Ex. 3 | | 1.2 |
| Iminopyrimidinone | WO 2009131975 Ex. 15 | | 6.0 |
| Thiadiazine Dioxide | Ex. 4 | | 1.5 |
| Iminopyrimidinone | WO 2009131975 Racemate of enantiomer shown in Ex. 16 | | 12 |

| Compound ID | Example | Structure | Human MDR1 (BA/AB ratio) |
|---|---|---|---|
| Thiadiazine Dioxide | Ex. 9 | 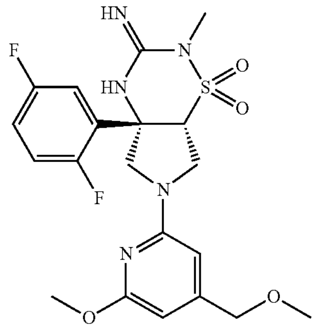 [SMILES: COCc1cc(OC)nc(N2C[C@@H]3[C@](c4cc(F)ccc4F)(C2)NC(=N)N(C)S3(=O)=O)c1] | 2.4 |
| Iminopyrimidinone | WO 2009131975 N-arylation of E9 (with cmpd 35 as coupling partner) | 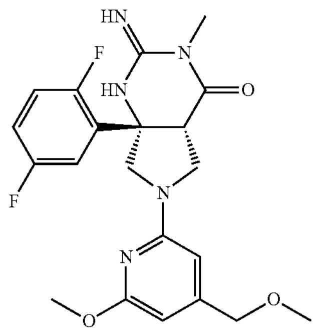 [SMILES: COCc1cc(OC)nc(N2C[C@H]3C(=O)N(C)C(=N)N[C@@]3(c3cc(F)ccc3F)C2)c1] | 22 |

Solution Stability

The imino thiadiazine dioxide compounds of the invention have also been found, surprisingly and advantageously, to exhibit better solution stability (e.g., by resistance to hydrolysis) compared with structurally similar imino pyrimidinones. In the following study, the solution stability of the thiadiazine dioxide compound of Example 10, a compound of the invention, was measured and compared to that of the otherwise structurally analogous iminopyrimidinone shown in Example 12 of WO200913197. The structures of these two compounds are as follows:

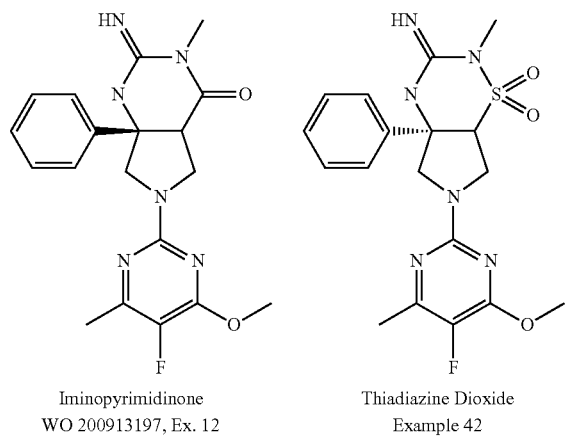 [SMILES: COc1nc(N2CC3C(=O)N(C)C(=N)N[C@@]3(c3ccccc3)C2)nc(C)c1F ; COc1nc(N2CC3[C@@](c4ccccc4)(C2)NC(=N)N(C)S3(=O)=O)nc(C)c1F]

Iminopyrimidinone
WO 200913197, Ex. 12

Thiadiazine Dioxide
Example 42

Procedure

Stock solutions of each of the test compounds were prepared by dissolving about 3 mg of each compound in 3 mL of acetonitrile. Standards for test compounds were prepared by diluting 1 mL of the stock solution with an additional 4 mL of acetonitrile and stored 4° C. Samples were prepared by diluting 1 mL of the stock solution with 4 mL of 50 mM pH 7.4 phosphate buffer. These samples were stored at ambient room temperature in the absence of light. Standards and samples were analyzed by LC/MS initially and at day 1 and day 5.

HPLC Conditions:

System: Agilent LC1200 with DAD

Mobile Phase A: 25 mM ammonium acetate, acetic acid pH 5/MeOH (90:10)

Mobile Phase B: 25 mM ammonium acetate, acetic acid pH 5/MeOH (10:90)

Column: Gemini-NX C18, 3 micron, 50×4.6 mm

Column temperature: 50 deg C.

Gradient

| Time (min.) | % B |
|---|---|
| 0 | 10 |
| 10 | 100 |

UV Detection: 235 nm

Injection: 5 uL

Flow rate: 0.8 mL/min

Run time: 10 min

Post time: 3 min

Area % is the integration of peak from HPLC.

| Solution Stability for the Iminopyrimidinone of Example 12, WO200913197 in pH 7.4: | | | |
|---|---|---|---|
| Condition | Ambient temperature | | |
| Time, days | Initial | 1 | 5 |
| Assay (Area %) | 91.8 | 89.7 | 51.9 |
| Solution Stability for the Thiadiazine dioxide of Example 42 in pH 7.4: | | | |
| Condition | Initial | 1 | 5 |
| Time, days | | | |
| Assay (Area %) | 86.8 | 86.9 | 87.1 |

We claim:

1. A compound, or a stereoisomer of said compound, or a pharmaceutically acceptable salt of said compound or said stereoisomer, said compound having the structural Formula (I):

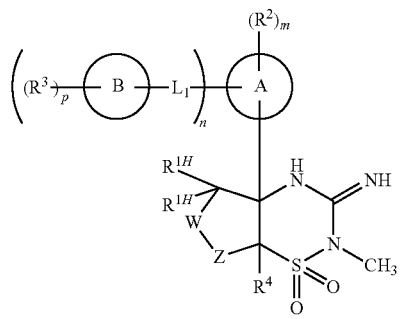

or its tautomeric form, Formula (I'):

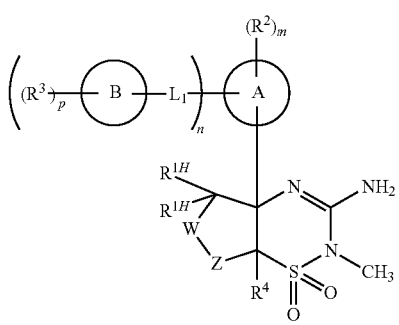

wherein:
one of W and Z is $C(R^{1H})_2$ and the other is $N(R^1)$;
ring A is selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;
each ring B (when present) is independently selected from the group consisting of monocyclic aryl, monocyclic heteroaryl, monocyclic cycloalkyl, monocyclic cycloalkenyl, monocyclic heterocycloalkyl, monocyclic heterocycloalkenyl, and a multicyclic group;
m, n, and p are each independently selected integers, wherein:
m is 0 or more;
n is 0 or 1; and
p is 0 or more,
wherein the maximum value of m is the maximum number of available substitutable hydrogen atoms on ring A, and wherein the maximum value of p is the maximum number of available substitutable hydrogen atoms on ring B;
-$L_1$- (when present) independently represents a bond or a divalent moiety selected from the group consisting of -alkyl-, -haloalkyl-, -heteroalkyl-, -alkenyl-, -alkynyl-, —N($R^6$)—, —NHC(O)—, —C(O)NH—, NHS(O)$_2$—, —S(O)$_2$NH—, —O—CH$_2$—, —CH$_2$—O—, —NHCH$_2$—, —CH$_2$NH—, and —CH(CF$_3$)NH—;
$R^1$ is selected from the group consisting of: H, —C(O)$R^6$, —C(O)$_2R^6$, —C(O)N($R^6$)$_2$, —C(=NO$R^7$)$R^6$, —S(O)$R^6$, —S(O)$_2R^6$, —S(O)$_2$N($R^6$)$_2$, alkyl, haloalkyl, heteroalkyl, alkenyl, alkynyl, phenyl, monocyclic heteroaryl, monocyclic cycloalkyl, and monocyclic heterocycloalkyl, wherein said alkyl, said haloalkyl, said heteroalkyl, said alkenyl, said alkynyl, said phenyl, said monocyclic heteroaryl, said monocyclic cycloalkyl, and said monocyclic heterocycloalkyl of R' is optionally unsubstituted or substituted with one or more groups independently selected from $R^8$;
each $R^{1H}$ is independently selected from the group consisting of: H, halogen, —OH, —CN, —SF$_5$, —OSF$_5$, —Si($R^5$)$_3$, —N($R^6$)$_2$, —NR$^7$C(O)$R^6$, —NR$^7$S(O)$_2R^6$, —NR$^7$C(O)N($R^6$)$_2$, —NR$^7$C(O)O$R^6$, —O$R^6$, —S$R^6$, —C(O)$R^6$, —C(O)$_2R^6$, —C(O)N($R^6$)$_2$, —P(O)(O$R^5$)$_2$, —P(O)(O$R^5$)($R^5$), —S(O)$R^6$, —S(O)$_2R^6$, —S(O)$_2$N($R^6$)$_2$, alkyl, haloalkyl, heteroalkyl, alkenyl, alkynyl, aryl, -alkyl-aryl, monocyclic heteroaryl, -alkyl-(monocyclic heteroaryl), monocyclic cycloalkyl, -alkyl-(monocyclic cycloalkyl), monocyclic heterocycloalkyl, a multicyclic group, and -alkyl-(multicyclic group);
wherein said alkyl, said haloalkyl, said heteroalkyl, said alkenyl, said alkynyl, said aryl, said -alkyl-aryl, said monocyclic heteroaryl, said alkyl-(monocyclic heteroaryl), said monocyclic cycloalkyl, said -alkyl-(monocyclic cycloalkyl), and said monocyclic heterocycloalkyl, said multcyclic group, and said -alkyl-(multicyclic group) of $R^{1H}$ is optionally unsubstituted or substituted with one or more groups independently selected from $R^8$;
each $R^2$ (when present) is independently selected from the group consisting of: halogen, —OH, —CN, —SF$_5$, —OSF$_5$, —NO$_2$, —Si($R^5$)$_3$, —P(O)(O$R^5$)$_2$, —P(O)(O$R^5$)($R^5$), —N($R^6$)$_2$, —NR$^7$C(O)$R^6$, —NR$^7$S(O)$_2R^6$, —NR$^7$C(O)N($R^6$)$_2$, —NR$^7$C(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;
each $R^3$ (when present) is independently selected from the group consisting of: halogen, —OH, —CN, —SF$_5$, —OSF$_5$, —NO$_2$, —Si($R^5$)$_3$, —P(O)(O$R^5$)$_2$, —P(O)(O$R^5$)($R^5$), —N($R^6$)$_2$, —NR$^7$C(O)$R^6$, —NR$^7$S(O)$_2R^6$, —NR$^7$C(O)N($R^6$)$_2$, —NR$^7$C(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^2$ are each optionally unsubstituted or substituted with one or more groups independently selected from $R^8$;

$R^4$ is selected from the group consisting of H, halogen, optionally substituted alkyl, optionally substituted heteroalkyl, optionally substituted -alkyl-cycloalkyl, optionally substituted -alkyl-aryl, and optionally substituted -alkyl-heteroaryl, wherein said optional substituents are each independently selected from $R^8$;

each $R^5$ (when present) is independently selected from the group consisting of H, alkyl, aryl, arylalkyl-, haloalkyl, cycloalkyl, -alkyl-cycloalkyl, heteroaryl, and heteroarylalkyl-;

each $R^6$ (when present) is independently selected from the group consisting of H, alkyl, alkenyl, heteroalkyl, -heteroalkyl-OH, haloalkyl, -haloalkyl-OH, cycloalkyl, lower alkyl- substituted cycloalkyl, lower alkyl-substituted -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^6$ is unsubstituted or substituted with one or more groups independently selected from halogen, alkyl, heteroalkyl, haloalkyl, alkoxy, heteroalkoxy, and haloalkoxy;

each $R^7$ (when present) is independently selected from the group consisting of H, alkyl, cycloalkyl, -alkyl-cycloalkyl, aryl, -alkyl-aryl, heteroaryl, and -alkyl-heteroaryl; and each $R^8$ (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH;

wherein each said multicyclic group (when present) is selected from the group consisting of bicyclic aryl, bicyclic heteroaryl, bicyclic cycloalkyl, bicyclic cycloalkenyl, bicyclic heterocycloalkyl, bicyclic heterocycloalkenyl, tricyclic aryl, tricyclic heteroaryl, tricyclic cycloalkyl, tricyclic cycloalkenyl, tricyclic heterocycloalkyl, and tricyclic heterocycloalkenyl.

2. A compound of claim 1, or a stereoisomer of said compound, or a pharmaceutically acceptable salt of said compound or said stereoisomer, said compound having the structural Formula (II):

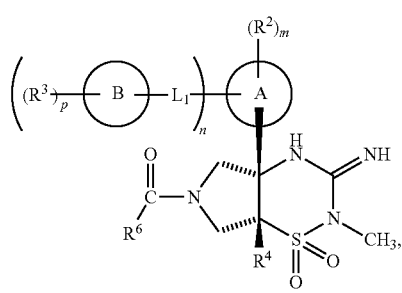

(II)

or its tautomeric form, Formula (II'):

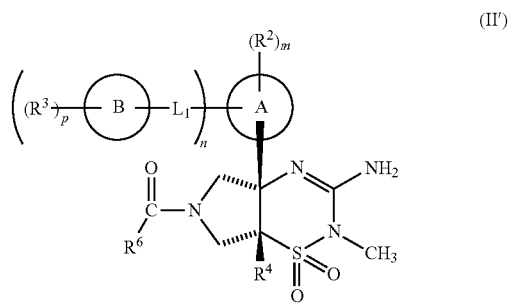

(II')

wherein:
$R^6$ is selected from the group consisting of H, alkyl, alkenyl, -heteroalkyl, haloalkyl, cycloalkyl, cycloalkylalkyl-, aryl, and heteroaryl.

3. A compound of claim 2, or a stereoisomer of said compound, or a pharmaceutically acceptable salt of said compound or said stereoisomer, wherein:
$R^6$ is lower alkyl.

4. A compound of claim 1, or a stereoisomer of said compound, or a pharmaceutically acceptable salt of said compound or said stereoisomer, said compound having the structural Formula (III):

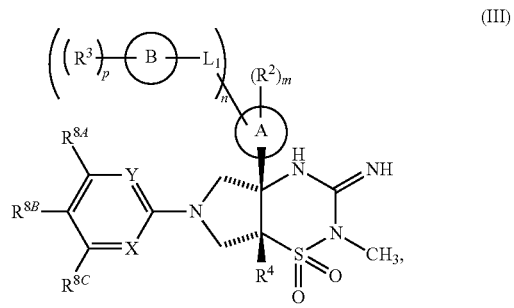

(III)

or its tautomeric form, Formula (HP):

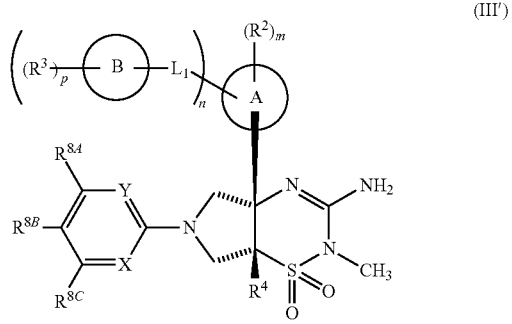

(III')

wherein:
X is N or CH;
Y is N or CH; and
$R^{8A}$, $R^{8B}$, and $R^{8C}$ are each independently selected from the group consisting of H, fluorine, chlorine, lower alkyl, lower alkoxy, lower haloalkyl, lower haloalkoxy, lower alkyl-OH, cycloalkyl, -alkyl-cycloalkyl, —O-cycloalkyl, —O-alkyl-cycloalkyl, lower heteroalkyl, and lower —O-heteroalkyl.

5. A compound of claim 4, or a stereoisomer of said compound, or a pharmaceutically acceptable salt of said compound or said stereoisomer, wherein:

$R^{8A}$ is selected from lower alkyl, lower alkoxy, lower haloalkyl, lower heteroalkyl, cyclopropyl, and -lower-alkyl-cyclopropyl;

$R^{8B}$ is selected from H, fluorine and chlorine; and $R^{8C}$ is selected from lower alkyl, lower alkoxy, lower haloalkyl, lower heteroalkyl, cyclopropyl, and -lower-alkyl-cyclopropyl.

6. A compound of claim 4, or a stereoisomer of said compound, or a pharmaceutically acceptable salt of said compound or said stereoisomer, wherein the moiety:

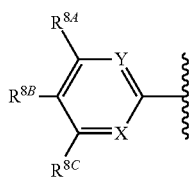

is selected from the group consisting of:

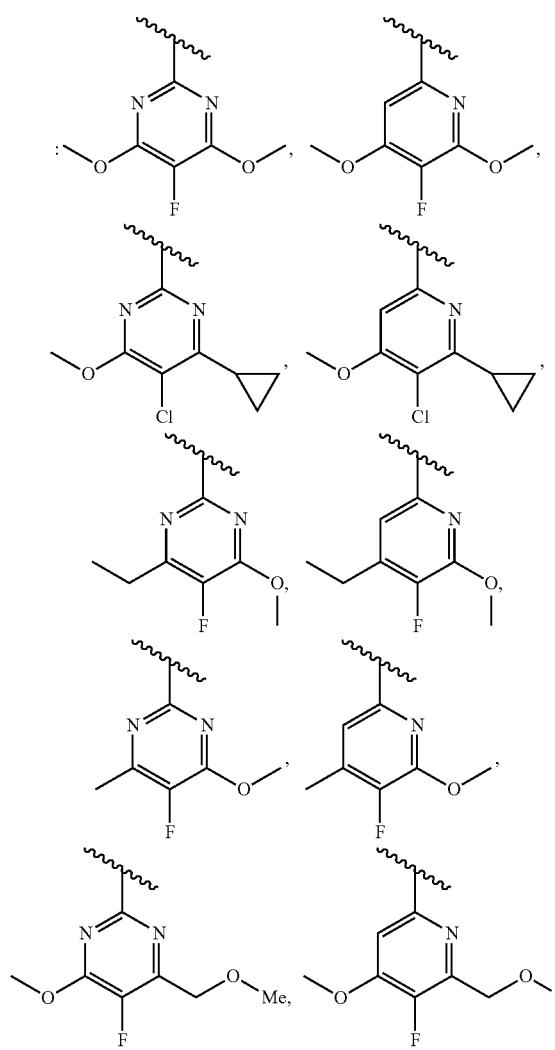

-continued

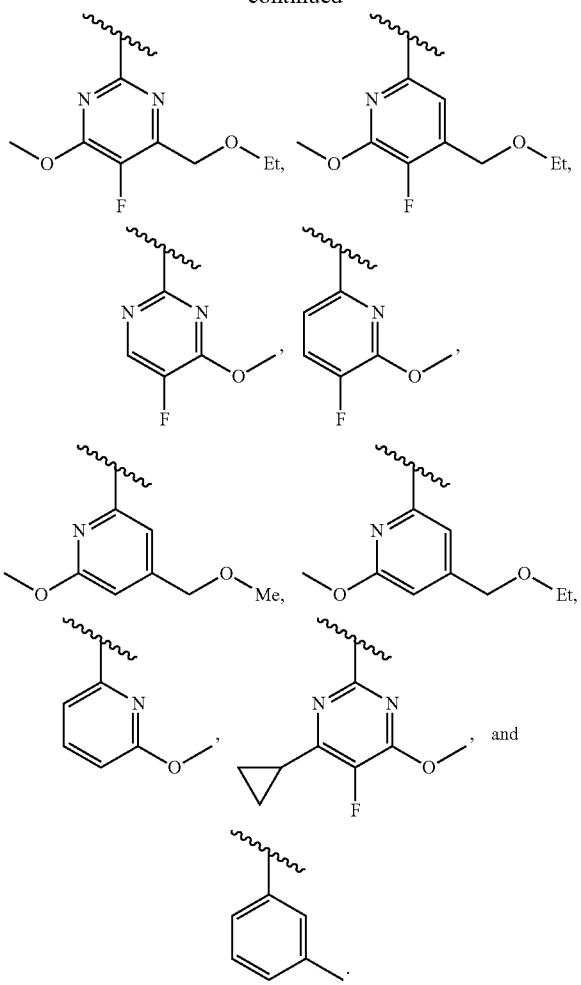

7. A compound according to any one of claims 1-6, or a stereoisomer of said compound, or a pharmaceutically acceptable salt of said compound or said stereoisomer, wherein:

n is 0;

ring A is phenyl;

m is 0 to 4; and each $R^2$ group (when present) is independently selected from the group consisting of halogen, —CN, —SF$_5$, —NH$_2$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

8. A compound of claim 7, or a stereoisomer of said compound, or a pharmaceutically acceptable salt of said compound or said stereoisomer, wherein the moiety:

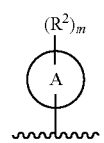

is selected from the group consisting of:

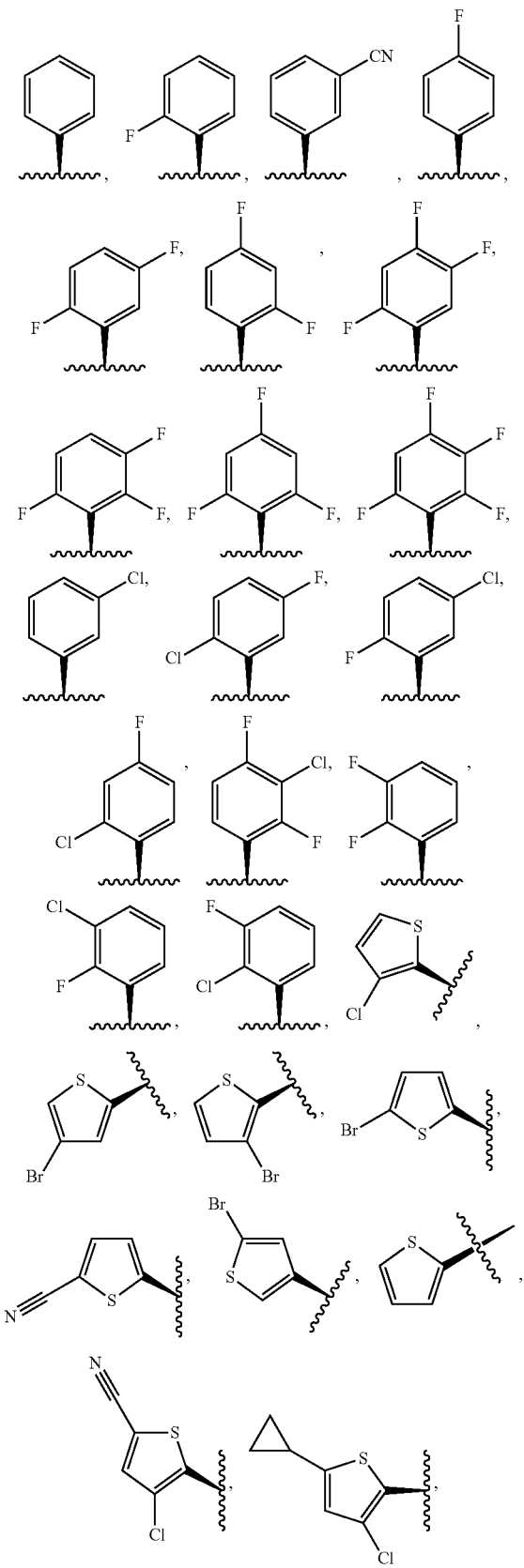

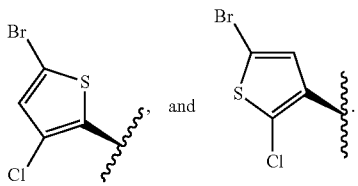

9. A compound according to any one of claims 1-6, or a stereoisomer of said compound, or a pharmaceutically acceptable salt of said compound or said stereoisomer, wherein:

n is 1;

ring A is selected from the group consisting of phenyl, thienyl, and pyridyl;

m is 0 or 1;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$;

-L$_1$- is a bond or a divalent moiety selected from the group consisting of —NHC(O)— and —C(O)NH—;

ring B is selected from the group consisting of phenyl, monocyclic heterocycloalkyl, and monocyclic heteroaryl;

p is 0 or more; and each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

10. A compound of claim 1, or a stereoisomer of said compound, or a pharmaceutically acceptable salt of said compound or said stereoisomer, selected from the group consisting of:

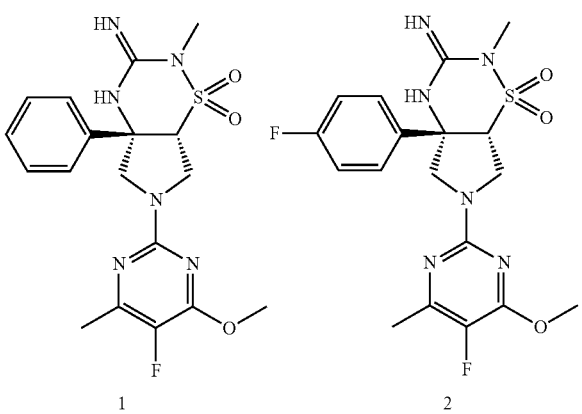

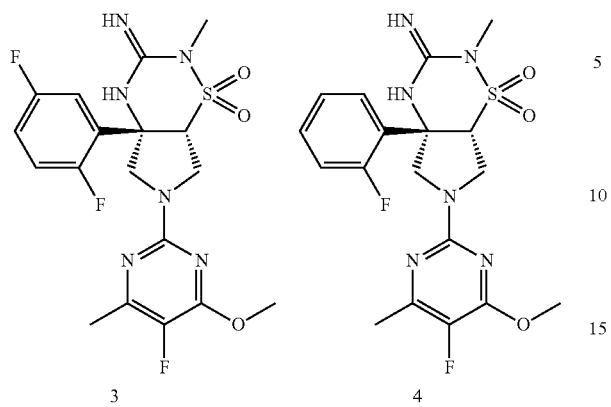
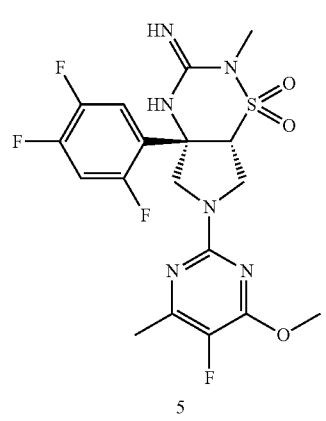
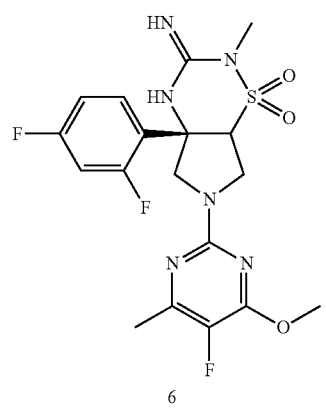
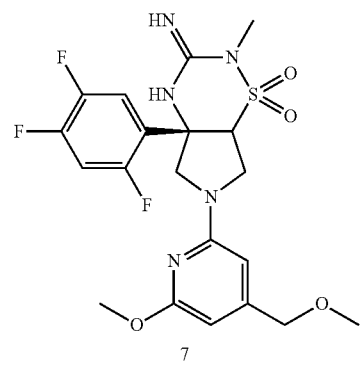
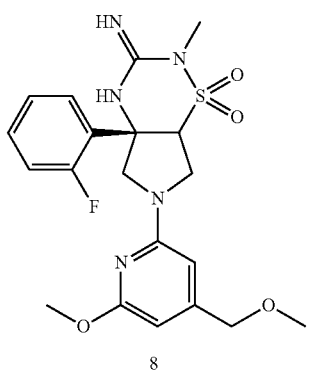
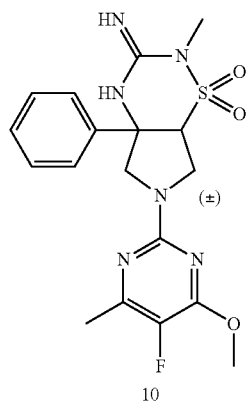
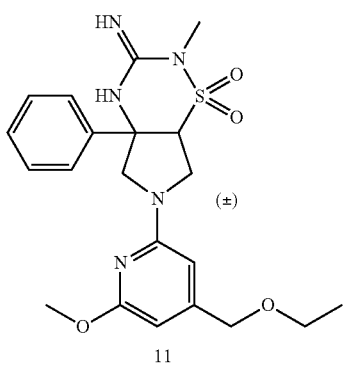
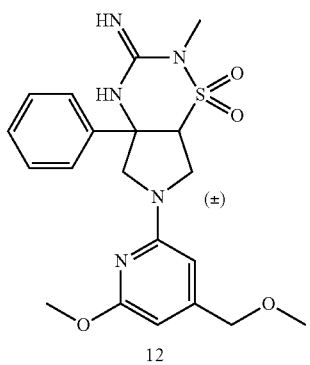

-continued

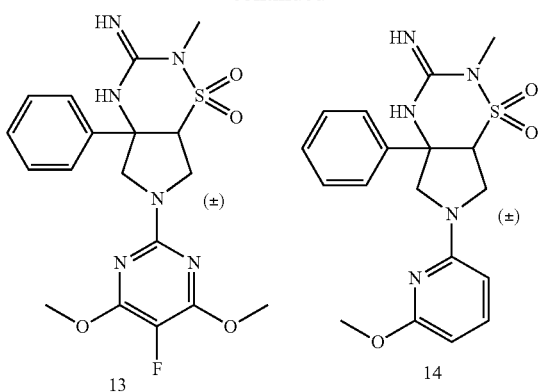

13

14

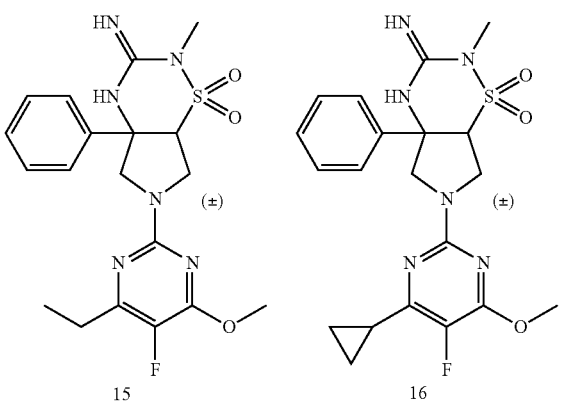

15

16

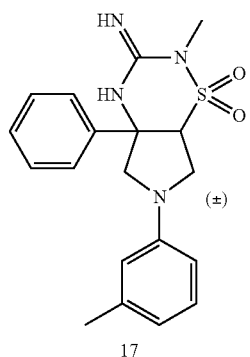

17

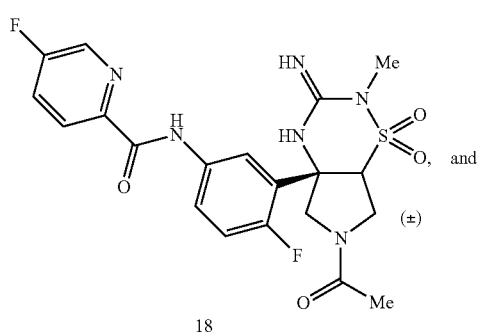

18

-continued

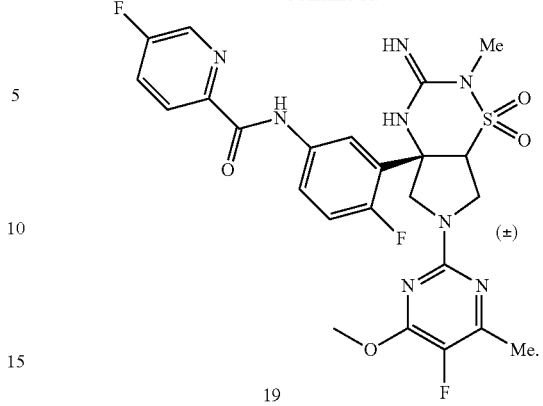

19

11. A pharmaceutical composition comprising at least one compound of claim 1, or a tautomer thereof, or a stereoisomer of said compound or said tautomer, or a pharmaceutically acceptable salt thereof, and a pharmaceutically acceptable carrier or diluent.

12. A pharmaceutical composition of claim 11, wherein said at least one additional therapeutic agent is at least one agent selected from:

$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

13. A method of treating, and/or delaying the onset of an amyloid β pathology ("Aβ pathology") and/or one or more symptoms of said pathology wherein said Aβ pathology is selected from Alzheimer's disease, Down's syndrome, Parkinson's disease, memory loss, memory loss associated with Alzheimer's disease, memory loss associated with Parkinson's disease, attention deficit symptoms, attention deficit symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, diabetes-associated amyloidogenesis, hemodialysis complications (from $\beta_2$ microglobulins and complications arising therefrom in hemodialysis patients), scrapie, bovine spongiform encephalitis, traumatic brain injury ("TBI"), Creutzfeld-Jakob disease, and traumatic brain injury, said method comprising administering an effective amount of a compound according to any one of claims 1-10 to a patient in need thereof.

14. A method of claim 13, wherein said Aβ pathology is Alzheimer's disease.

15. A method of treating type II diabetes comprising administering an effective amount of a compound according to any one of claims 1-10 to a patient in need thereof.

\* \* \* \* \*